United States Patent
Krishna et al.

(10) Patent No.: US 8,673,009 B2
(45) Date of Patent: Mar. 18, 2014

(54) SPINAL PROSTHESIS AND FACET JOINT PROSTHESIS

(75) Inventors: Manoj Krishna, Yarm (GB); Tai Friesem, Barwick (GB)

(73) Assignee: Spinadyne, Inc., Naples, FL (US)

(*) Notice: Subject to any disclaimer, the term of this patent is extended or adjusted under 35 U.S.C. 154(b) by 0 days.

(21) Appl. No.: 13/347,202

(22) Filed: Jan. 10, 2012

(65) Prior Publication Data

US 2012/0136446 A1    May 31, 2012

Related U.S. Application Data

(63) Continuation of application No. 11/397,756, filed on Apr. 4, 2006, which is a continuation-in-part of application No. 11/203,259, filed on Aug. 12, 2005, now abandoned, which is a continuation-in-part of application No. 10/970,091, filed on Oct. 21, 2004, now abandoned.

(51) Int. Cl.
A61F 2/44    (2006.01)

(52) U.S. Cl.
USPC ..................... 623/17.14; 623/17.15

(58) Field of Classification Search
USPC ............................ 623/17.11–17.16
See application file for complete search history.

(56) References Cited

U.S. PATENT DOCUMENTS

| | | |
|---|---|---|
| 4,349,921 A | 9/1982 | Kuntz |
| 4,368,997 A | 1/1983 | Shemtov |
| 4,488,542 A | 12/1984 | Helland |
| 5,034,011 A | 7/1991 | Howland |
| 5,122,140 A | 6/1992 | Asche et al. |
| 5,258,031 A | 11/1993 | Salib et al. |
| 5,314,477 A | 5/1994 | Marnay |
| 5,375,823 A | 12/1994 | Navas |
| 5,401,269 A | 3/1995 | Buttner-Janz et al. |
| 5,423,816 A | 6/1995 | Lin |
| 5,425,773 A | 6/1995 | Boyd et al. |
| 5,480,401 A | 1/1996 | Navas |
| 5,507,816 A | 4/1996 | Bullivant |
| 5,556,431 A | 9/1996 | Buttner-Janz |
| 5,562,736 A | 10/1996 | Ray et al. |
| 5,562,737 A | 10/1996 | Graf |
| 5,562,738 A | 10/1996 | Boyd et al. |
| 5,672,175 A | 9/1997 | Martin |
| 5,676,701 A | 10/1997 | Yuan et al. |
| 5,733,284 A | 3/1998 | Martin |
| 5,755,796 A | 5/1998 | Ibo et al. |

(Continued)

FOREIGN PATENT DOCUMENTS

FR    2728158 A1    6/1996

*Primary Examiner* — Eduardo C. Robert
*Assistant Examiner* — Julianna N Harvey
(74) *Attorney, Agent, or Firm* — Christopher & Weisberg, P.A.

(57) ABSTRACT

A lumbar disc prosthesis is provided including a first member with a vertebral disc contact surface and a recessed portion on an opposing surface thereof; a second member with a vertebral disc contact surface and a protruding portion on an opposing surface thereof. The protruding portion of the second member engages with the recessed portion of the first member in use. A facet joint prosthesis is provided, including a first member for attachment to a first posterior lumbar disc in use and a second member for attachment to a second posterior lumbar disc in use, where at least a part of the first member is telescopically mounted in at least a part of the second member in use.

6 Claims, 52 Drawing Sheets

(56) References Cited

U.S. PATENT DOCUMENTS

| | | |
|---|---|---|
| 5,782,832 A | 7/1998 | Larsen et al. |
| 5,888,226 A * | 3/1999 | Rogozinski ............... 623/17.16 |
| 5,899,941 A | 5/1999 | Nishijima et al. |
| 6,019,792 A | 2/2000 | Cauthen |
| 6,039,763 A | 3/2000 | Shelokov |
| 6,063,121 A | 5/2000 | Xavier et al. |
| 6,113,637 A | 9/2000 | Gill et al. |
| 6,146,421 A | 11/2000 | Gordon et al. |
| 6,228,118 B1 | 5/2001 | Gordon |
| 6,241,730 B1 | 6/2001 | Alby |
| 6,267,764 B1 | 7/2001 | Elberg |
| 6,283,968 B1 | 9/2001 | Mehdizadeh |
| 6,296,644 B1 | 10/2001 | Saurat et al. |
| 6,306,136 B1 | 10/2001 | Baccelli |
| 6,368,350 B1 | 4/2002 | Erickson et al. |
| 6,375,683 B1 | 4/2002 | Crozet et al. |
| 6,402,750 B1 | 6/2002 | Atkinson et al. |
| 6,436,098 B1 | 8/2002 | Michelson |
| 6,440,168 B1 | 8/2002 | Cauthen |
| 6,520,996 B1 | 2/2003 | Manasas et al. |
| 6,527,804 B1 | 3/2003 | Gauchet et al. |
| 6,540,785 B1 | 4/2003 | Gill et al. |
| 6,579,320 B1 | 6/2003 | Gauchet et al. |
| 6,620,164 B2 | 9/2003 | Ueyama et al. |
| 6,626,904 B1 | 9/2003 | Jammet et al. |
| 6,626,905 B1 | 9/2003 | Schmiel et al. |
| 6,669,729 B2 | 12/2003 | Chin |
| 6,679,915 B1 | 1/2004 | Cauthen |
| 6,682,562 B2 | 1/2004 | Viart et al. |
| 6,706,068 B2 | 3/2004 | Ferree |
| 6,726,720 B2 | 4/2004 | Ross et al. |
| 6,733,532 B1 | 5/2004 | Gauchet et al. |
| 6,770,095 B2 | 8/2004 | Grinberg et al. |
| 6,802,867 B2 | 10/2004 | Manasas et al. |
| 6,830,570 B1 | 12/2004 | Frey et al. |
| 6,835,205 B2 | 12/2004 | Atkinson et al. |
| 6,835,207 B2 | 12/2004 | Zacouto et al. |
| 6,852,128 B2 | 2/2005 | Lange |
| 6,878,167 B2 | 4/2005 | Ferree |
| 6,936,070 B1 | 8/2005 | Muhanna |
| 6,936,071 B1 | 8/2005 | Marnay et al. |
| 6,945,974 B2 | 9/2005 | Dalton |
| 6,972,037 B2 | 12/2005 | Zubok et al. |
| 6,974,478 B2 | 12/2005 | Reiley et al. |
| 6,986,771 B2 | 1/2006 | Paul et al. |
| 6,986,789 B2 | 1/2006 | Schultz et al. |
| 6,989,011 B2 | 1/2006 | Paul et al. |
| 6,994,727 B2 | 2/2006 | Khandkar et al. |
| 7,001,432 B2 | 2/2006 | Keller et al. |
| 7,014,633 B2 | 3/2006 | Cragg |
| 7,025,787 B2 | 4/2006 | Bryan et al. |
| 7,029,475 B2 | 4/2006 | Panjabi |
| 7,033,392 B2 | 4/2006 | Schmiel et al. |
| 7,037,340 B2 | 5/2006 | Gau |
| 7,041,136 B2 | 5/2006 | Goble et al. |
| 7,048,764 B2 | 5/2006 | Ferree |
| 7,052,515 B2 | 5/2006 | Simonson |
| 7,074,237 B2 | 7/2006 | Goble et al. |
| 7,074,238 B2 | 7/2006 | Stinson et al. |
| 7,083,622 B2 | 8/2006 | Simonson |
| 7,083,649 B2 | 8/2006 | Zucherman et al. |
| 7,087,084 B2 | 8/2006 | Reiley |
| 7,090,698 B2 | 8/2006 | Goble et al. |
| 7,195,643 B2 | 3/2007 | Jackson |
| 7,202,992 B2 | 4/2007 | Kawai |
| 7,204,852 B2 | 4/2007 | Marnay et al. |
| 7,207,992 B2 | 4/2007 | Ritland |
| 7,270,681 B2 | 9/2007 | Cauthen |
| 7,276,082 B2 | 10/2007 | Zdeblick et al. |
| 7,282,065 B2 | 10/2007 | Kirschman |
| 7,291,150 B2 | 11/2007 | Graf |
| 7,326,210 B2 | 2/2008 | Jahng et al. |
| 7,329,258 B2 | 2/2008 | Studer |
| 7,331,995 B2 | 2/2008 | Eisermann et al. |
| 7,503,934 B2 | 3/2009 | Eisermann et al. |
| 7,556,651 B2 | 7/2009 | Humphreys et al. |
| 2003/0040802 A1 | 2/2003 | Errico et al. |
| 2003/0208273 A1* | 11/2003 | Eisermann et al. ......... 623/17.14 |
| 2004/0010316 A1 | 1/2004 | William et al. |
| 2004/0138749 A1* | 7/2004 | Zucherman et al. ....... 623/17.11 |
| 2004/0143332 A1* | 7/2004 | Krueger et al. ............ 623/17.14 |
| 2004/0158254 A1 | 8/2004 | Eisermann |
| 2004/0158328 A1 | 8/2004 | Eisermann |
| 2004/0176772 A1 | 9/2004 | Zubok et al. |
| 2004/0176845 A1 | 9/2004 | Zubok et al. |
| 2004/0176853 A1 | 9/2004 | Sennett et al. |
| 2004/0181285 A1 | 9/2004 | Simonson |
| 2004/0236329 A1 | 11/2004 | Panjabi |
| 2005/0043800 A1 | 2/2005 | Paul et al. |
| 2005/0049592 A1 | 3/2005 | Keith et al. |
| 2005/0049708 A1 | 3/2005 | Atkinson et al. |
| 2005/0149188 A1 | 7/2005 | Cook et al. |
| 2005/0154461 A1 | 7/2005 | Humphreys et al. |
| 2005/0154464 A1 | 7/2005 | Humphreys et al. |
| 2005/0154466 A1 | 7/2005 | Humphreys et al. |
| 2005/0154467 A1 | 7/2005 | Peterman et al. |
| 2005/0171543 A1 | 8/2005 | Timm et al. |
| 2005/0171610 A1 | 8/2005 | Humphreys et al. |
| 2005/0177156 A1 | 8/2005 | Timm et al. |
| 2005/0177164 A1 | 8/2005 | Walters et al. |
| 2005/0182400 A1 | 8/2005 | White |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0222569 A1 | 10/2005 | Panjabi |
| 2005/0228497 A1 | 10/2005 | Ferree et al. |
| 2005/0240265 A1 | 10/2005 | Kuiper et al. |
| 2005/0245930 A1 | 11/2005 | Timm et al. |
| 2005/0256578 A1 | 11/2005 | Blatt et al. |
| 2005/0261682 A1 | 11/2005 | Ferree |
| 2006/0036240 A1 | 2/2006 | Colleran et al. |
| 2006/0036326 A1 | 2/2006 | Baumgartner et al. |
| 2006/0069438 A1 | 3/2006 | Zucherman et al. |
| 2006/0069441 A1 | 3/2006 | Zucherman et al. |
| 2006/0084994 A1 | 4/2006 | Atkinson et al. |
| 2006/0089717 A1 | 4/2006 | Krishna et al. |
| 2006/0149229 A1 | 7/2006 | Kwak et al. |
| 2006/0184171 A1 | 8/2006 | Biedermann et al. |
| 2006/0189984 A1 | 8/2006 | Fallin et al. |
| 2006/0247637 A1 | 11/2006 | Colleran et al. |
| 2006/0247779 A1 | 11/2006 | Gordon et al. |
| 2006/0285916 A1 | 12/2006 | Lu et al. |
| 2007/0179616 A1 | 8/2007 | Braddock, Jr. et al. |
| 2007/0225814 A1 | 9/2007 | Atkinson et al. |
| 2007/0225815 A1 | 9/2007 | Keith et al. |
| 2007/0225816 A1 | 9/2007 | Keith et al. |
| 2007/0233257 A1 | 10/2007 | Keith et al. |
| 2007/0239280 A1 | 10/2007 | Keith et al. |
| 2007/0270862 A1 | 11/2007 | Yu et al. |

* cited by examiner

TOP PLATE - TYPE A SOCKET DETAIL

TOP PLATE - TYPE A SOCKET DETAIL

TOP PLATE - TYPE A SOCKET DETAIL

TOP PLATE - TYPE A SOCKET DETAIL
Solid, inverse representation of socket shape

TOP PLATE - TYPE A SOCKET DETAIL
Axial View

TOP PLATE - TYPE A SOCKET DETAIL
Anterior angle sweep
A/P View
Posterior angle sweep
Radius sweep TOP PLATE - TYPE A SOCKET DETAIL
M/L View

SOCKET OPTIONS

Independent sockets
captive on male sphere
limited sideways
rotation

EXPLODED DETAIL (FIN-TYPE IMPLANTS)

Section A-A

Section A-A

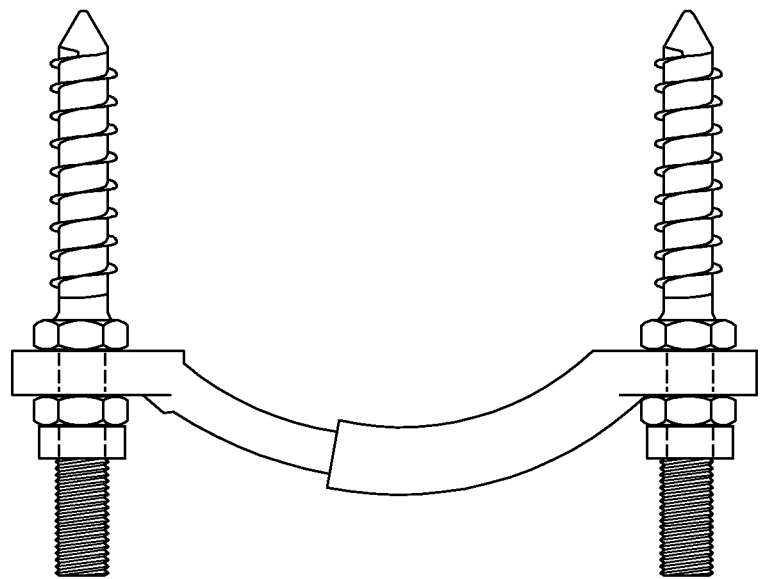
FIG. 44b
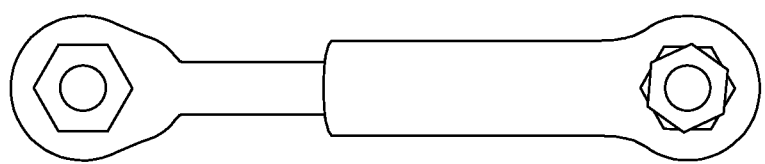
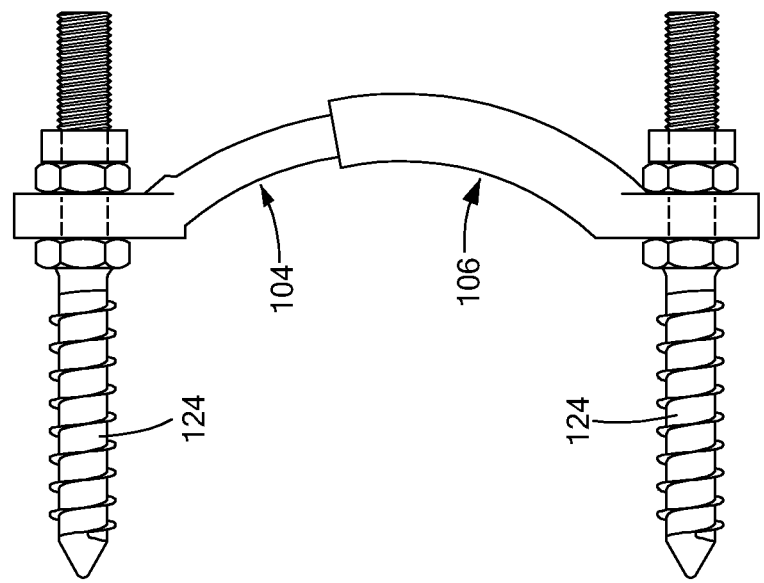
FIG. 44a

FLEXION AND EXTENSION

FLEXION AND EXTENSION

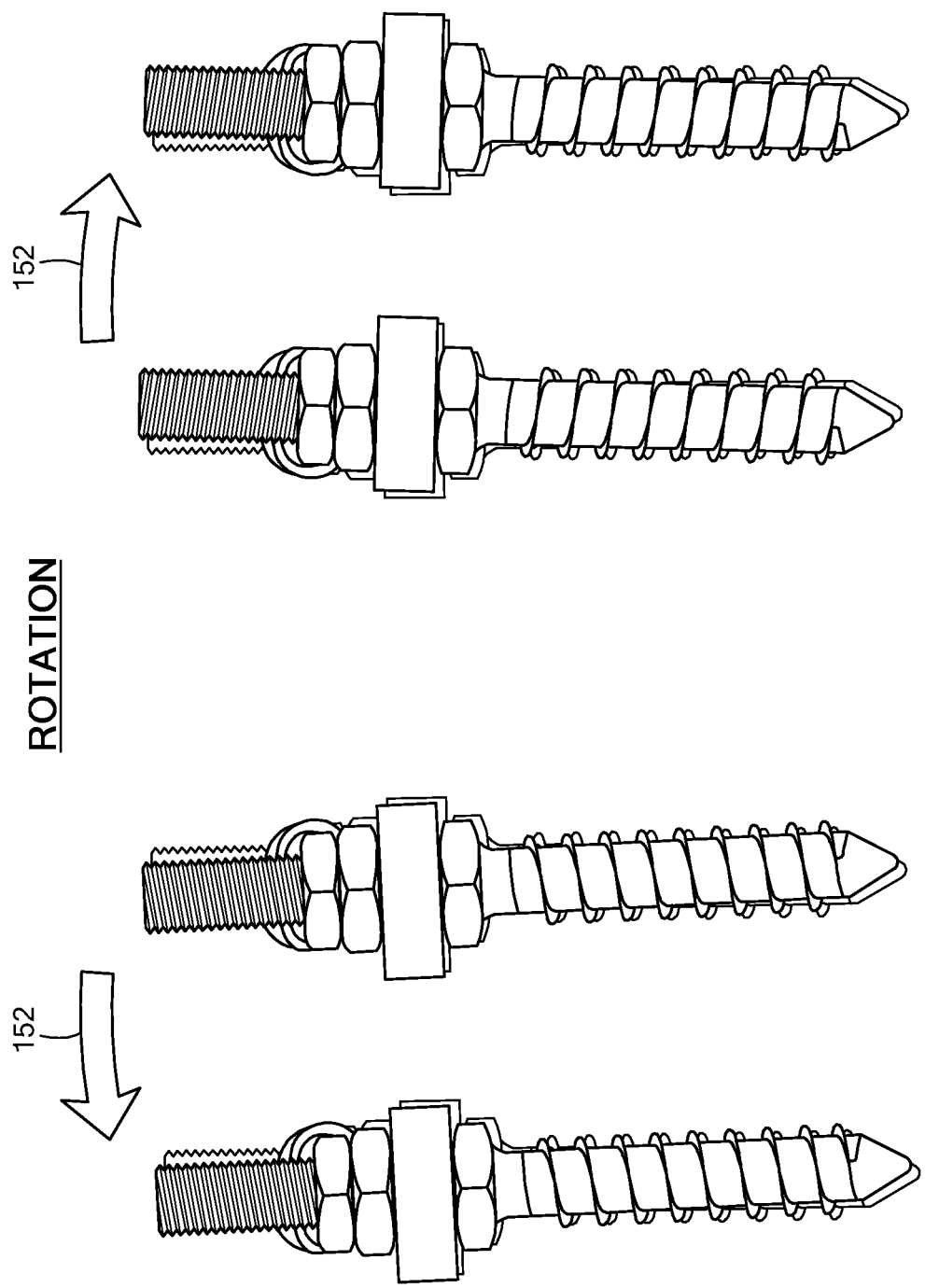

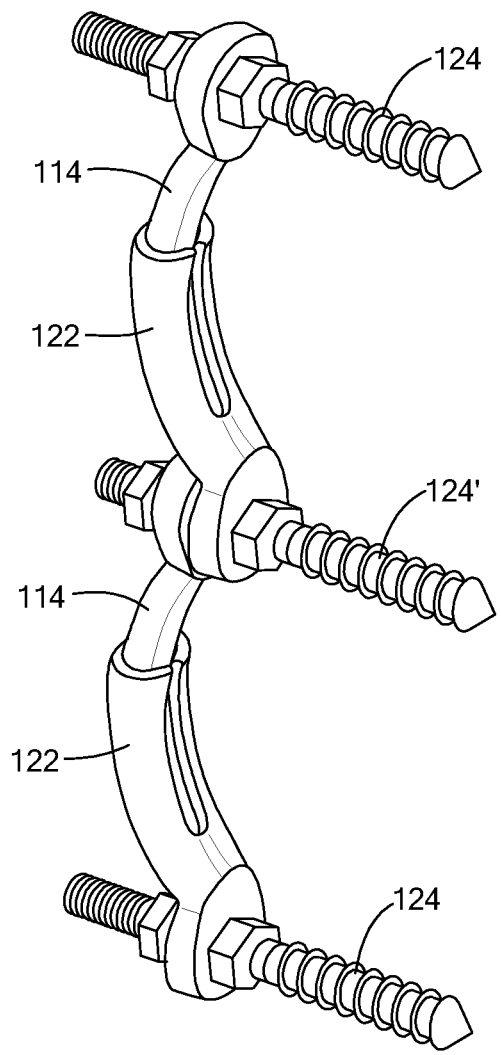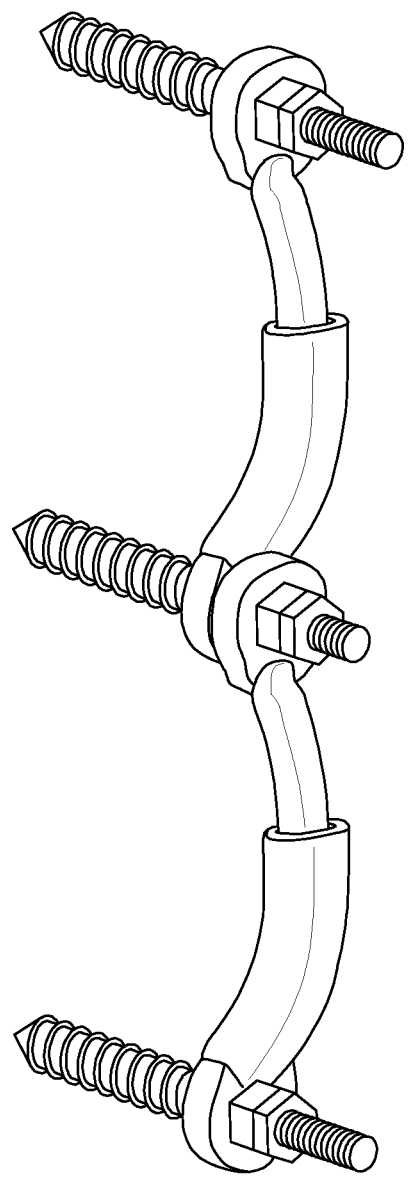
*FIG. 48c*
*FIG. 48d*

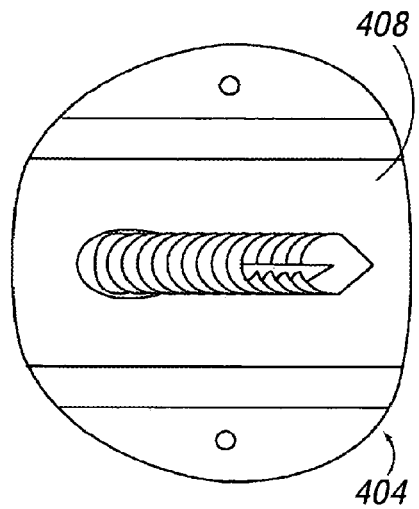
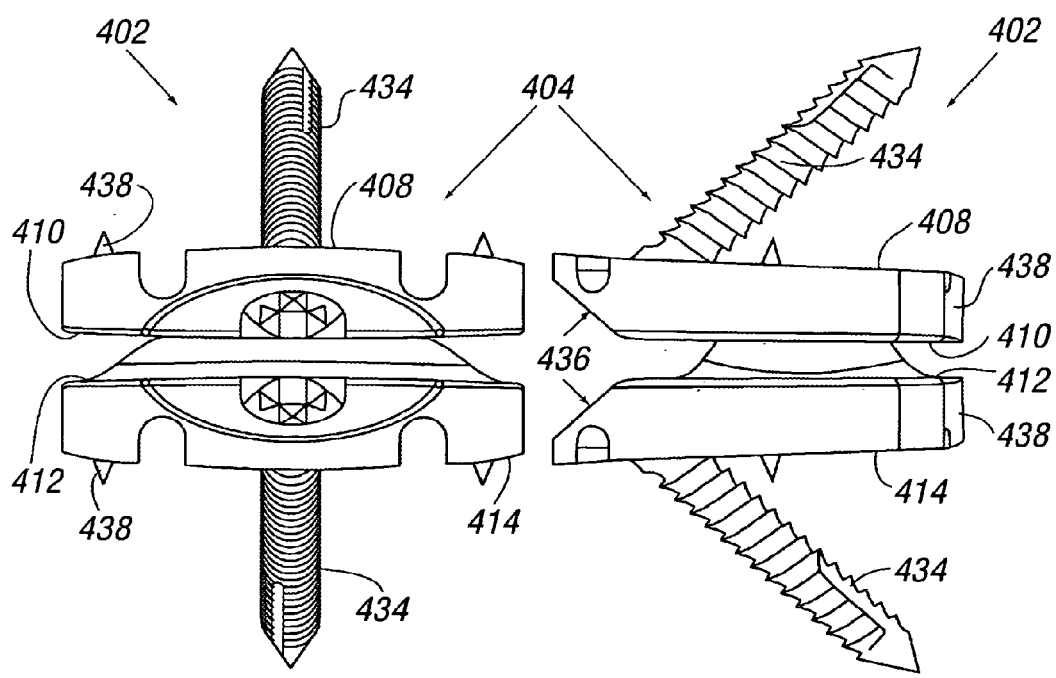
FIG. 56a
FIG. 56b
FIG. 56c

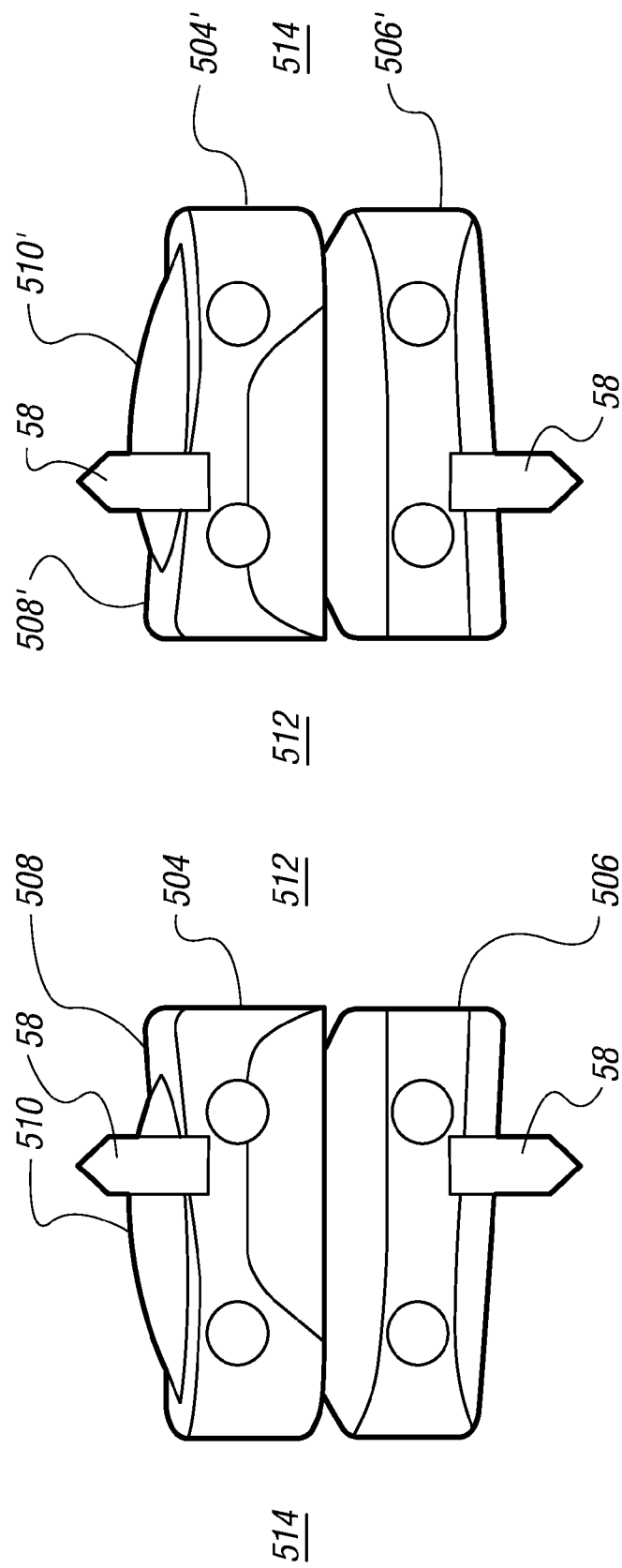

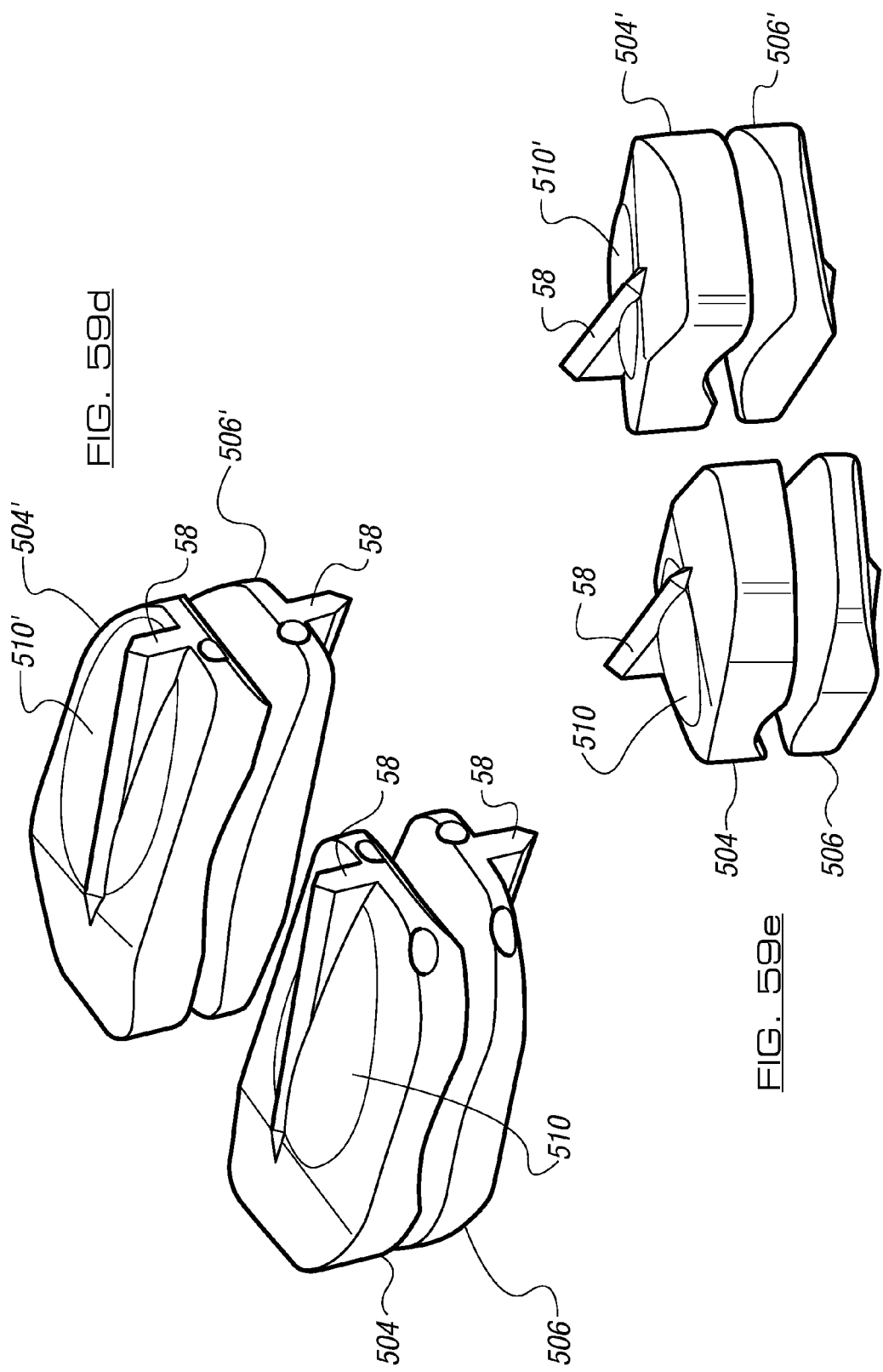

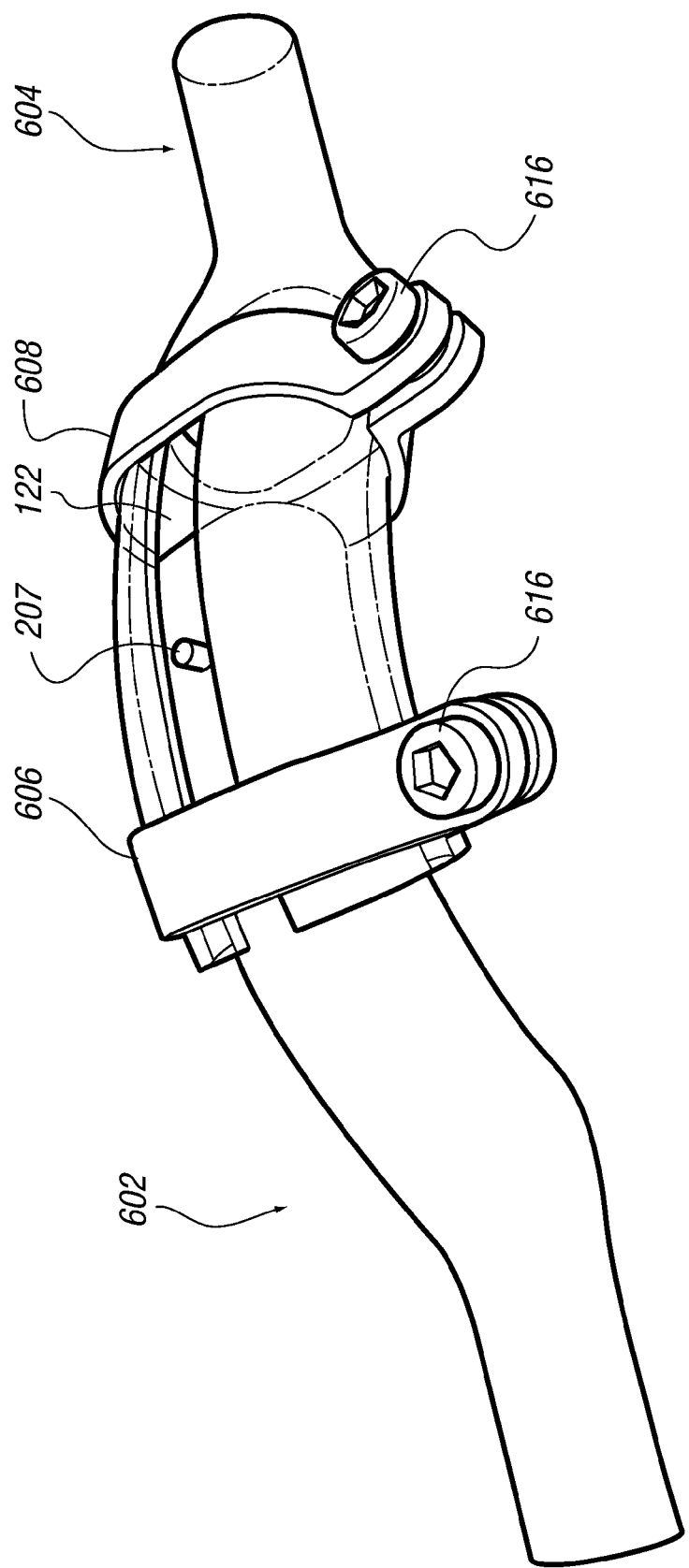

SPINAL PROSTHESIS AND FACET JOINT PROSTHESIS

CROSS-REFERENCE TO RELATED APPLICATION

This application is a continuation of pending U.S. application Ser. No. 11/397,756, filed Apr. 4, 2006, which is a continuation-in-part of U.S. application Ser. No. 11/203,259, filed on Aug. 12, 2005, which is a continuation-in-part of U.S. application Ser. No. 10/970,091, filed on Oct. 21, 2004, the entirety of all of which is incorporated herein by reference.

STATEMENT REGARDING FEDERALLY SPONSORED RESEARCH OR DEVELOPMENT n/a

FIELD OF THE INVENTION

This invention relates to devices and surgical methods for the treatment of various types of spine pathologies. It deals with the development of an artificial facet joint, and an artificial lumbar disc replacement that is specifically designed to be inserted from a posterior approach to the spine. It also deals with the development of an artificial disc replacement that can be inserted from an anterior approach to the spine.

BACKGROUND OF THE INVENTION

Back pain affects 40% of the population. Up to 20% of the population visit their family doctor requesting help with their back problem. Up to 30% of patients continue to complain of significant back pain at one year following the onset of their symptoms.

Although the majority of patients have minor sprains or strains which are self limiting, a significant number of patients go on to develop severe chronic mechanical lower back pain which is caused by inflammatory changes in the lumbar disc associated with degeneration.

Another group of patients with degenerative spine disease go on to develop degenerative spondylolisthesis and spinal stenosis. This is a narrowing of the spinal canal caused primarily by degenerative changes in the facet joint, combined with a loss of normal disc height and buckling of the ligamentum flavum.

Degeneration occurs in a spinal segment. The spinal segment consists of the lumbar disc anteriorly and two facet joints posteriorly. This is therefore called a three joint complex. Degenerative changes in the disc can lead to changes in the facet joint and vice versa. In patients with significant lumbar disc degeneration, the facet joints are also usually degenerate.

Pain occurs from all components of the three joint complex, including the facet joints and the disc. The facet joint is in fact a synovial joint and suffers from the problems that are known to affect other synovial joints in the body like the hip and the knee. The facet joint particularly contributes to degenerate spondylolisthesis and commonly occurs at levels where the facet joints are sagittally orientated, for example at the L4/5 level.

After failing all the conservative treatments available, a minority of patients with back pain or leg pain will go on to require surgical intervention. For patients with predominantly lower back pain who have a degenerative lumbar disc, some surgeon's consider the solution lies in removing the pain generator which is the disc and restoring normal loading across the disc by doing an inter-body stabilisation procedure.

The two types of inter-body stabilisation procedure currently available are an artificial disc replacement performed anteriorly and inter-body fusions performed anteriorly and/or posteriorly. These inter-body stabilisation procedures are often combined with decompression of the spinal canal and the nerve roots if there is nerve root impingement.

As far as inter-body fusions are concerned, there are two basic strategies that surgeons adopt. The first is to perform an anterior inter-body fusion combined with posterior stabilisation externally of the spinal canal. Anterior inter-body fusion on its own is still questioned because it does not provide a posterior tension band. An alternative strategy is a posterior lumbar inter-body fusion, where the entire inter-body fusion procedure is performed from behind and it is combined with neural decompression as well as removal of the degenerative facet joints. Posterior lumbar inter-body fusion also provides a posterior tension band. This strategy therefore deals with all three joint components which can generate possible pain at the disc level, including the lumbar disc, the neural structures and the facet joints.

When it comes to lumbar disc arthroplasty procedures, these are performed via an anterior lumbar approach. The disc is removed and an artificial lumbar disc is inserted into the space. This removes the pain generator and allows normal loading across the disc, as well as allowing some movement at this level. The advantage of this is to reduce the strains on the disc above and therefore reduce the chances of adjacent segment degeneration. Several studies have shown that adjacent segment degeneration can occur above a fused segment because of the increased loads being transmitted to this level.

One of the disadvantages of anterior lumbar arthroplasty is that the facet joints at this level continue to move and also continue to act as a pain generator. In addition, if there is any neural impingement, these symptoms can continue. The other disadvantage of anterior lumbar arthroplasty is that the majority of spine surgeons are not familiar with the anterior approach, and although complications are uncommon, they can be life and limb threatening when they do occur.

There is therefore a concern among researchers and the surgical community, that long term results of anterior lumbar disc arthroplasty may be compromised by progressive degeneration of the facet joint at the same level. In addition, after lumbar disc arthroplasty, several patients continue to complain of facet joint pain because of increased loads being placed on the facet joint as a result of the surgical procedure.

At present there is no posterior lumbar arthroplasty procedure available. It is therefore an aim of the present invention to provide an artificial lumbar disc that can be inserted posteriorly, thereby delivering the advantages of approaching the spine posteriorly and removing the disadvantages associated with approaching the spine anteriorly.

It is a further aim of the present invention to provide a facet joint replacement prosthesis.

It is a yet further aim of the present invention to provide a lumbar prosthetic system that deals with the painful disc, the neural impingement and the painful facet joints by providing a combination of a lumbar disc prosthesis and a facet joint prosthesis as a single unit.

It is a further aim of the present invention to provide an artificial disc prosthesis that utilises one or more of the features and advantages provided by the posteriorly inserted disc but which can be inserted anteriorly.

It is a yet further aim of the present invention to provide a prosthetic system that deals with the painful disc, the neural impingement and the painful facet joints by providing a combination of a disc prosthesis and a facet joint prosthesis as a single system that works together.

SUMMARY OF THE INVENTION

According to a first aspect of the present invention there is provided a disc prosthesis, said disc prosthesis including a pair of disc members, the first member of said disc pair having a vertebral endplate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, and wherein the inner or opposing surface of at least the first disc member is provided with at least three sections; a middle section and at least two end sections, the recessed portion being provided in the middle section and the thickness or depth of the middle section being less compared to the two end sections thereof.

In one embodiment the end sections, typically located adjacent the anterior and posterior edges of the prosthesis are substantially surfaces which are planar in form. Thus, the planar ends sections are different in form to the curved middle recessed section.

The geometry of the middle and end sections of at least the first disc member allows contact to be made between the recessed and protrusion portions of the first and second disc members and for a gap to be formed adjacent the end sections of the disc members when the prosthesis is in a neutral position. When the prosthesis is in extension (i.e. the upper or first disc member moves posteriorly relative to the lower or second disc member), the gap between the end section at the anterior end increases, thereby causing the annulus anteriorly to tighten. Due to the geometry of the planar slopes within the prosthesis, the annulus will tighten not only anteriorly in flexion but laterally as well. This results in a physiological stop to further extension. Similarly in flexion the upper disc member moves anteriorly relative to the lower disc member, resulting in an increased gap posteriorly between the two disc members, and this causes the annulus posteriorly and laterally to tighten, resulting in a physiological stop to further flexion.

In one embodiment the middle section is located substantially centrally of the prosthesis. The end sections can be of substantially the same dimensions or substantially different dimensions.

Preferably the inner or opposing surface of the second disc member is provided with at least three sections; a middle section and at least two end sections, the protruding portion being provided in the middle section of the disc member.

In one embodiment the boundaries of the middle and end sections of one or both disc members can be arranged transversally thereof (i.e. in medial to lateral plane).

In one embodiment the boundaries of the middle and end sections of one or both disc members are arranged in anterior/posterior plane.

The middle and end sections of one or both disc members can be arranged along substantially the entire length thereof, or the middle and end sections of one or both disc members can be arranged in a substantially central part of the disc members.

In the embodiment where the prosthesis is inserted anteriorly, the middle or recessed portion of the first member is substantially curved and the curvature of the medial part of said recessed portion is substantially symmetrical to the curvature of the lateral part of said recessed portion. Thus, the lateral part of the recessed or middle portion has curvature corresponding to an arc of a circle which has a radius substantially equal to that of an arc of a circle corresponding to the curvature of the medial part of the recessed portion or middle section.

Preferably an anterior part of the recessed portion or middle section is substantially symmetrical to a posterior part of the recessed portion. The symmetry of the parts of typically about the mid point of the middle section.

In the anteriorly inserted embodiment, the protrusion portion of the second member is typically of substantially the same shape and/or dimensions as the recessed portion of the first member.

In the anteriorly inserted embodiment, the protrusion portion is preferably a rugby ball type shape with the radius of the curve of the protrusion portion in the medial-lateral plane being larger than the radius of the curve of the protrusion portion in the anterior-posterior plane. Thus, the protrusion portion is typically asymmetrical in the anterior-posterior plane compared to the medial to lateral plane.

Preferably one or both end sections of the inner or opposing surfaces of said first and/or second members are provided at an acute angle to the horizontal. For example, the inner end section surface of said first member can slope downwardly towards one or both ends of said member. The inner end section surface of said second member can slope downwardly towards the one or both ends of said member.

In the anteriorly inserted embodiment, the disc members are formed so as to have lordosis provided therein, such that the overall posterior height of the disc pair when assembled together is less than the anterior height.

Further preferably the outer and/or inner surfaces of said second disc member form a narrowing taper towards one or both ends of said disc member.

Preferably one or both ends of the first and/or second disc members have a narrowing taper (i.e. the ends of the prosthesis as a whole has a narrowing taper). This narrowing taper is as a result of the outer or vertebral end plate contact surface of said first and/or second disc member being provided at an acute angle with respect to the horizontal at one or both ends. These angled surfaces are preferably substantially planar in form. For example, the outer or vertebral end plate contact surface of the first disc member slopes downwardly towards the ends of the disc member and/or the outer or vertebral end plate contact surface of the second disc member slopes upwardly towards the ends of the disc member. The narrowing taper of the prosthesis is particularly advantageous as it allows easy insertion of the prosthesis in the disc space via a posterior route.

In one embodiment, such as for example in the posteriorly inserted prosthesis, the narrowing taper is provided at an anterior end of the prosthesis. Thus, the outer surfaces or vertebral endplate contact surfaces of the disc member(s) slope towards the opposing surfaces thereof at the anterior end of the disc member(s). This provides a "lead in" feature which increases the ease with which the front of the prosthesis can be inserted via a posterior route into the disc space. In this embodiment, where the disc is inserted through the posterior route, the overall height of the anterior part of the disc pair is greater than the posterior height, so as to place the two vertebral endplates in lordosis, when the discs are inserted.

In one embodiment, a narrowing taper is provided at the posterior end of the prosthesis. Thus, for example, the outer surfaces or vertebral endplate contact surfaces of the disc member(s) slope towards the opposing surfaces thereof at the posterior end of the disc member(s). The posterior angled surface allows the prosthesis in the neutral position to be placed such that the vertebral end plates are in lordosis The posterior end of the prosthesis typically slopes or tapers in an opposite direction to the anterior end.

Preferably the anterior end slope is substantially smaller than the posterior end slope in the embodiment where the disc prosthesis is inserted posteriorly.

Further preferably the outer and inner surface of said first disc member form a narrowing taper adjacent an end of said disc member in which attachment screws are to be located there through. The screw insertion hole is located posteriorly in the embodiment where the discs are inserted from the posterior route, and anteriorly where the discs are inserted through the anterior route.

Preferably the vertebral endplate contact surface of the first and/or second members of each disc pair is provided with attachment means for allowing attachment of the disc member to an adjacent disc in use.

The attachment means can include any or any combination of one or more screws, one or more apertures for the location of screws and/or any other suitable attachment device therewith, one or more tapered members, spikes or fins and/or any other conventional attachment apparatus.

In one embodiment the vertebral endplate contact surface of the first member of each disc pair includes a curved or convex shaped portion thereon. Preferably the disc pair is a lumber disc prosthesis which can be inserted anteriorly but preferably posteriorly.

Preferably the contours of the curved or convex shape portion corresponds substantially (i.e. is substantially complementary) to the concave or curved shape portion of the end surface of the vertebral body which the vertebral endplate contact surface of the prosthesis engages with in use. This provides an improved fit of the prosthesis in the disc space.

Preferably the longitudinal axis of the curved or convex shaped portion is parallel to the anterior-posterior axis of the vertebral endplate contact surface.

Preferably the height of the curved or convex shaped portion is greater towards the medial side than the lateral side. Thus the vertebral endplate contact surface slopes upwardly from the lateral side to the medial side.

The angle between the vertebral endplate contact surface of the first and second members or upper and lower disc members is approximately 7 degrees on the lateral side, but can vary.

Preferably the curved or convex shape portion on the vertebral endplate contact surface is substantially symmetrical about the anterior-posterior axis and/or medial to lateral axis.

The first and second members of the disc pair typically correspond to upper and lower disc members. The superior surface of the lower disc member has a protrusion thereon and the inferior surface of the upper disc member has a captive recess or socket thereon.

Preferably the recessed portion has two sloped surfaces associated therewith, typically corresponding to the end sections thereof, one surface leading anteriorly to the edge of the inferior surface and one surface leading posteriorly to the edge of the inferior surface. These sloping surfaces can be planar or can be slightly concave in form, but generally do not form the arc of a radius.

Preferably the disc prosthesis can be used in the cervical and/or lumbar spine in the embodiment where the prosthesis is inserted anteriorly.

Preferably the disc prosthesis can be used in the lumbar and/or thoracic spine where the prosthesis is inserted posteriorly.

The disc prosthesis of the present invention can be used to replace lumbar discs either anteriorly or posteriorly, and cervical discs anteriorly.

In the embodiment where the disc prosthesis of the present invention is inserted posteriorly, two disc pairs are required.

Thus, according to a second aspect of the present invention there is provided a lumbar disc prosthesis, said lumbar disc prosthesis including a pair of disc members, the first member of said disc pair having a vertebral endplate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, and wherein the spinal disc prosthesis includes a further pair of disc members, said further pair of disc members also including first and second members.

Preferably the disc pairs are minor images of each other.

Thus, the second aspect of the present invention provides a lumbar disc prosthesis having two disc member pairs and thus two separate articulating portions, one articulating portion on each pair of disc members. The disc member pairs are each independently inserted into the disc space on either side of the dural sac in use through the trans-foraminal or posterior route bilaterally and are provided a spaced distance apart in use to allow accommodation in accordance with the anatomy of the lateral aspect of the disc space. Thus, the disc prosthesis can be inserted through the posterior route whilst taking into account the neural anatomy posteriorly.

The lumbar disc prosthesis of the present invention can be inserted at all levels between L2 and the sacrum, typically depending on the level of expertise of the operating surgeon.

Preferably the first members of each disc pair are provided in the left and right areas of the disc space respectively in use. The second members of each disc pair are also provided in the left and right areas of the disc space respectively in use. Thus, each pair of members constitutes a left and right lumbar disc prosthesis.

In the posteriorly inserted lumbar disc prosthesis, the recessed portion or middle section of the first member is substantially curved and the curvature of the medial part of said recessed portion is asymmetrical to the curvature of the lateral part of said recessed portion.

The purpose of this asymmetry in the medial-lateral plane is to allow "capture" of the protruding portion of the second member. such that when two pairs of disc prostheses are placed in the patient, the two vertebrae can move from side to side as well as anteriorly and posteriorly.

In the posteriorly inserted embodiment, preferably the lateral part of the recess has curvature corresponding to an arc of a circle which has a radius greater that of an arc of a circle corresponding to the curvature of the medial part of the recessed portion. Further preferably the radius of the lateral part is at least twice as big as the radius of the medial part Preferably an anterior part of the recessed portion is substantially symmetrical to a posterior part of the recessed portion.

In the posteriorly inserted embodiment, the protrusion portion of the second member is typically of different shape and/or dimensions to the recessed portion of the first member. Thus, in one embodiment the protrusion portion is asymmetrical or forms an asymmetrical fit with the recessed portion. In an alternative embodiment the protrusion portion is symmetrical or forms a symmetrical fit with the recessed portion.

In the posteriorly inserted embodiment, the protrusion portion is preferably substantially dome shaped and makes contact with only a part of the recessed portion when assembled. However, the protrusion portion could contact a substantial part of the recessed portion when assembled if required.

Preferably the recessed portion is substantially an inversed dome shape.

In the posteriorly inserted embodiment, the protrusion portion is typically symmetrical in the anterior-posterior plane and in the medial to lateral plane. The curvature in the medial to lateral plane can be the same or different to that in the anterior to posterior plane.

According to a further aspect of the present invention there is provided a lumbar disc prosthesis, said disc prosthesis including a pair of disc members, the first member of said disc pair having a vertebral endplate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, and wherein the vertebral endplate contact surface of said first member includes a convex shaped portion thereon.

The lumbar disc prosthesis can be used in conjunction with a facet joint prosthesis also provided posteriorly to provide a system which can work together as a single unit to replace the painful disc, overcomes neural impingement and painful facet joints.

The facet joint prosthesis is formed such that the arc of rotation of the facet joint substantially matches the arc of rotation of the posterior disc prosthesis. As such, the "Instant Axis of Rotation" (IAR) of the two prosthesis forming the unit is substantially the same. Furthermore, the facet joint prosthesis stabilises and can unload the posterior disc prosthesis by pre-loading the segment into kyphosis.

Preferably the facet joint prosthesis typically includes a first member for attachment to a first vertebra of a corresponding disc and a second member for attachment to a second vertebra of a corresponding disc in use, and wherein at least a part of said first member is telescopically or slidably mounted in at least a part of said second member in use.

Preferably the first and second members are elongate members and the provision of one telescopically mounted in the other allows the distance between parts of the first and second members to be increased and/or decreased as required.

The first vertebra is typically an upper vertebra and the second vertebra is typically a lower vertebra.

The facet joint prosthesis allows replacement of existing facet joints to be undertaken at all lumbar levels from T12 to the sacrum.

The interconnecting first and second members are formed such that they can articulate to allow flexion-extension, small degrees of rotation and side to side flexion.

Preferably securing means are provided for insertion of the first and second members into each of the vertebral bodies above and below the disc between which the facet joint prosthesis is to be located. The first and second members can then be secured to said securing means. A plurality of first and second members can be attached to the securing means if required to form a stack, thereby allowing facet joint replacement at multiple levels within the spine.

The securing means can include any suitable type of surgical securing device, such as a pedicle screw.

In one embodiment the ends of the first and/or second members which are to be attached to the vertebral bodies are provided with at least one aperture through which the securing means are located.

In one embodiment the ends of the first and/or second members which are to be attached to the vertebral bodies are provided with substantially rounded and/or continuous ends to allow a clamp and pedicle screw or other securing means to be associated with the same.

Preferably locking means are provided on the first and/or second members to allow locking of the members together. The locking means can include any or any combination of one or more interengaging portions, one or more locking screws and/or the like.

In one embodiment the locking means includes one or more clamping rings. The clamping rings are located around the first and second members and can clamp the members in a suitable position relative to each other by applying a suitable clamping force thereto. The clamping force can be provided using one or more screws and/or the like.

Preferably each clamping ring is of sufficient size and dimensions to substantially encompass the outermost member. The free ends of the clamping ring can be moved towards or apart from each other using said one or more screws and/or other suitable engagement means.

Preferably two clamping rings are used to clamp the first and second members together. Movement of the clamping rings relative to each other on the members determines the range of movement of the first member relative to the second member and thus the range of movement of the facet joint prosthesis. Use of the clamping rings allows the prosthesis to achieve micro-motion or full motion. It also allows the prosthesis to act as a fusion rod or a dynamic rod, thereby allowing the prosthesis to be multi-functional and more flexible in its application.

Preferably guide means are provided on the first and/or second members to allow relative movement therebetween to be controlled or guided. The guide means can include a slot or enclosed channel provided on one of said members in which a rod or protrusion provided on the other of said members is slidably mounted. This is to prevent the two members of the facet prosthesis from disassociating from each other.

The clamping rings can be used to limit movement of the protrusion in the slot or enclosed channel or male member.

Preferably an interior surface of the clamping ring is provided with a protrusion part thereon which locates in said channel or slot when fitted to the device.

In one embodiment the slot provided on one of said members can be open ended.

Preferably a stop member is located in the channel of said second member. The stop member can act as a shock absorber. The stop member is preferably removably located in said channel.

In one embodiment a sleeve, made of any suitable material, such as for example silicon, plastic and/or the like can be present to cover the facet articulation.

According to a further aspect of the present invention there is provided a lumbar disc prosthesis, said lumbar disc prosthesis including a pair of disc members, the first member of said disc pair having a vertebral endplate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, and wherein the recessed portion of the first member is substantially curved and the curvature of the medial part of said recessed portion is asymmetrical to the curvature of the lateral part of said recessed portion.

According to a yet further aspect of the present invention there is provided a facet joint prosthesis, said prosthesis including a first member for attachment to a first disc in use and a second member for attachment to a second disc in use, and wherein at least a part of said first member is telescopically or slidably mounted in at least a part of said second member in use.

The facet joint prosthesis can be used alone or in combination with the disc prosthesis of the present invention. The facet joint replacement procedure of the present invention alone will have a role in the treatment of patients with spinal stenosis and adjacent level disc disease, where some stability is required at the disc level without fusing a particular disc segment. The facet prosthesis can partially constraining certain degrees of motion.

According to further independent aspects of the present invention there is provided a prosthesis system including a disc prosthesis and a facet joint prosthesis as hereinbefore described; a first or upper disc member; a second or lower disc member; a method of insertion of a lumbar disc prosthesis in a patient via a posterior route; a method of insertion of a facet joint replacement prosthesis in a patient via a posterior route and/or anterior route; and a method of insertion of a lumbar disc prosthesis in a patient via an anterior route;

According to an aspect of the present invention there is provided a prosthesis system, said system including a disc prosthesis and facet joint prosthesis, said disc prosthesis including a pair of disc members, the first member of said disc pair having a vertebral end plate contact surface and a recessed portion on an opposing surface thereof, the second member of said disc pair having a vertebral endplate contact surface and a protruding portion on an opposing surface thereof, the protruding portion of the second member engaging with the recessed portion of the first member in use, said facet joint prosthesis including a first member for attachment to a first posterior lumbar disc in use and a second member is provided for attachment to a second posterior lumbar disc in use, and wherein at least a part of said first member is telescopically mounted in at least a part of said second member in use.

It will be appreciated by persons skilled in the art that the upper or lower disc member in any of the embodiments can be used alone if required.

Any of the abovementioned features can be used alone or in combination with each other in a prosthesis according to the present invention.

Thus, the present invention overcomes the problems and disadvantages associated with current disc replacement strategies. It has all the benefits associated with posterior lumbar inter-body fusion surgery, but at the same time it allows movement at that level and reduces the strain on adjacent discs and the risks of adjacent segment disc failure. This invention also addresses all three pain generators at the lumbar disc level including the degenerative disc, the impingement of the neural structures, and the facet joint

BRIEF DESCRIPTION OF THE DRAWINGS

Generally, FIGS. 1-30 and 59a-59e relate to a lumbar disc prosthesis according to embodiments of the present invention for insertion via a posterior route, FIGS. 31-52b and 60a-61 relate to a facet joint replacement prosthesis according to embodiments of the present invention; and FIGS. 53a-58e show lumbar and cervical disc prosthesis according to embodiments of the present invention for insertion via an anterior route. More particularly.

FIGS. 44a-44d illustrate a side view, front view, perspective view from the rear and perspective view from the front of the facet joint replacement prosthesis in FIG. 31;

FIG. 46 illustrates end views of the facet replacement prosthesis showing the ability of the male and female components to undergo limited relative rotational movement;

FIGS. 48a-48d show a side view, front view, perspective view from the rear and perspective view from the front of facet joint prostheses when stacked respectively;

FIGS. 53a-53f show a lumbar disc prosthesis for insertion via an anterior route, particularly a top view of an upper disc member, anterior view of a pair of disc members, side view of a pair of disc members, posterior view of a pair of disc members, base view of a lower disc member, and anterior perspective view of a pair of disc members respectively;

FIGS. 56a-56e show a cervical disc prosthesis for insertion via an anterior route, particularly a top view of an upper disc member, anterior view of a pair of disc members, side view of a pair of disc members, posterior view of a pair of disc members, base view of a lower disc member, and anterior perspective view of a pair of disc members respectively;

FIGS. 58a-58e show the upper disc member in FIGS. 56a-56e, particularly a top view, anterior view, side view, posterior view, base view and perspective view respectively;

FIGS. 59a-59e illustrates a further embodiment of first and second member disc pairs with the upper vertebral endplate contact surface having a convex shaped portion provided thereon;

FIGS. 60a-60c illustrate a perspective view and partial cross sectional view with clamping rings separated and a partial cross sectional view with the clamping rings together respectively.

DETAILED DESCRIPTION OF THE INVENTION

Figure 1:
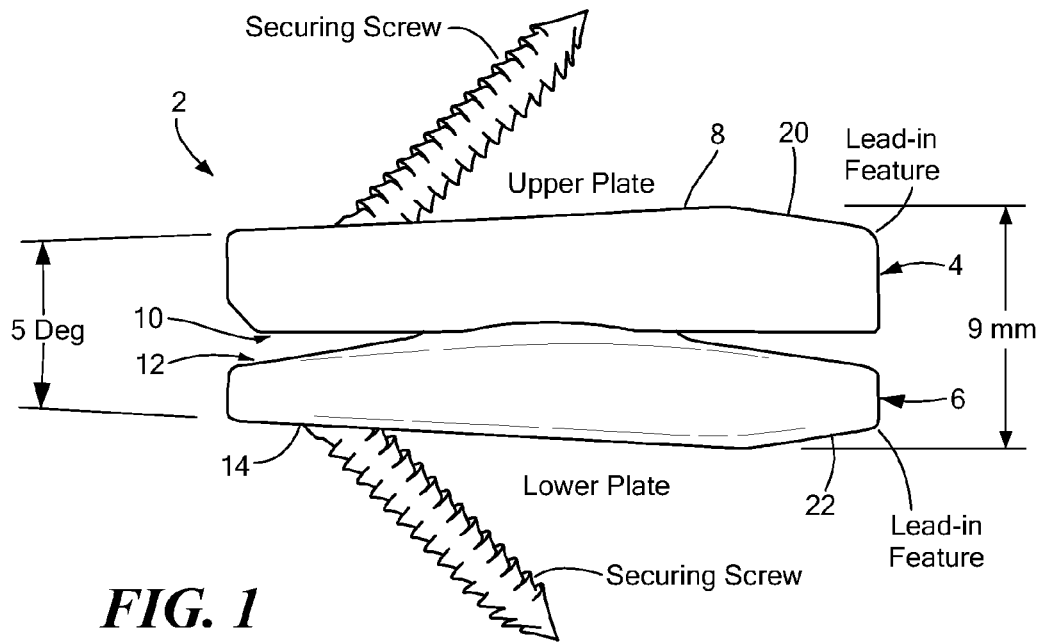
FIG. 1 is a side view of a lumbar disc prosthesis according to one embodiment of the present invention.

Lumbar Disc Prosthesis for Insertion Via a Posterior Route

Referring firstly to FIGS. 1-30, there is illustrated a lumbar disc prosthesis 2 which can be inserted into a lumbar disc space via a posterior route as a replacement for a diseased and/or damaged lumbar disc.

The disc prosthesis 2 includes two pairs of disc members, each pair including an upper disc member 4, 4' and a lower disc member 6, 6'. (Use of a reference numeral with ' thereafter refers to a second or further feature equivalent to the feature indicated by the reference numeral alone. Thus, disc member 4 refers to the first prosthesis pair upper member and disc member 4' refers to the second prosthesis pair upper member). The upper and lower disc members 4, 6; 4', 6' of each pair constitute a left and right disc prosthesis respectively. These disc members are shaped and dimensioned such that they can be inserted into a lumbar disc space either side of the dural sac whilst taking into account the posterior neural anatomy Each upper disc member 4, 4' includes a vertebral endplate contacting surface or superior surface 8, 8' and an inferior surface 10, 10'. Each lower disc member 6, 6' includes a superior surface 12, 12' and a vertebral endplate contacting surface or inferior surface 14, 14'.

A dome shaped protrusion 16 is formed substantially centrally of superior surface 12 of lower disc member 6. Protrusion 16 is received in a substantially central recess 18 on inferior surface 10 of upper disc member 4 as will be described in more detail below.

Both the superior surface 20 of upper member 4 and the inferior surface 22 of lower member 6 are angled to provide the prosthesis with a "lead in" or narrowing tapered feature. This lead in feature allows the prosthesis to enter the posterior disc space which is narrower than the anterior disc space. In addition to the lead in feature which is provided at the anterior or front end 24 of the prosthesis members, each prosthesis pair has a lordosis or narrowing taper angle towards the posterior or rear end 26 of the prosthesis members between the inferior surface 14 of the lower disc member 6 and superior surface 8 of the upper member 4 of approximately 6 degrees (this angle or any other angle mentioned hereinafter is for exemplary purposes and does not limit the invention in any way), as shown in FIG. 1. This makes the outer surfaces of the disc prosthesis pairs at the posterior and anterior ends substantially wedge shaped or tapered to allow ease of insertion into the disc space. The taper or angle of the outer surfaces at the posterior end is in an opposite direction to the taper or angle of the outer surface at the anterior end.

With reference to FIGS. 1-27, the superior surface of upper disc member 4 and the inferior surface of lower disc member 6 have attachment means in the form of screws 28 to allow attachment of the disc prosthesis to adjacent vertebrae when positioned in a patient. Apertures 30 are provided on the inferior and superior surfaces 10, 12 of the upper and lower disc members 4, 6 respectively of the prosthesis pairs to allow the insertion of screws 28 through the prosthesis disc members. The screws are typically fitted from the posterior end 26 and the screws and interior walls defining apertures 30 are provided at an acute angle to the vertical to allow ease of attachment. Apertures 30 and screws 28 within each pair diverge outwardly away from each other towards anterior end 24. The inferior surface on which these apertures are provided on the upper disc member is angled such that it slopes upwardly towards the superior surface of the upper disc member. The superior surface on which these apertures are provided on the lower disc member is angled such that it slopes downwardly towards the inferior surface of the lower disc member, thereby forming a narrowing taper at the posterior end of the lower disc member. These angled surfaces typically form, at least in part, the posterior end segments of the inferior and superior surfaces 48, 38 of the upper and lower disc members 4, 6 respectively. This feature is to allow ease of insertion of screws or other attachment means to anchor the prosthesis into the vertebra.

Figure 2:
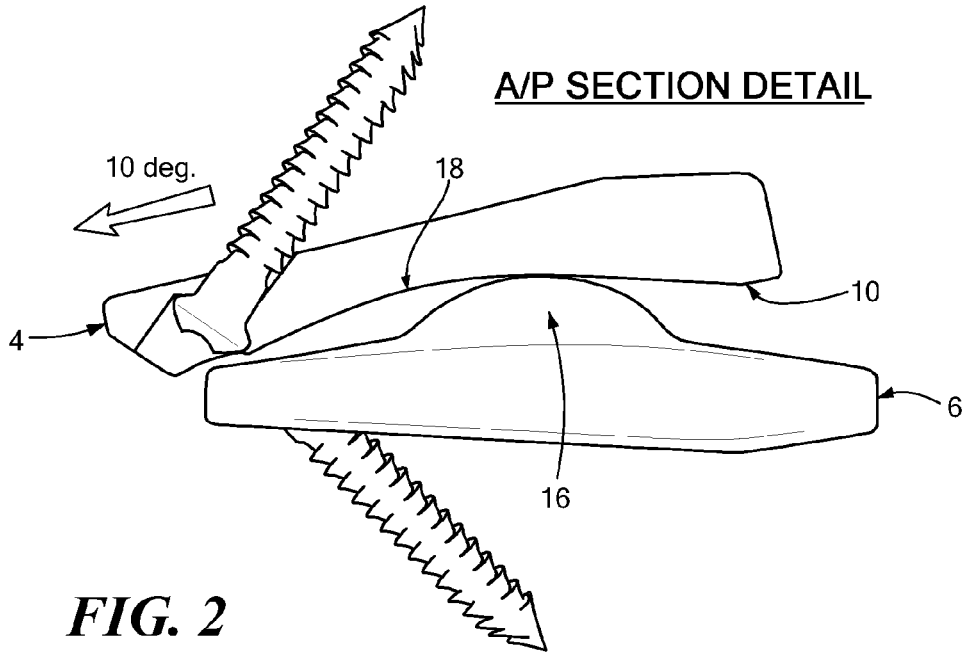
FIGS. 2-4 show the prosthesis in FIG. 1 with the upper disc member in extension, flexion and in a neutral position respectively.

With the protrusion 16 on lower member 6 located in recess 18 of upper member 4 when the prosthesis is assembled, relative movement between the upper and lower members 4, 6 allows the prosthesis to undergo extension and flexion. The substantially dome shaped protrusion 16 contacts only a part of the recess 18 due to differences in symmetry and geometry. In the example illustrated, the upper member 4 can move with respect to the lower member 6 through approximately 10 degrees in a posterior direction to allow extension of the prosthesis, as shown in FIG. 2. Due to the nature of the inferior surface 10 of upper disc member 4, as the upper member 4 goes into extension there is an increased distance adjacent anterior end 24 between the upper and lower members 4, 6. This results in a tightening of the annulus anteriorly, as is seen in physiological extension in the disc.

Figure 3:
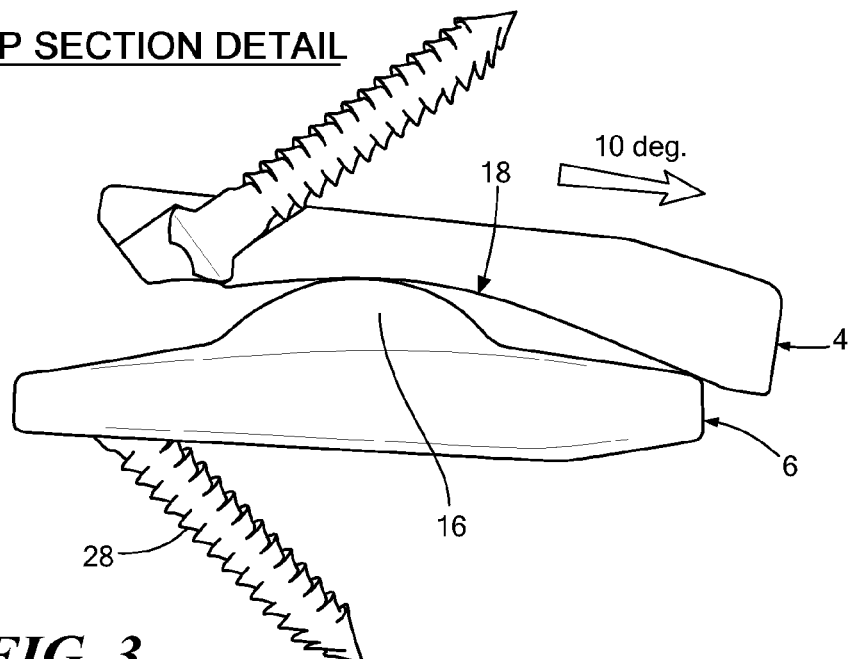
Figure 4:
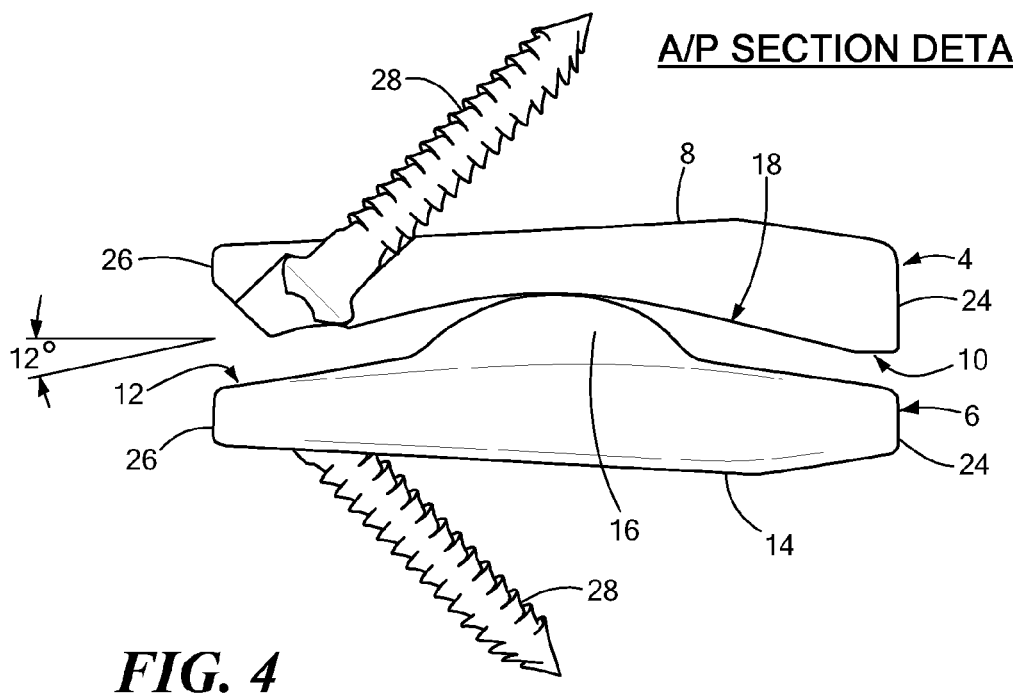
Figure 5:
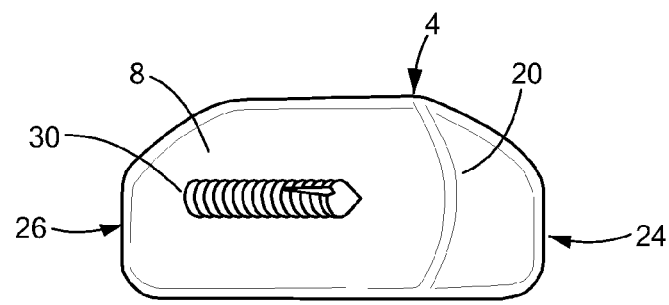
FIGS. 5 and 6 show the superior surfaces of the upper members of the left and right lumbar prosthesis pairs respectively.
Figure 6:
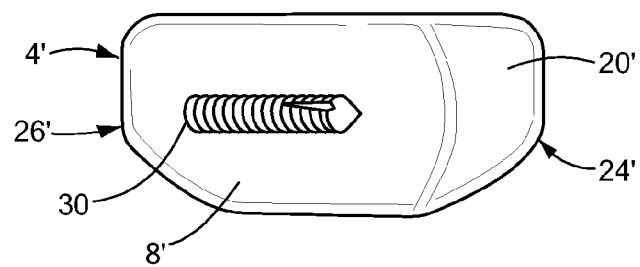
Figure 7:
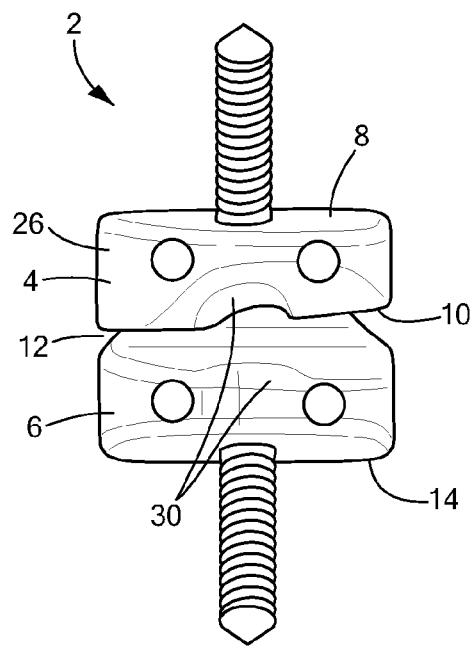
FIGS. 7 and 8 show rear views of the left and right lumbar prosthesis pairs respectively.
Figure 8:
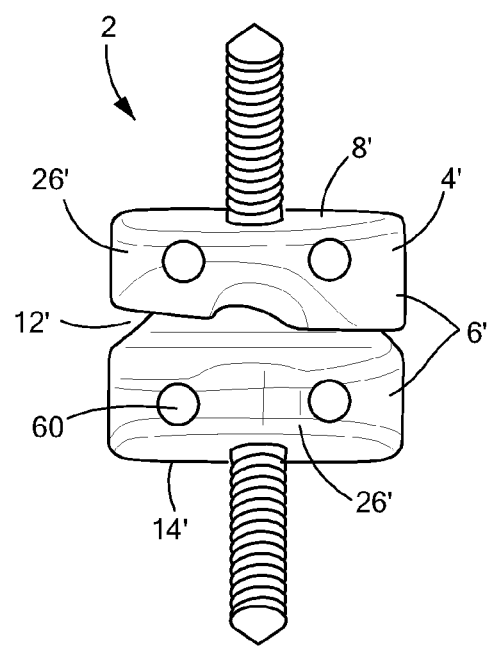
Figure 9:
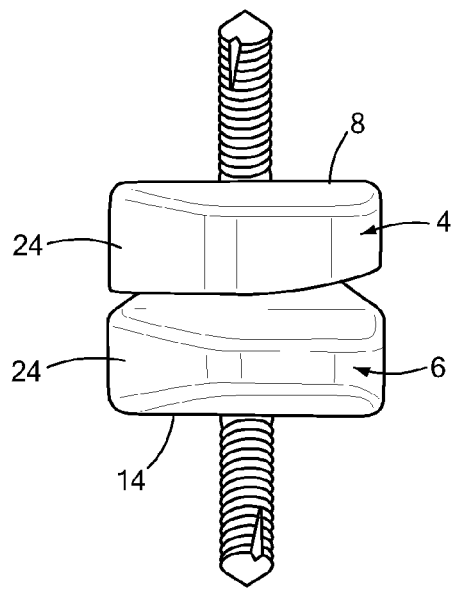
FIGS. 9 and 10 show front views of the left and right lumbar prosthesis pairs respectively.
Figure 10:
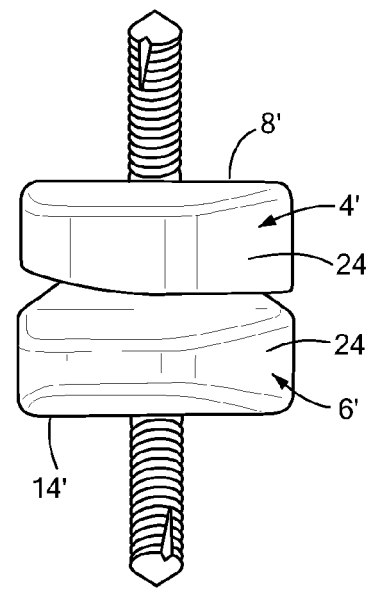
Figure 11:
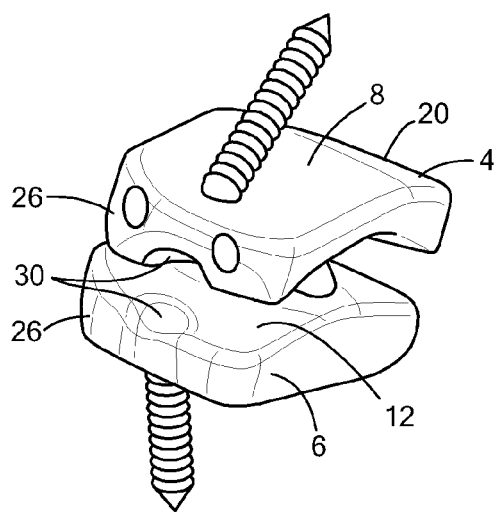
FIGS. 11 and 12 show oblique views of the left and right lumbar prosthesis pairs respectively.
Figure 12:
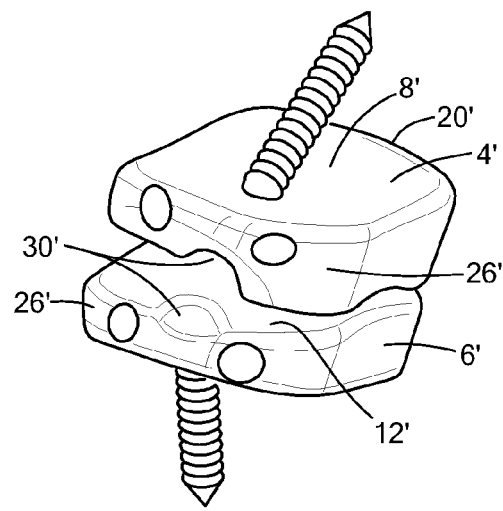
Figure 13:
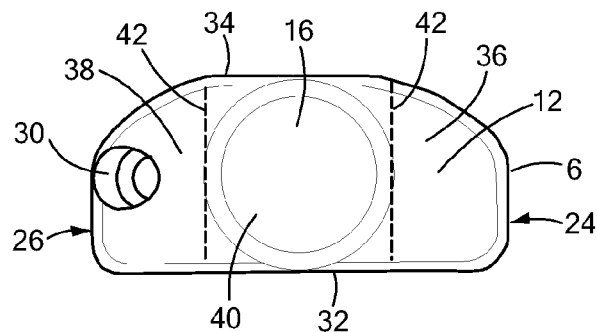
FIGS. 13 and 14 show the superior surfaces of the lower members of the left and right lumbar prosthesis pairs respectively.
Figure 14:
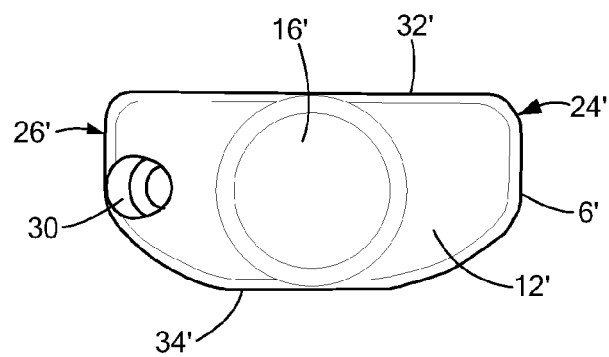
Figure 15:
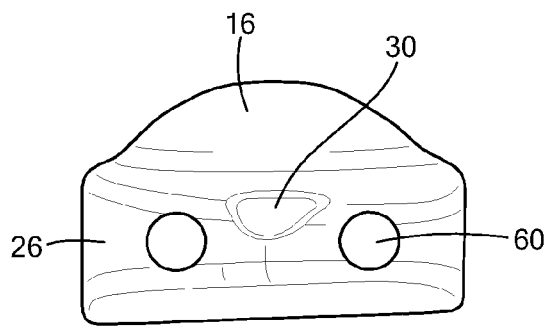
FIGS. 15 and 16 show rear views of the lower members of the left and right lumbar prosthesis pairs respectively.
Figure 16:
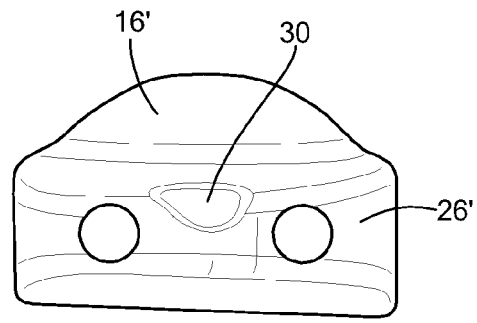
Figure 17:
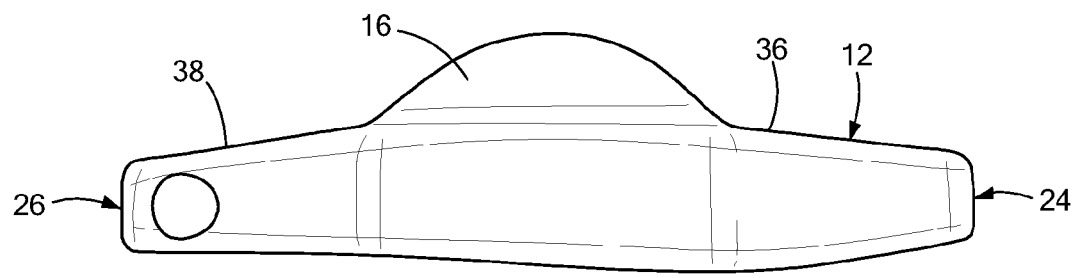
FIG. 17 is a side view of the lower member of a lumbar prosthesis.
Figure 18:
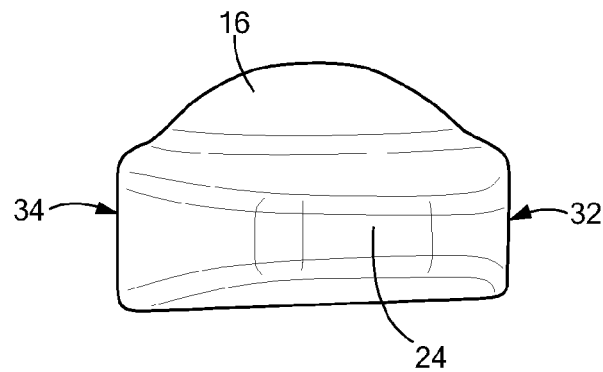
FIGS. 18 and 19 show front views of the lower members of the left and right lumbar prosthesis pairs respectively.
Figure 19:
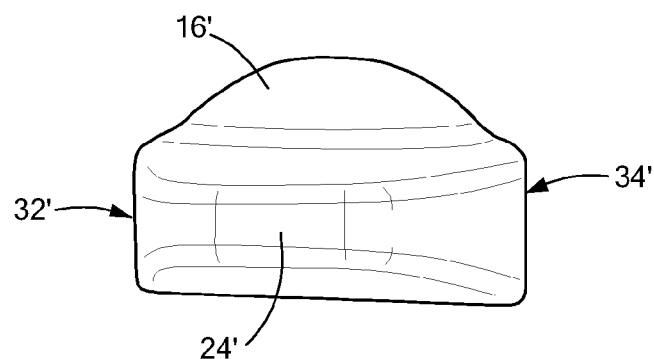
Figure 20:
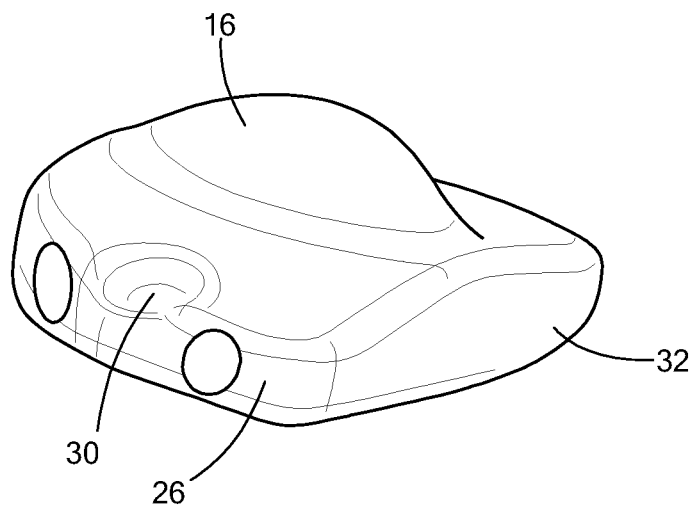
FIGS. 20 and 21 show oblique views of the lower members of the left and right lumbar prosthesis pairs respectively.
Figure 21:
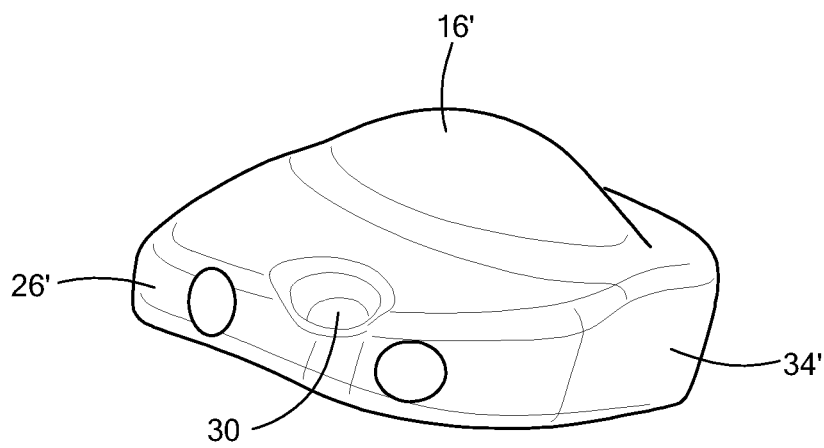

The upper member 4 can also move with respect to lower member 6 through approximately 10 degrees in an anterior direction to allow flexion of the prosthesis, as shown in FIG. 3. Again, due to the nature of inferior surface 10, as upper member goes into flexion there is in an increased distance adjacent posterior end 26 between the upper and lower members 4, 6. This results in a tightening of the annulus posteriorly and serves as a natural block to further flexion.

Referring to FIGS. 13-21, there are shown more detailed views of lower disc prosthesis member 6, 6'. The dome shaped protrusion 16 is located in a central or intermediate section of superior surface 12 in the anterior to posterior plane. The anterior and posterior end sections 36, 38 either side of the dome section 40, as shown by dotted lines 42, are provided at an acute angle to the horizontal sloping downwardly from intermediate section 40 towards ends 24, 26 respectively. The angled surfaces 36, 38 are typically substantially planar in form. This downwards incline is to accommodate the flexion and extension of the upper disc member 4 without impingement therewith. In the medial and lateral plane, protrusion 16 extends substantially the entire distance between the sides of the prosthesis member or from the medial to the lateral edges 32, 34 respectively.

Referring to FIGS. 22-27, there is illustrated more detailed views of upper disc member 4 showing in particular the curvature and complex geometry of the inferior surface 10. The surface 10 is divided into three distinct regions as with the superior surface of lower disc member 6; a substantially central or intermediate section 44 and anterior and posterior end sections 46, 48 respectively. Each section typically occupies approximately one third of the inferior surface.

The central section 44 is substantially curved and forms an asymmetrical inverse dome shaped recess 18. The curvature of the recess in the medial half (i.e. portion adjacent medial edge 32) of the central section differs to the curvature of the recess in the lateral half (i.e. portion adjacent the lateral edge 34) of the central section. More specifically, the medial half of the dome has a curvature corresponding to the arc of a circle having a radius of approximately 15 mm as shown by arrow 50, whereas the lateral half of the dome has a curvature corresponding to the arc of a circle having a radius of approximately 40 mm, as shown by arrow 52 in FIG. 23. Thus, the curvature of the lateral half of the central section corresponds to an arc of a circle having a radius at least double that of the arc of a circle corresponding to the curvature of the medial half of the central section. The purpose of this asymmetry in the medial/lateral plane is to allow capture of the "dome" shaped protrusion 16 of the lower disc member, but still allow some medial and lateral movement of the disc members. This contributes to stability and prevents dislocation of the upper and lower disc members during movement. The shorter curvature of the medial half of the central section relative to the lateral half helps in the medial and lateral movement of the two vertebral bodies on the right and left prosthesis.

Figure 22:
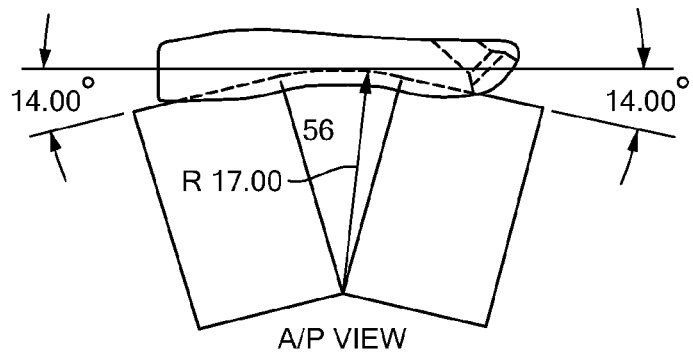
FIG. 22 is a side view of an upper member of a lumbar prosthesis pair to illustrate the angulations and geometry of the inferior surface thereof.
Figure 23:
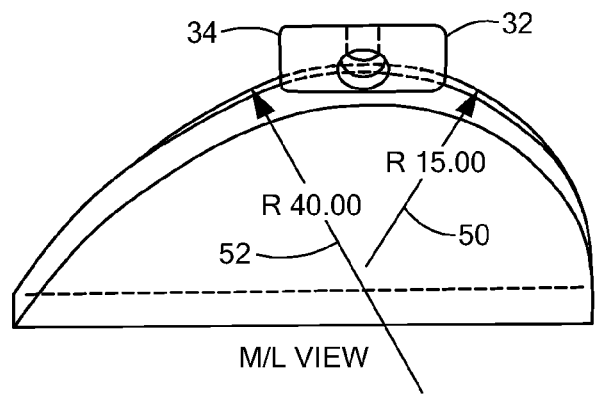
FIG. 23 is a front view of the upper member of the lumbar prosthesis pair to illustrate the radius in the medial and lateral part of the curvature of the inferior surface.
Figure 24:
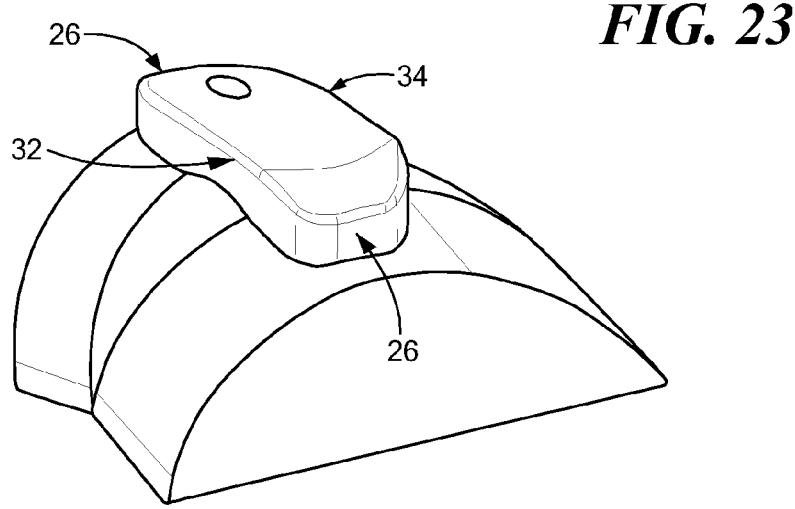
FIG. 24 is an oblique view of the upper member of the lumbar prosthesis pair to further illustrate the shape of the inferior articulating surface thereof.
Figure 25:
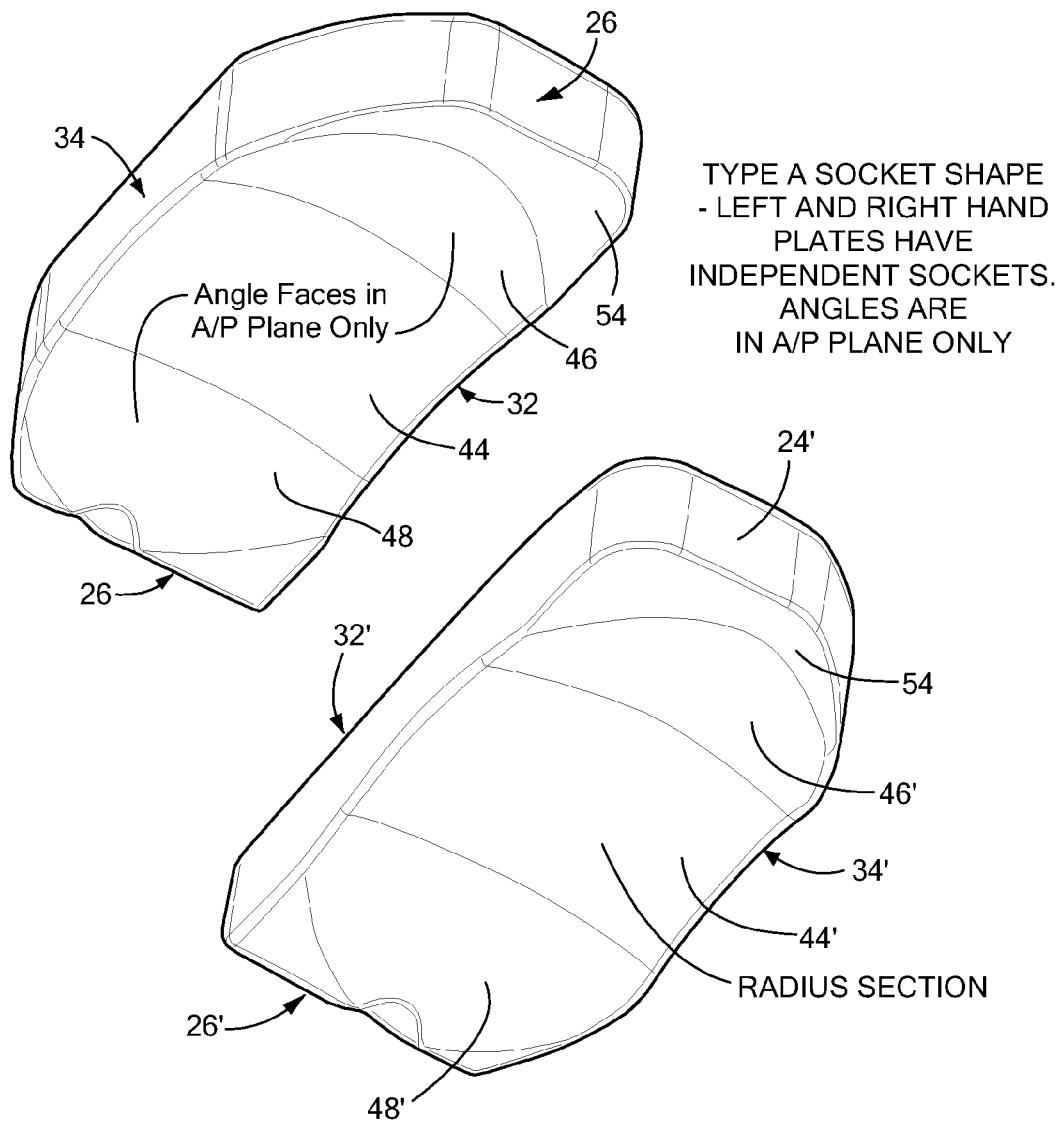
FIG. 25 shows a perspective view of the inferior surface of the upper members of the left and right lumbar prosthesis pairs respectively.
Figure 26A:
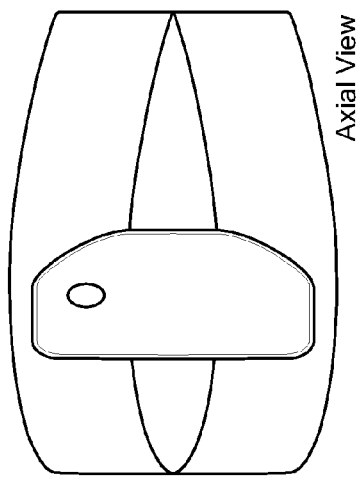
FIGS. 26a-d illustrates a) a solid inverse representation of the recess portion shape on the inferior surface of the upper member of the prosthesis b) an axial view of the prosthesis c) a side view and d) a front view showing the medial/lateral asymmetry of the prosthesis.
Figure 26B:
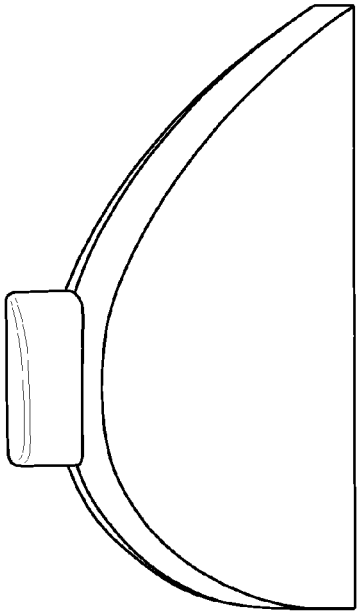
Figure 26C:
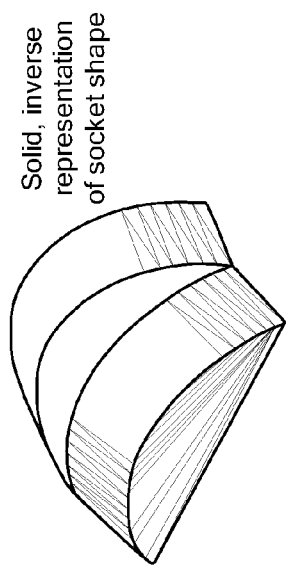
Figure 26D:
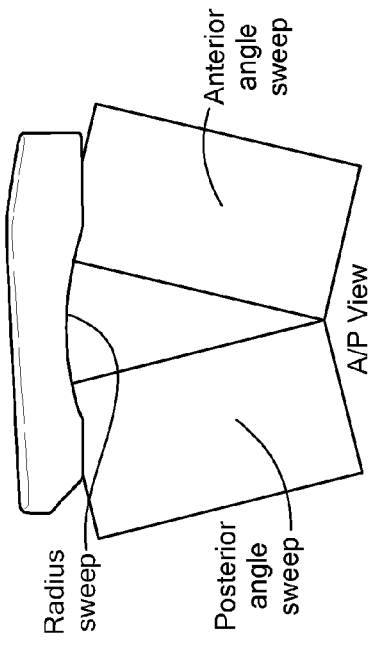
Figure 27:
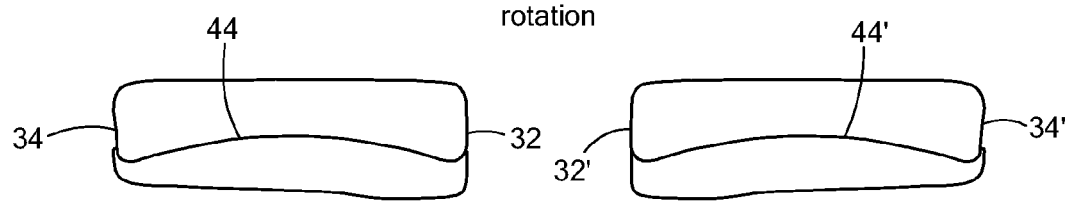
FIG. 27 is a cross section through the upper member of a lumbar prosthesis pair showing the medial lateral curvature of the articulating surface.
Figure 28:
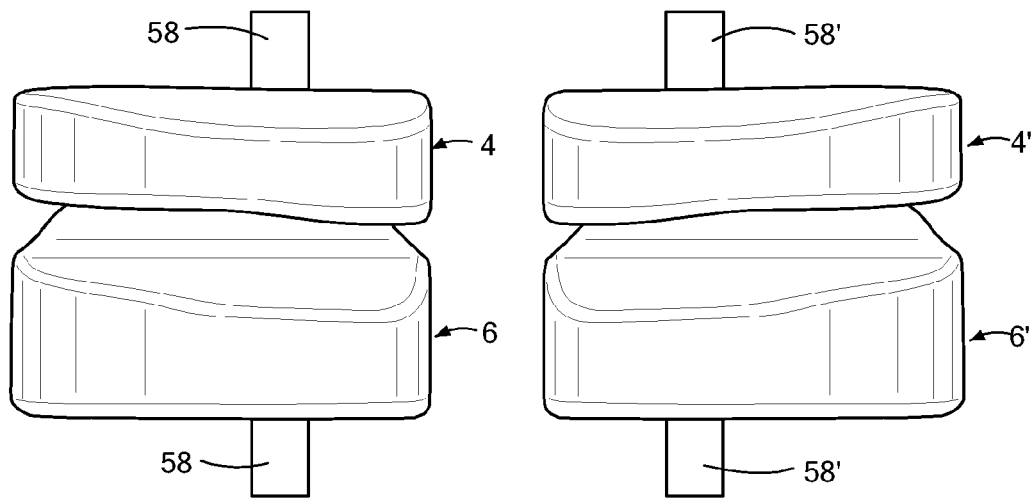
FIG. 28 show front views of the left and right lumbar prosthesis pairs respectively in an alternative embodiment with the screws replaced by fin members.
Figure 29A:
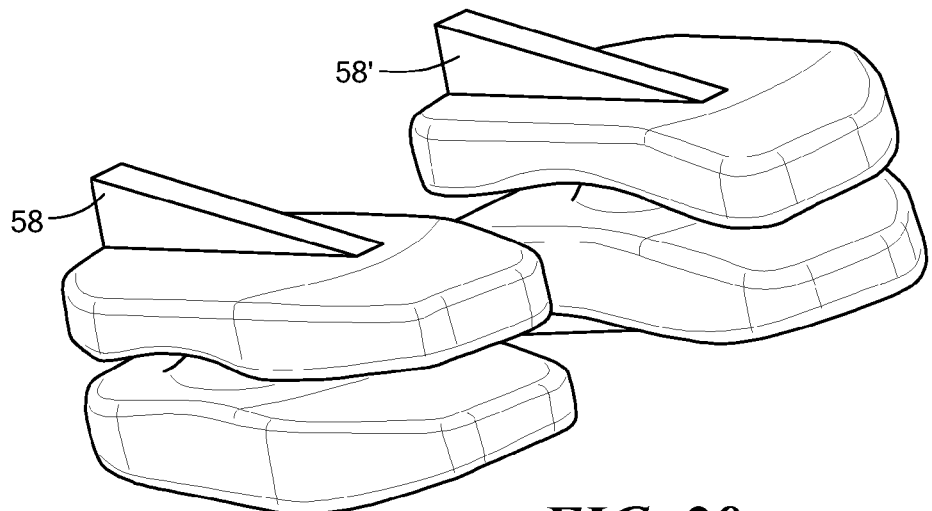
FIGS. 29a and 29b illustrate oblique views of the left and right lumbar prosthesis pairs in FIG. 28 joined together and spaced apart respectively.
Figure 29B:
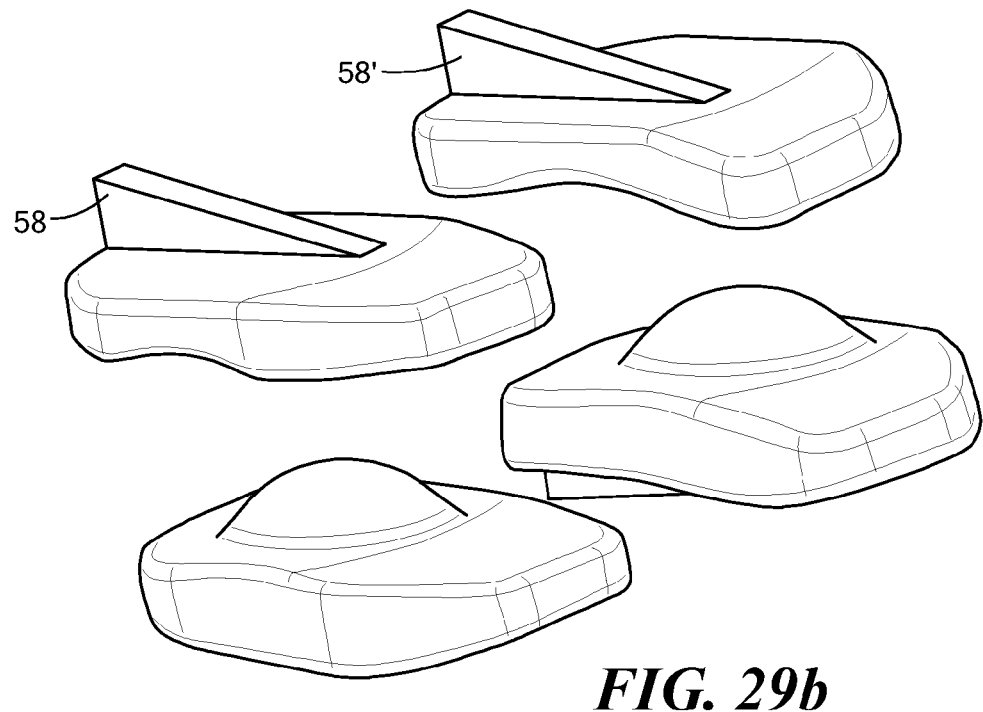
Figure 30A:
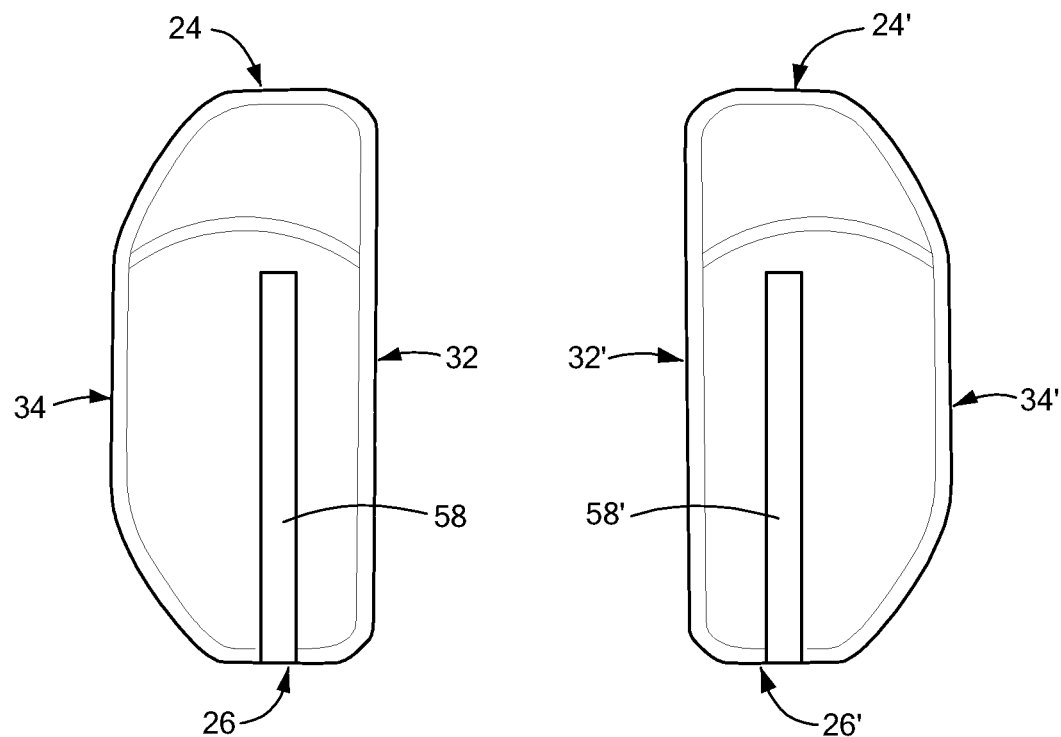
FIGS. 30a-30f show a) superior surfaces of the upper members of the left and right lumbar prosthesis pairs in FIG. 28 b) a side view c) a front view d) a further side view e) inferior surfaces of the lower members of the left and right lumbar prosthesis pairs and f) oblique views of the pairs.
Figure 30B:
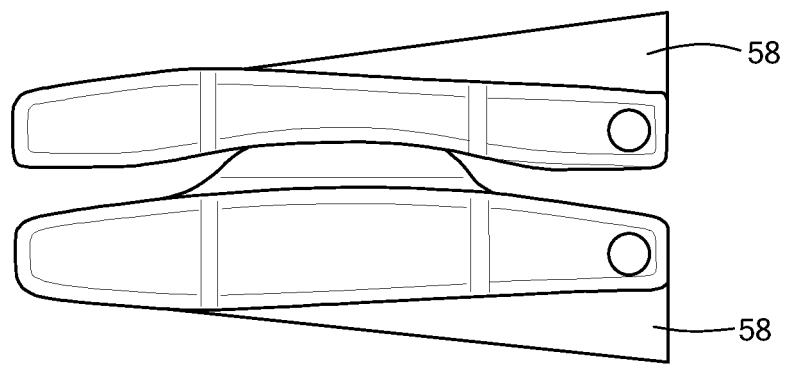
Figure 30C:
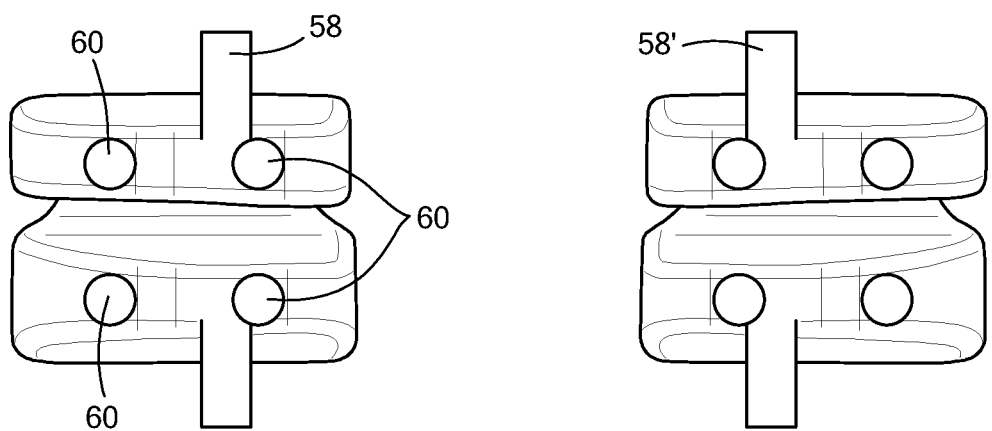
Figure 30D:
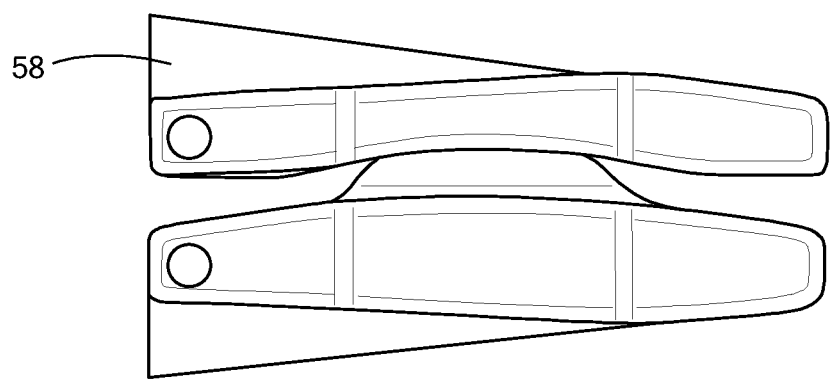
Figure 30E:
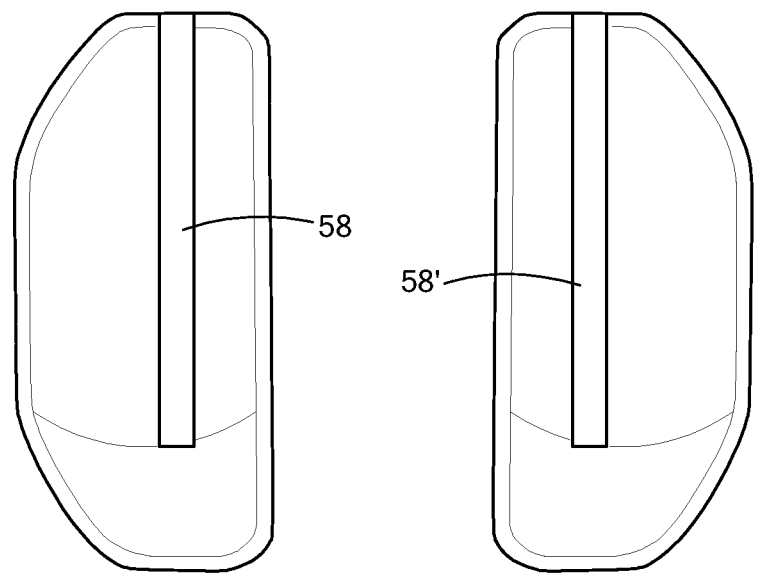
Figure 30F:
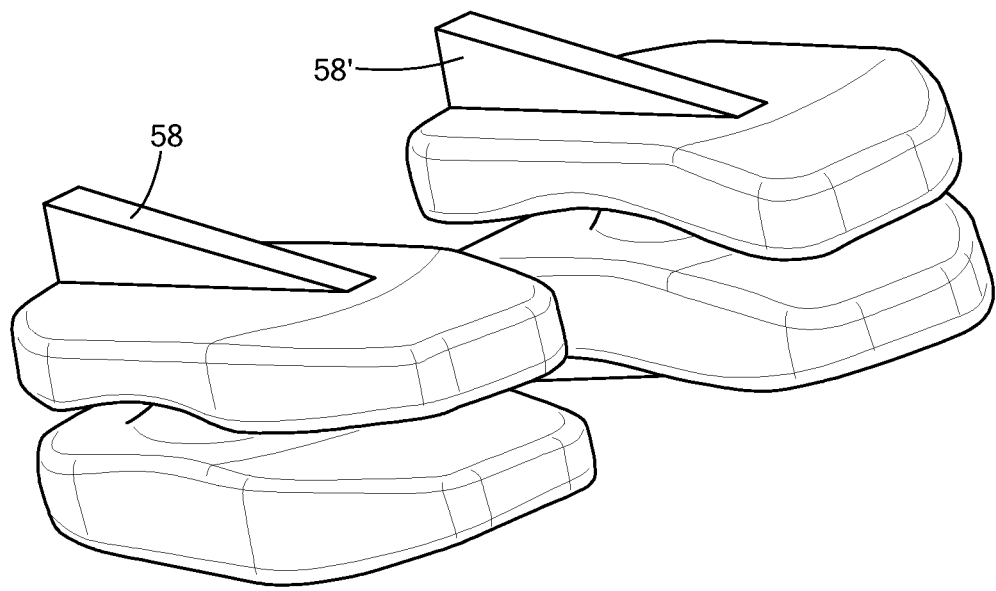
Figure 31:
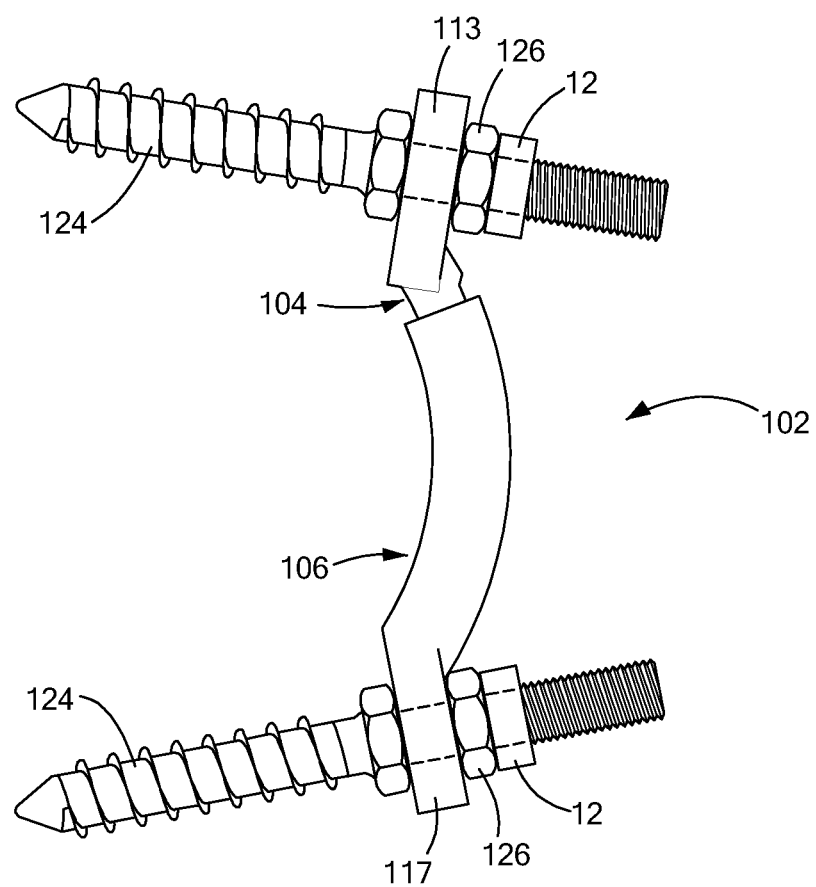
FIG. 31 is a side view of a facet joint replacement prosthesis according to an embodiment of the present invention.
Figure 32:
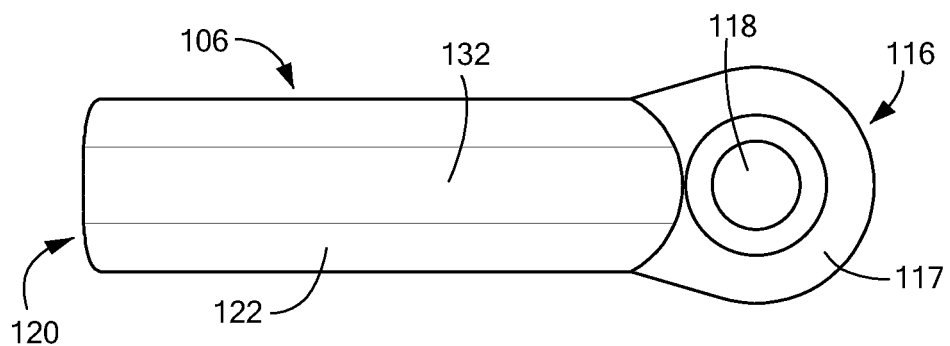
FIGS. 32-36 show a front view, end view, side view, rear view and oblique view respectively of the second or female member of the facet replacement prosthesis.
Figure 33:
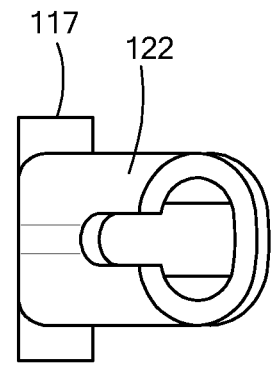
Figure 34:
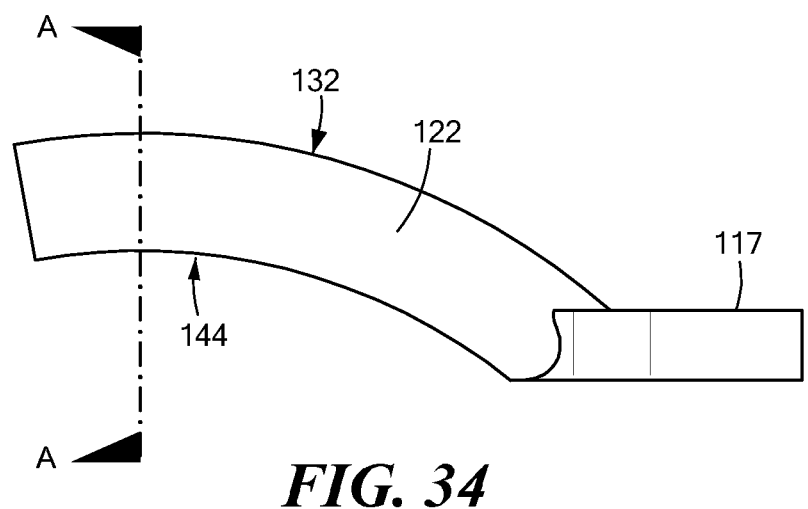
Figure 35:
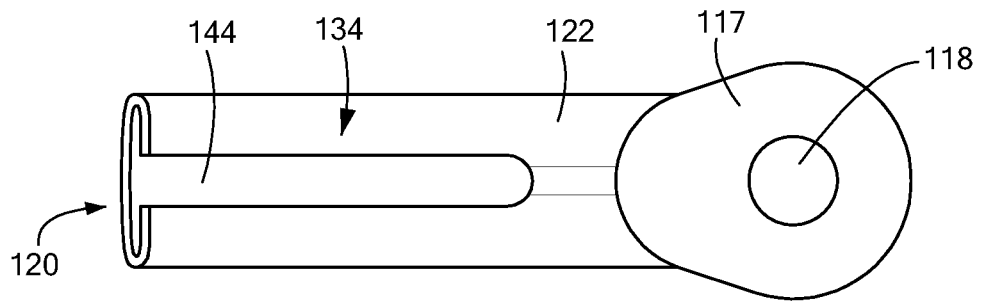
Figure 36:
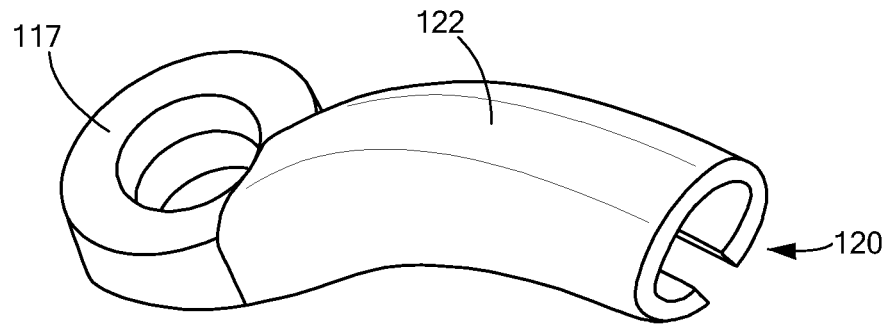
Figure 37:
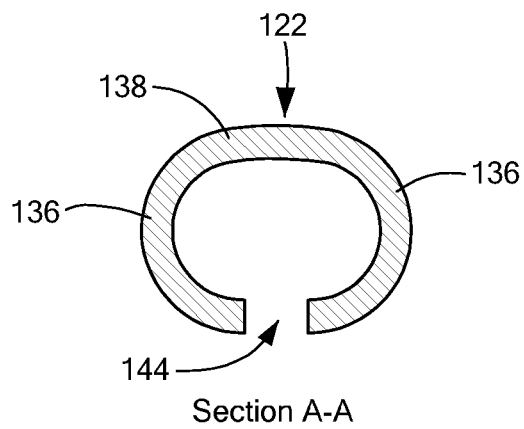
FIG. 37 is a cross sectional view of the second or female member of the facet replacement prosthesis taken along the line marked A-A in FIG. 34.
Figure 38:
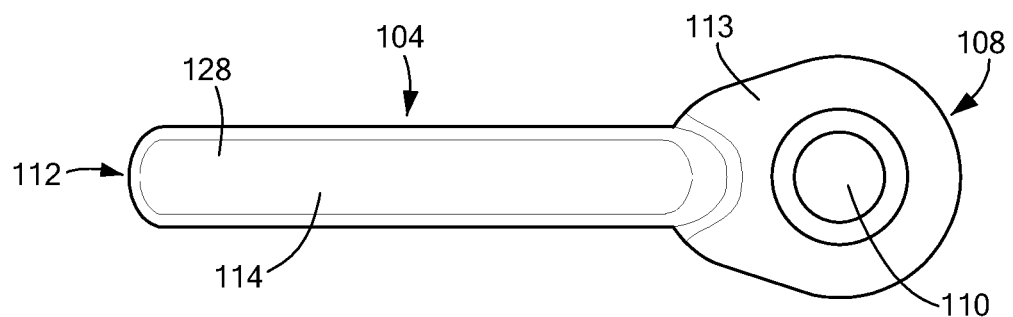
FIGS. 38-42 show a front view, end view, side view, rear view and oblique view respectively of the first or male member of the facet replacement prosthesis.
Figure 39:
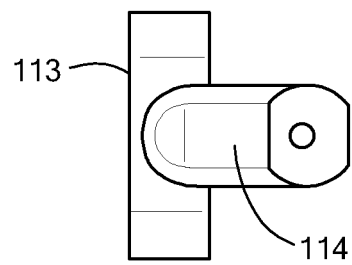
Figure 40:
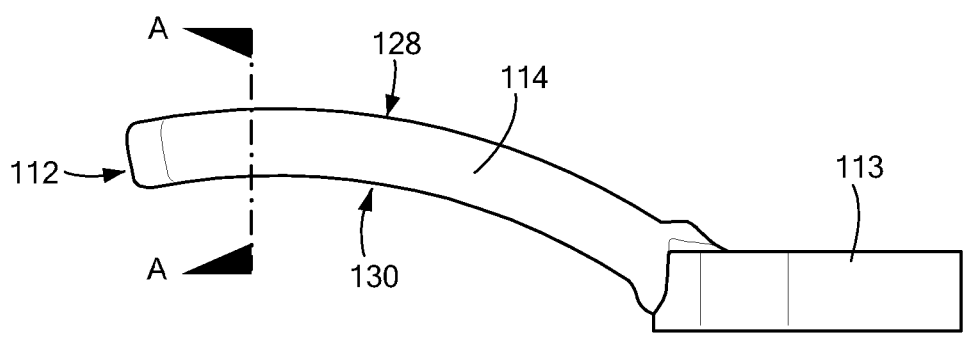
Figure 41:
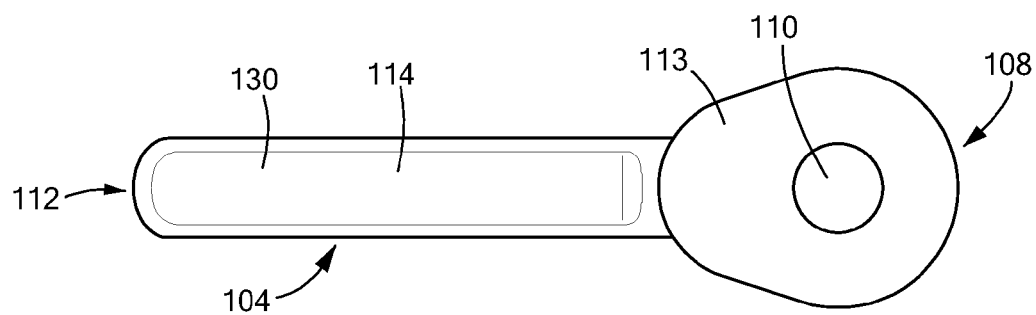
Figure 42:
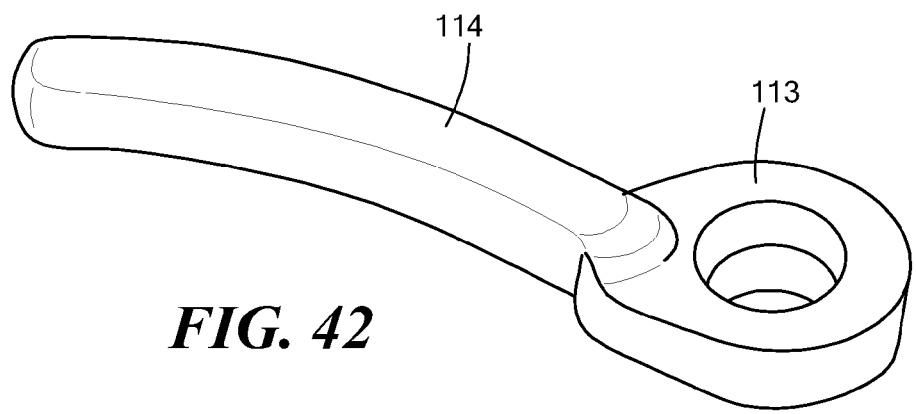
Figure 43:
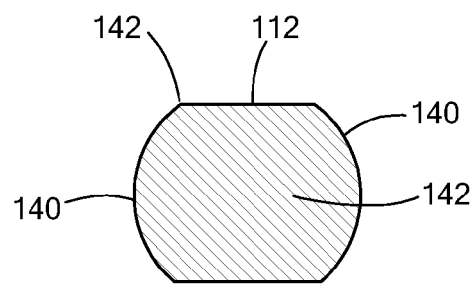
FIG. 43 is a cross sectional view of the first or male member of the facet replacement prosthesis taken along the line marked A-A in FIG. 40.
Figure 44C:
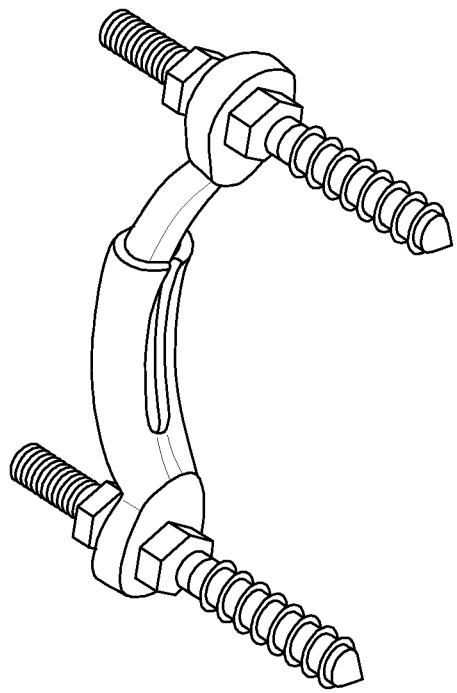
Figure 44D:
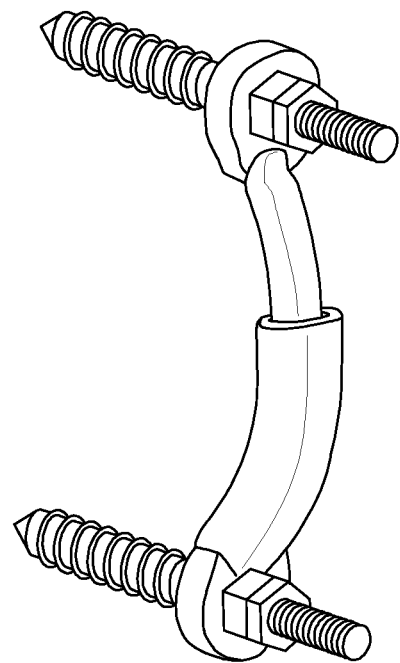
Figure 45A:
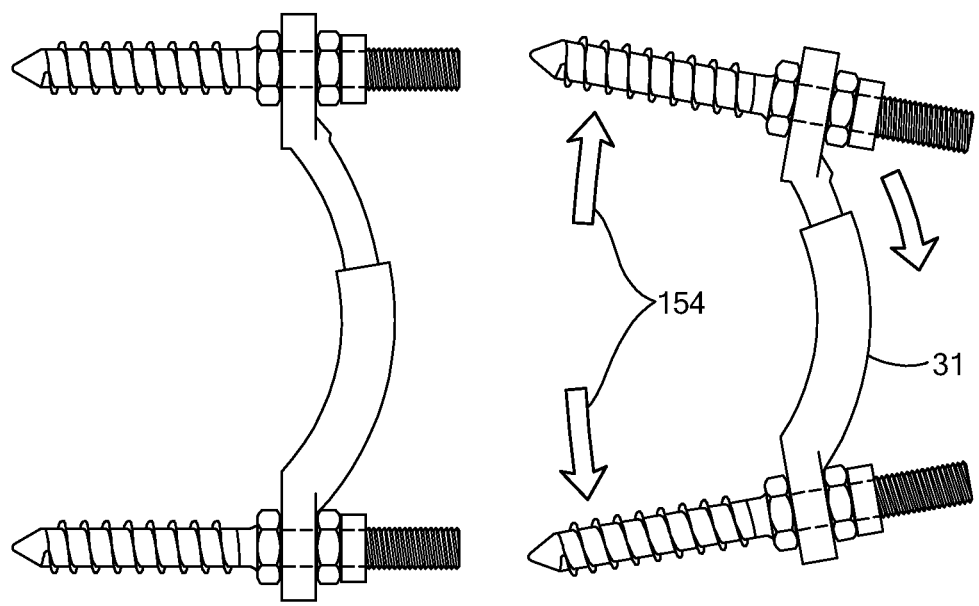
FIGS. 45a and 45b illustrate the ability of the male member to move within the female member and produce a flexion and extension movement of the vertebral body respectively.
Figure 45B:
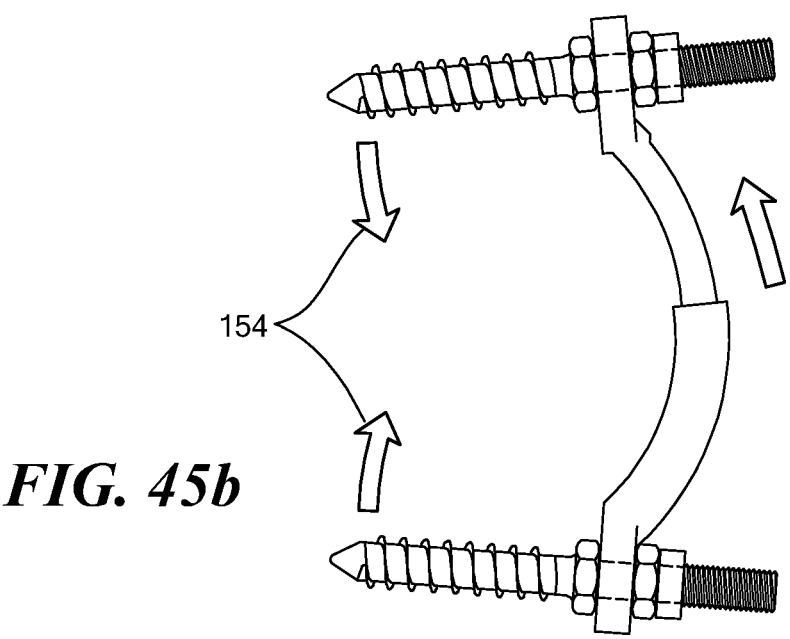
Figure 47:
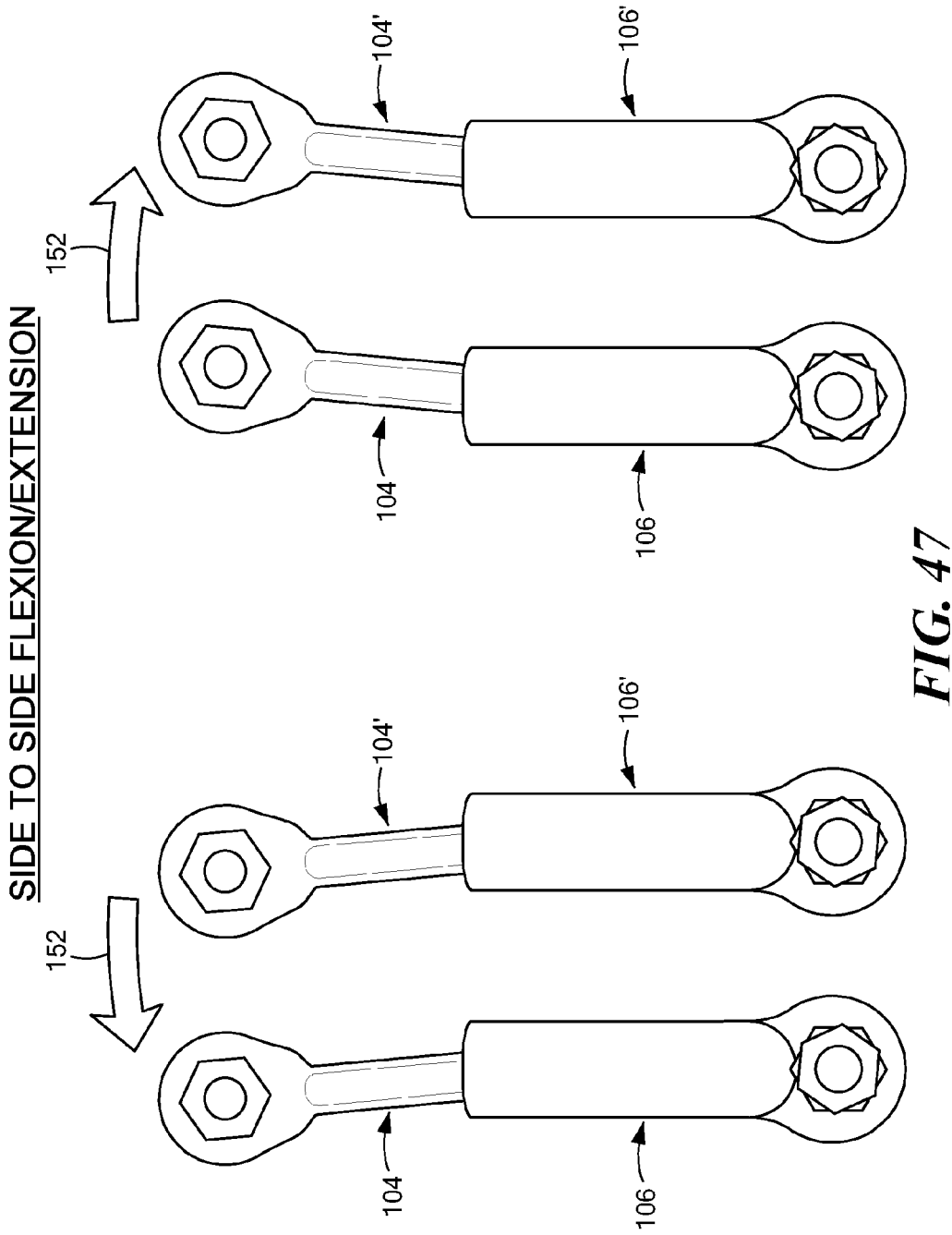
FIG. 47 illustrates front views of the facet replacement prosthesis showing the ability of the male and/or female components to undergo side to side flexion.
Figure 48A:
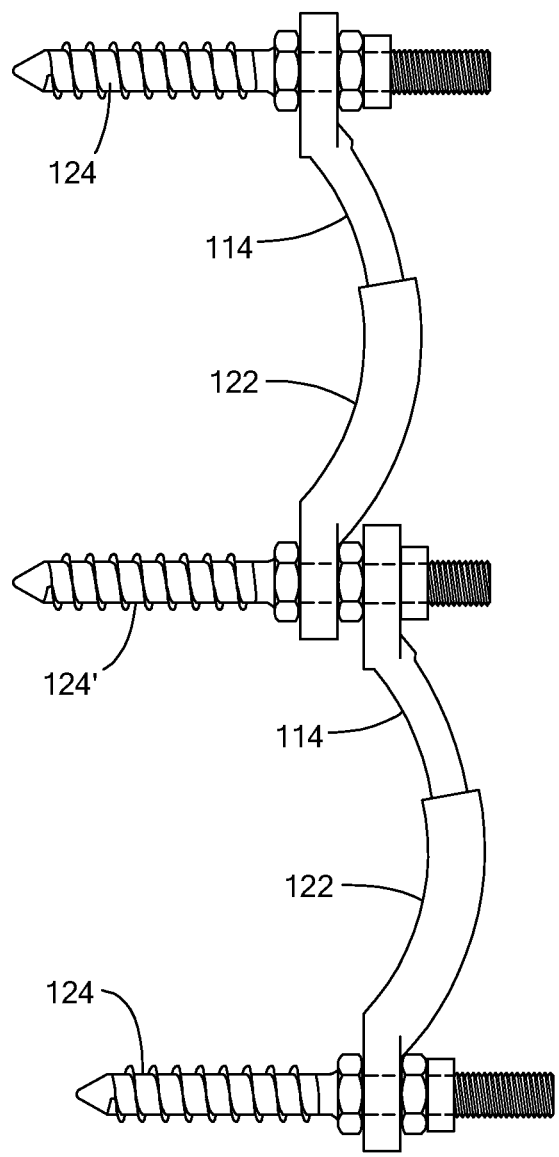
Figure 48B:
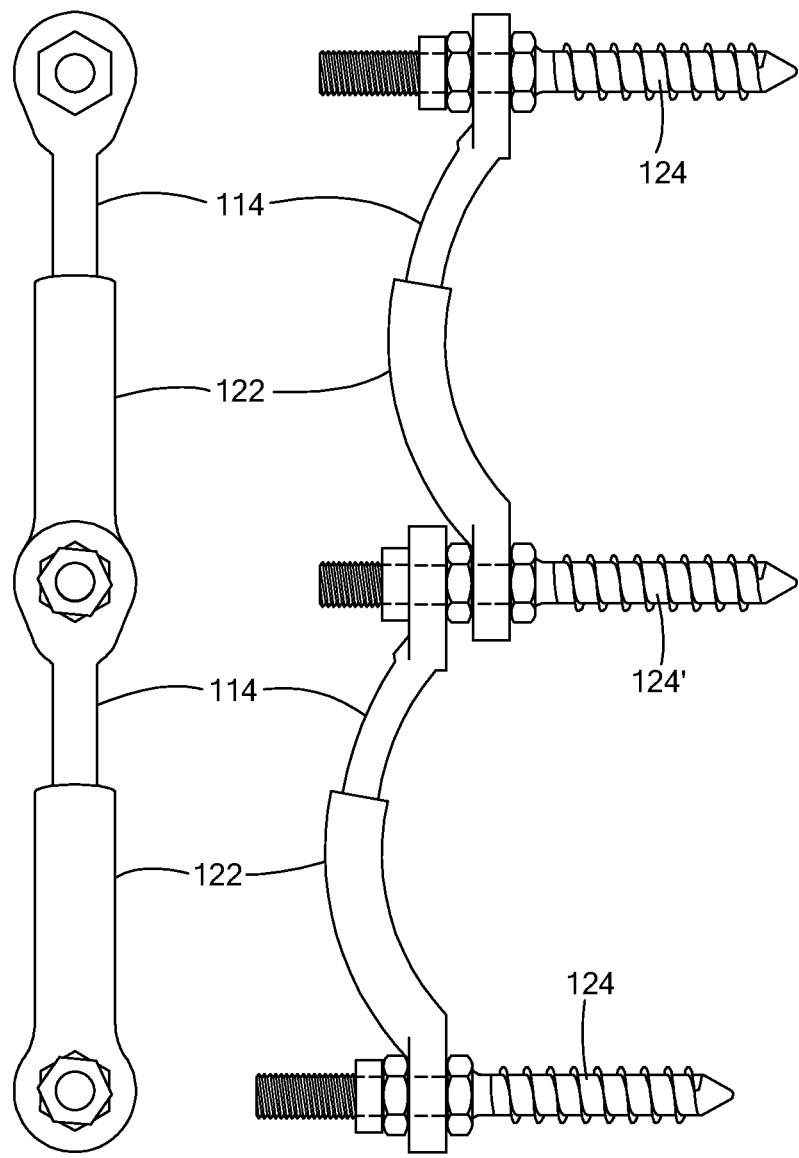

The anterior and posterior end sections 46, 48 are provided at an acute angle to the horizontal, typically approximately 12-14 degrees as shown in FIG. 22, and provide an incline sloping downwardly from the central section 44 to the anterior and posterior ends 24, 26 of the inferior surface respectively. The surface of the anterior and posterior end sections that runs from the central section to the edge of the anterior and posterior sections, as seen in FIG. 25, is generally planar, although a mild curvature or concavity to the surface can be provided. It is to be noted that the slope of the anterior section 46, 46' ends before the anterior end, thereby leaving a small planar surface 54 adjacent anterior end 46, 46'. In the lateral view, the edge of the anterior and posterior surfaces is substantially planar, and does not include a radius, so that the distance between the vertebrae increases in flexion and extension.

The curvature of the central section recess on the anterior to posterior axis corresponds to an arc of a circle having a radius of approximately 17 mm, as shown by arrow 56 in FIG. 22. This is designed so that in combination with the other geometric features of the prosthesis, anterior and posterior movement of the upper disc member is allowed with respect to the lower disc member of approximately 10 degrees, as previously described in relation to FIGS. 2 and 3, even if the prosthesis pairs are not exactly parallel to each other. This geometry is also designed to allow limited sideways (medial/lateral plane) tilt of the upper disc member on the lower disc member, allowing sideways movement of the two disc members on each other, such that the right and the left prosthesis move in tandem.

The geometry of the inferior surface of the upper disc member is also designed to allow limited rotation of the right or left prosthesis pairs. This means that if the upper disc member of the right prosthesis pair moves anteriorly, the upper disc member on the left prosthesis pair moves posteriorly allowing limited rotation of the two vertebral members to occur.

The aim of the surgical procedure for the disc replacement is to insert the left and right prosthesis pairs as parallel to each other as possible within the disc space. However, even if there is medial tilt of between 0-25 degrees between the prosthesis pairs, anterior and posterior movement of the pairs will still be possible and the upper and lower disc members will remain articulated during this movement. Thus, one disc pair is located at one side of the disc space and the other disc pair is located at the opposite side of the disc space (i.e. in the medial lateral plane).

According to a further embodiment of the present invention, alternative attachment means can be provided in the form of fin members 58 on the superior surface 8 of the upper disc member 4 and on the inferior surface 14 of the lower disc member 6, as shown in FIGS. 28-30*f*. Fin members 58 anchor the disc prosthesis to adjacent vertebrae.

Fins 58 are substantially triangular in shape and are provided longitudinally of the prosthesis (i.e. between the posterior and anterior ends) towards the medial edge 32 of the disc members, so as to avoid the exiting nerve root which goes across the disc laterally. More specifically, the fins are located adjacent posterior end 26 and end before the lead in feature 20, 22 at the anterior end to avoid the exiting lumbar nerve root above the disc on the lateral side (i.e. they extend for approximately two-thirds of the disc surface). The fin has a narrowing taper from posterior end 26 towards anterior end 24.

With the disc prosthesis pairs fitted, the upper disc members typically move substantially symmetrically on the lower disc members as the upper vertebral body moves forward on the lower vertebral body. The anterior and posterior translations of these upper disc members are limited by a tightening of the anterior and posterior annulus in flexion and extension. This is designed to reflect the physiological process by which the anterior and posterior annulus tightens in flexion and extension in a normal lumbar disc.

It is to be noted that the end parts of the lateral side 34 of the disc members are curved to accommodate the lateral aspect of the disc space which is similarly curved, thereby allowing better anatomical placement. Thus, the lateral side includes an intermediate substantially straight/linear/planar surface with the end portions either side thereof curving inwardly towards the posterior and anterior ends respectively. The medial side 32 of the disc members is substantially straight/linear/planar.

Apertures 60 are defined in the posterior end 26 of the upper and lower disc members of each prosthesis pair to allow engagement of an insertion tool therewith so that the prosthesis pairs can be inserted into the disc space. Apertures 60 are typically a spaced distance apart and the apertures on the upper disc member are substantially aligned with the apertures on the lower disc member.

According to a yet further embodiment of the present invention, a disc prosthesis 502 is provided including two pairs of disc members, each pair including an upper disc member 504, 504' and a lower disc member 506, 506', as shown in FIGS. 59a-59e. The disc members can include any or any combination of the abovementioned features and some of these features are labelled using the same reference labels as above. In addition, the vertebral endplate contact surface or superior surface 508, 508' of disc members 504, 504' are provided with a convex shaped portion 510, 510' thereon. The shape of the convex shaped portion is substantially complementary to the recess or concave shaped portion to provide an improved fit when the disc prosthesis is located with the vertebral body of an adjacent disc in use.

The height of the convex portion 510, 510' is greater towards the medial side 512 than to the lateral side 514. The longitudinal axis or longest length of the convex portion is along the anterior 516-posterior 518 axis. In addition, the convex portion is closer to the posterior end 518 of the disc than to the anterior end of the disc.

Facet Joint Replacement Prosthesis

Referring to FIGS. 31-52b, there is illustrated facet joint replacement prostheses 102, 202 according to embodiments of the present invention. Facet joint prostheses 102, 202 can be used alone, or in combination with the lumbar disc prosthesis described above to form a single unit system is the prostheses are designed to replace the entire facet joint on both the right and the left side of the vertebrae.

Prosthesis 102 includes a first member or male member 104 and a second member or female member 106. Both male and female members 104, 106 are substantially elongate in form. Male member 104 has a first end 108 with securing means in the form of an aperture 110 defined therein and a second end 112. End 108 is in the form of a flat or planar plate portion 113 and a curved arm portion 114 is provided between this plate portion 113 and end 112. Female member 106 has a first end 116 with securing means in the form of an aperture 118 defined therein and a second end 120. End 116 is in the form of a flat or plate portion 117 and a curved channel portion 122 is provided between this plate portion 117 and end 120.

Figure 50:
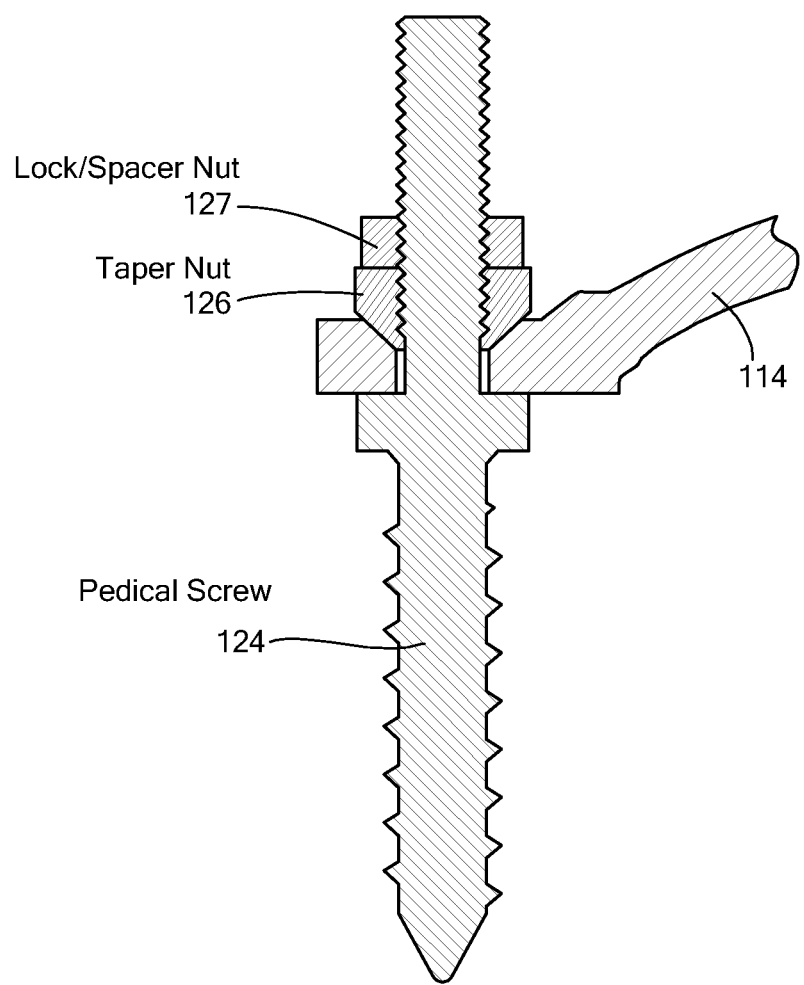
FIG. 50 is a cross sectional view taken through a pedicle screw attached to a female member of a facet joint prosthesis.

The facet prosthesis 102 is inserted by removing the entire existing facet joint and placing pedicle screws 124 into the vertebral body above and below the disc. End 112 of male member 104 is inserted into end 120 of channel 122 of female member 106 and the ends of the pedicle screws 123 are threaded through apertures 118 and 110 and secured with a nut 126. The edge of plate portions 113 and 117 which define apertures 118 and 110 are tapered inwardly so as to allow a good fit with a tapered or conical shaped locking nut 126, as shown in FIG. 50. A further spacing or locking nut 127 can also be provided.

Male member 104 has a rear or posterior 128 and a front or anterior surface 130. The anterior surface 130 of arm portion 114 is typically substantially concave in shape and the posterior surface 128 of arm portion 114 is typically substantially convex in shape. As such, when member 104 is fitted to pedicle screw 124 in use, anterior surface 130 typically faces the vertebrae to which it is to be attached.

Female member 106 has a rear or posterior surface 132 and a front or anterior surface 134. The anterior surface 134 of channel portion 122 is typically substantially concave in shape and the posterior surface of channel portion 122 is typically substantially convex in shape. As such, when member 106 is fitted to pedicel screw 124 in use, anterior surface 134 typically faces the vertebrae to which it is to be attached.

Thus, with the female member interconnected to the male member, the prosthesis curves outwardly from the vertebrae and outwardly of the plate portions 117 and 113. Arm portion 114 of male member 104 is freely slidable or movable in channel portion 122 of female member 106. The curvature of the male and female members is substantially the same. The male member 104 is of slightly smaller dimensions than the interior dimensions of channel portion 122, such that there is a small gap therebetween to allow some sideways movement, as shown by arrows 150 in FIG. 47, and rotation of the male member in the female member, as shown by arrows 152 in FIG. 46. The male member can also move longitudinally in the female member to allow flexion and extension of the prosthesis and thus the vertebral body, as shown by arrows 154 in FIGS. 45a and 45b.

Figure 49:
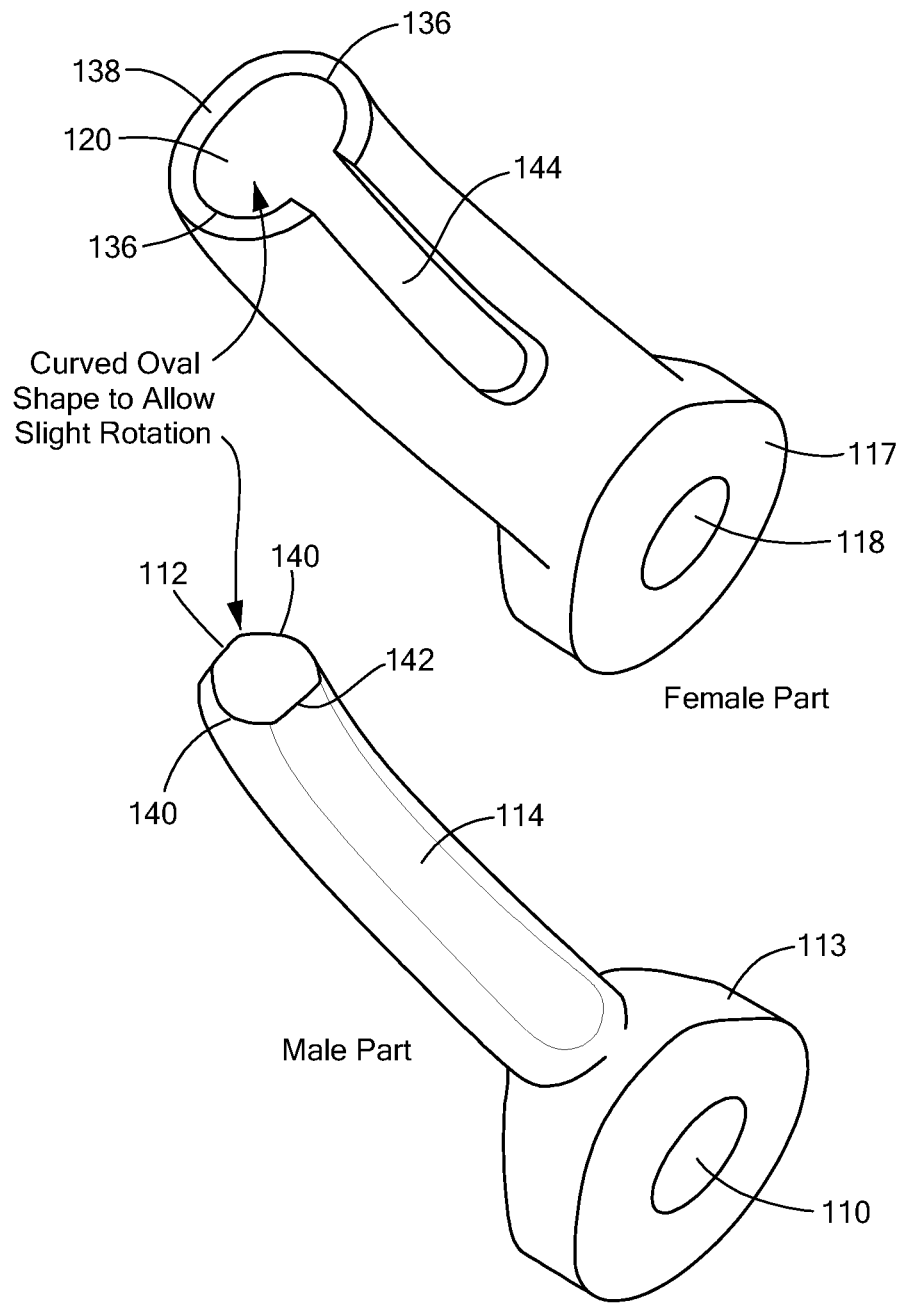
FIG. 49 is an enlarged view of the ends of the female and male members of the facet joint prosthesis.

End 120 of channel portion 122 has curved ends 136 and straight side walls 138 or side walls of less curvature than said curved ends to form a flattened oval shape, as shown in FIG. 49. Preferably side walls 138 form part of an arc, the radius of which is larger than for the arc of the curved ends 136. End 112 of arm portion 114 is substantially complementary in shape to end 120 having curved ends 140 and straight sidewalls 142 or side walls of less curvature than said curved ends. Preferably side walls 142 form part of an arc, the radius of which is larger than for the arc of the curved ends 140. The provision of the shaped ends allows a small degree of rotation of the male component in the female component.

The anterior surface 134 of channel portion 122 has a slot 144 provided longitudinally thereof. Slot 144 is of such a width that the channel portion encloses approximately 70% of the male member 104 when interconnected therewith and is provided to allow some lateral flexion and/or extension and rotation between the male and female members.

A left and right pair of facet joint prostheses are located between the disc on each side thereof. It is irrelevant whether the female or the male member is uppermost and thus the position of the members is interchangeable. In addition, the facet prosthesis can be used at two adjacent levels, and anchor into pedicle screws, as seen in FIGS. 48a-48d. A middle pedicle screw 124' can be used to accommodate two plate portions of the male and/or female members to form a stack. Any number of members can be attached to a pedicle screw as required.

The prosthesis can be formed from any suitable material, such as for example, stainless steel, ceramics, titanium, carbide or other suitable metal alloys. The surface of the prosthesis can be provided slightly roughened so as to increase bonding of the same with bone and/or one or more surface coatings can be provided thereon, such as for example, hyroxyapitite or plasma spray.

Figure 51:
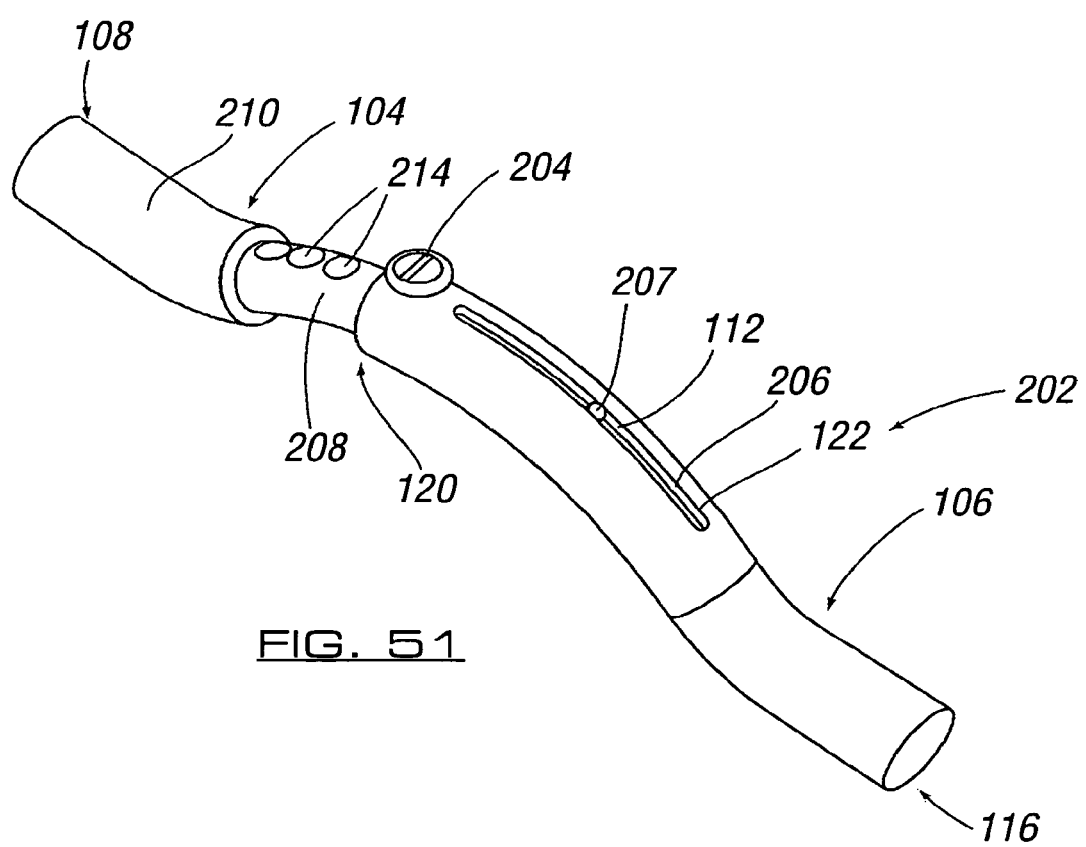
FIG. 51 is a perspective view of a facet joint replacement prosthesis according to a further embodiment of the present invention.
Figure 52A:
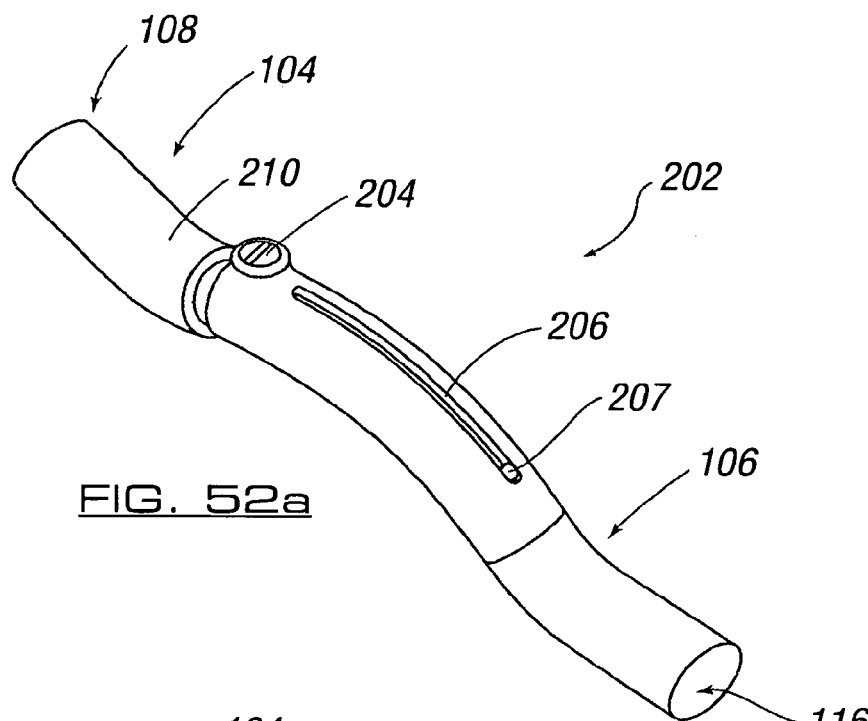
FIGS. 52a and 52b show perspective views of the facet joint prosthesis in FIG. 51 in a retracted and extended position respectively.
Figure 52B:
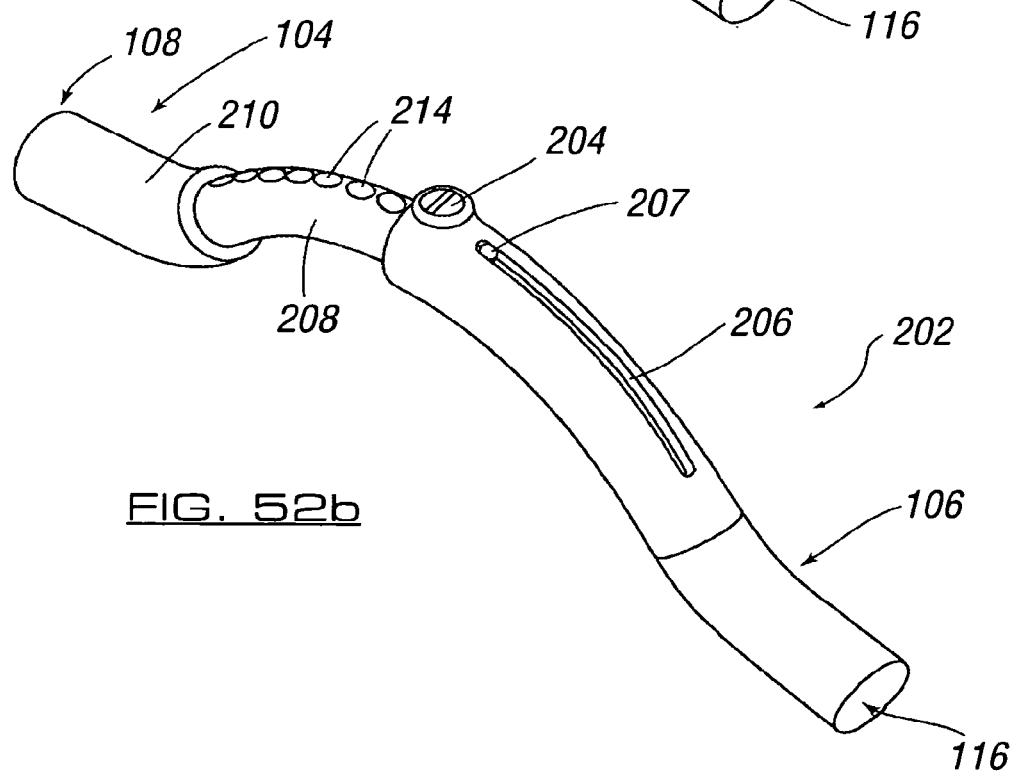
Figure 53A:
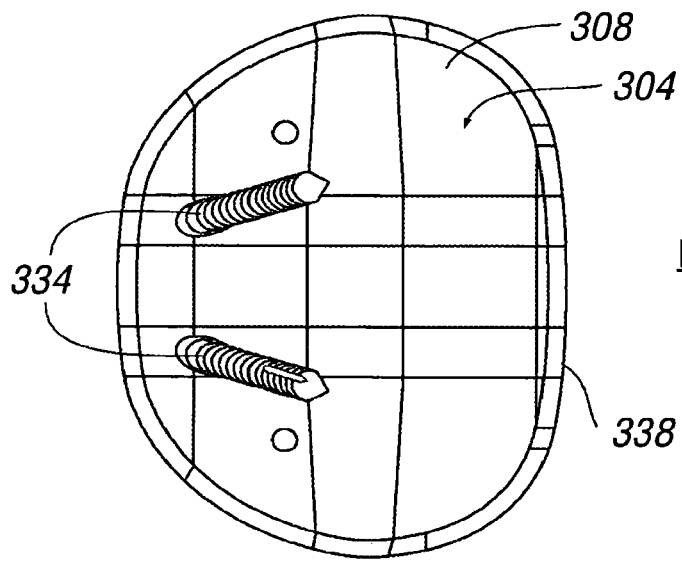
Figure 53B:
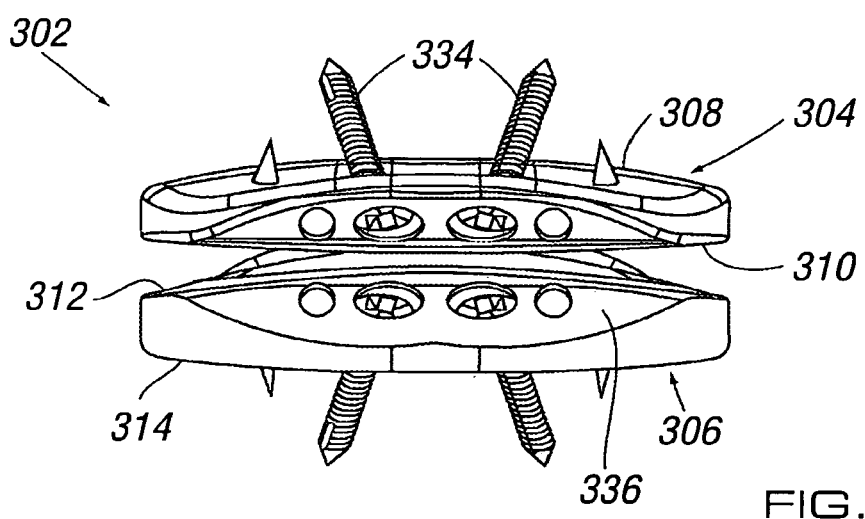
Figure 53C:
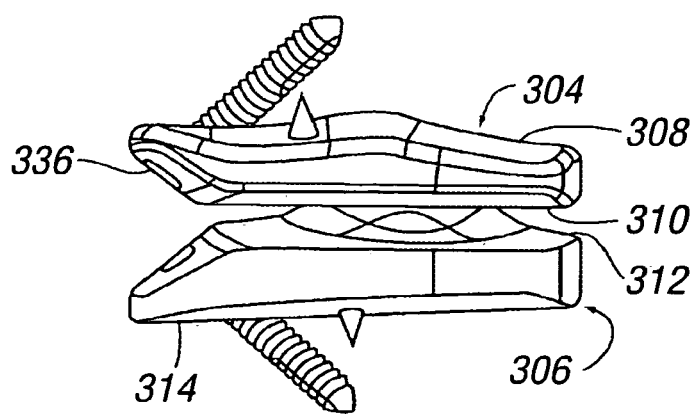
Figure 53D:
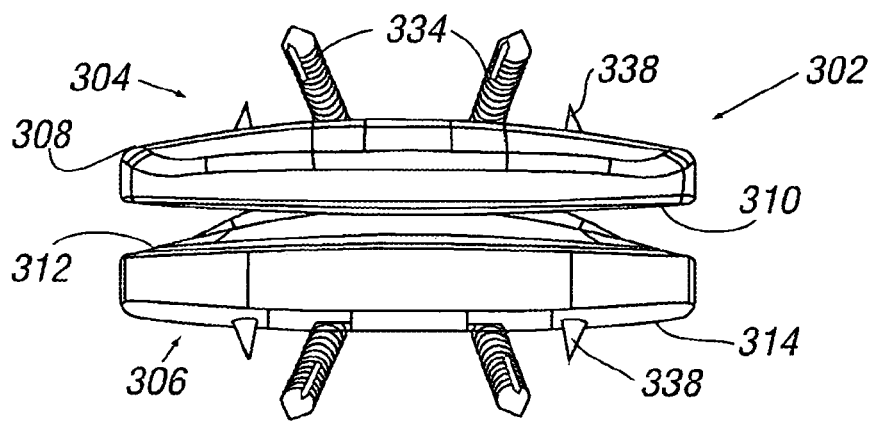
Figure 53E:
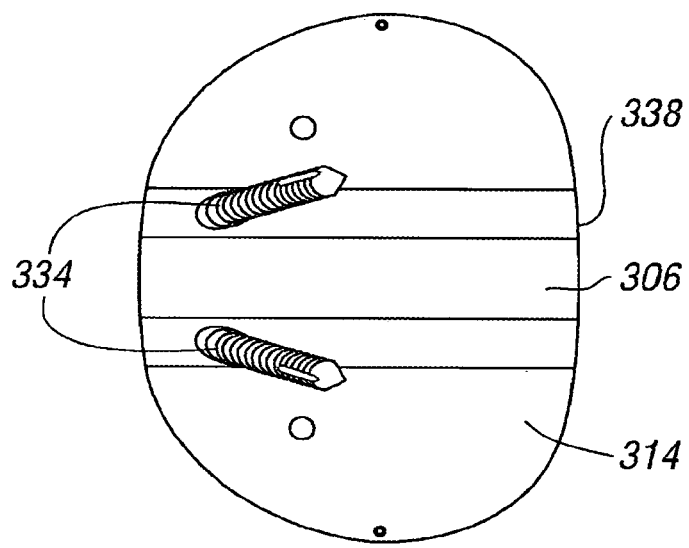
Figure 53F:
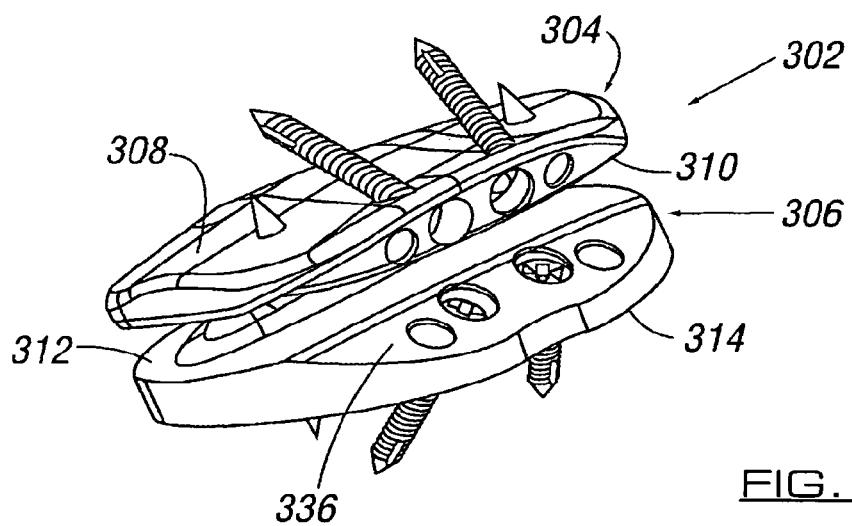
Figure 54A:
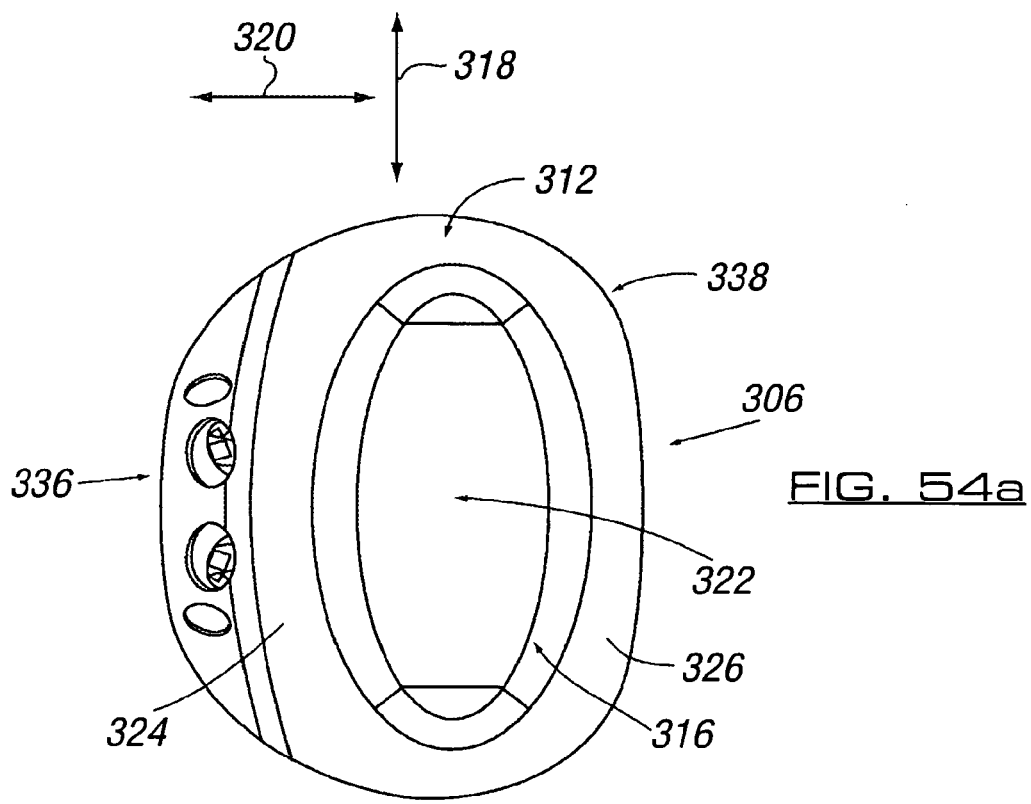
FIGS. 54a-54f show the lower disc member in FIGS. 53a-53f, particularly a top view, anterior view, side view, posterior view, base view and perspective view respectively.
Figure 54B:
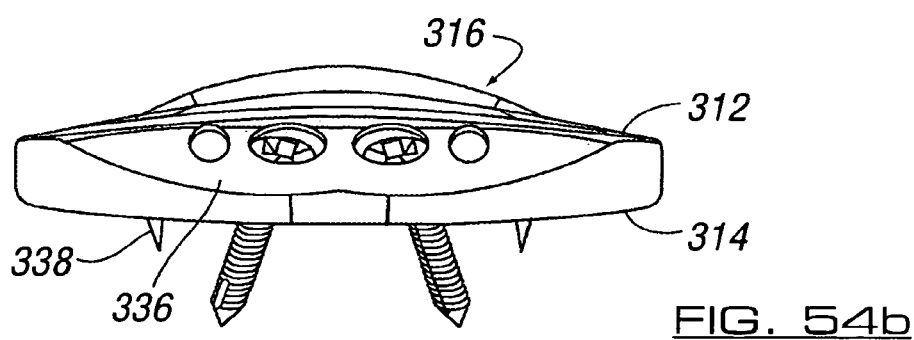
Figure 54C:
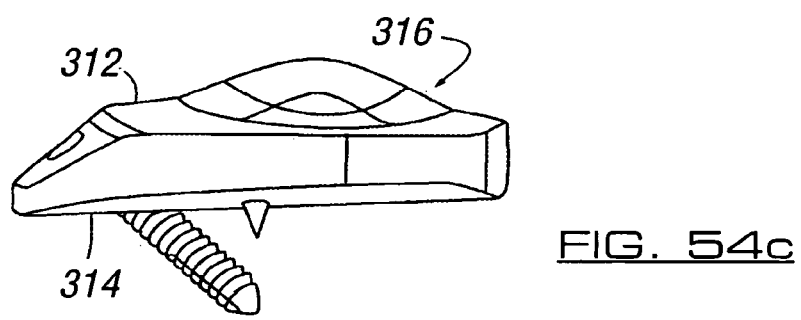
Figure 54D:
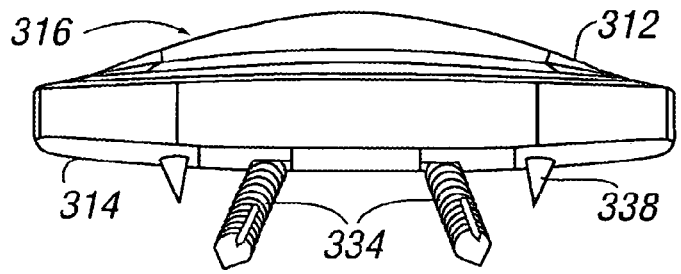
Figure 54E:
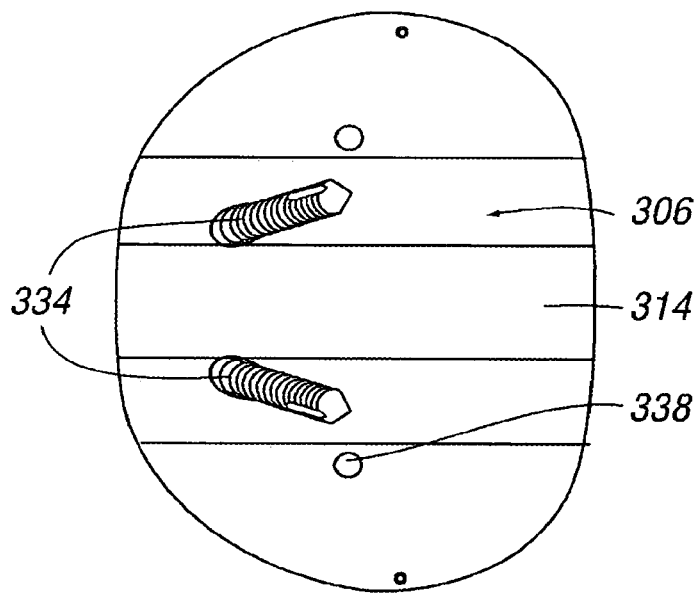
Figure 54F:
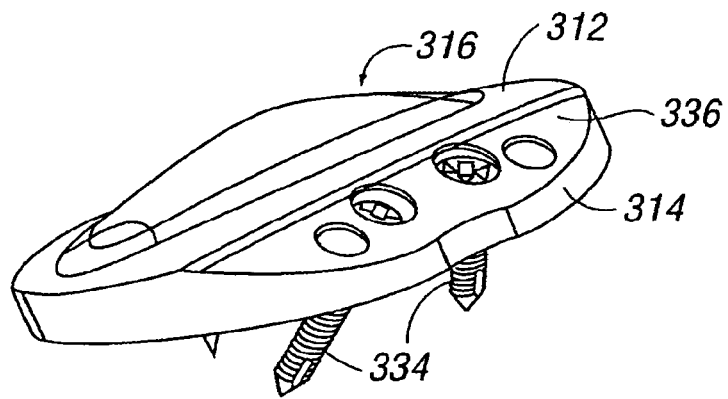
Figure 55A:
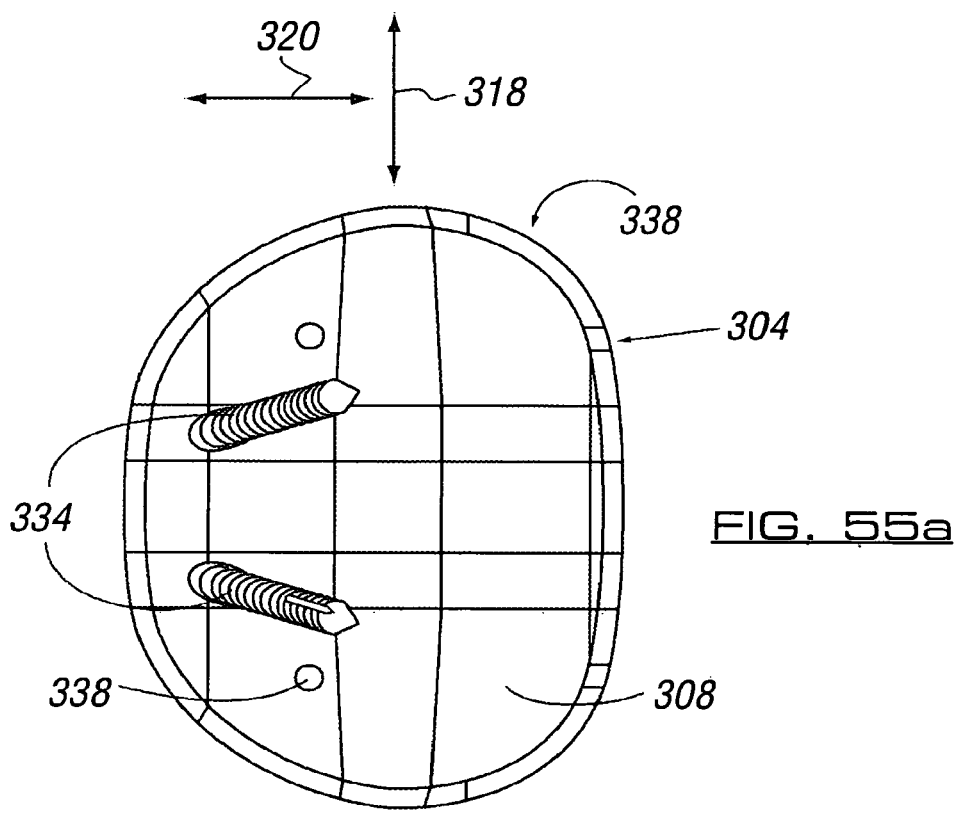
FIGS. 55a-55f show the upper disc member in FIGS. 53a-53f, particularly a top view, anterior view, side view, posterior view, base view and perspective view respectively.
Figure 55B:
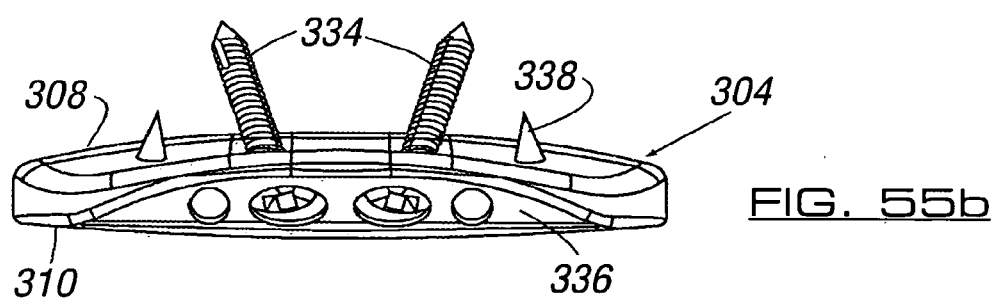
Figure 55C:
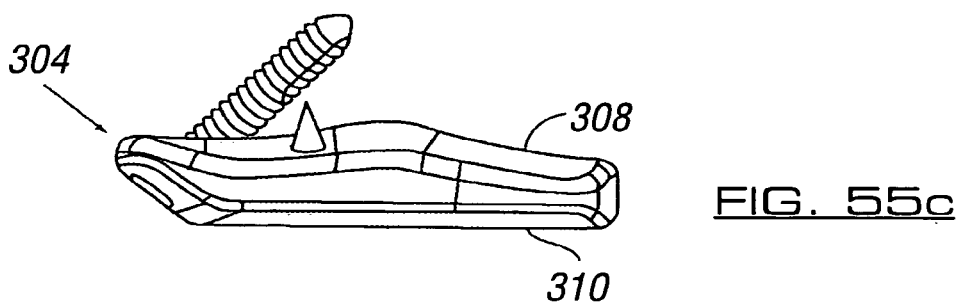
Figure 55D:
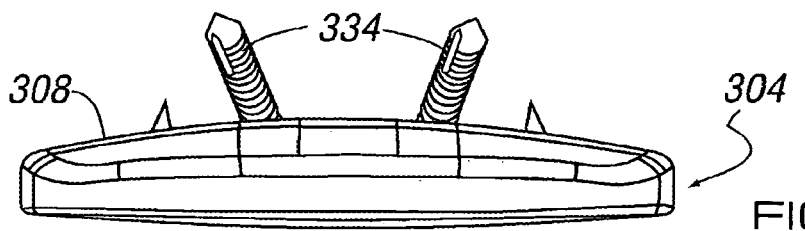
Figure 55E:
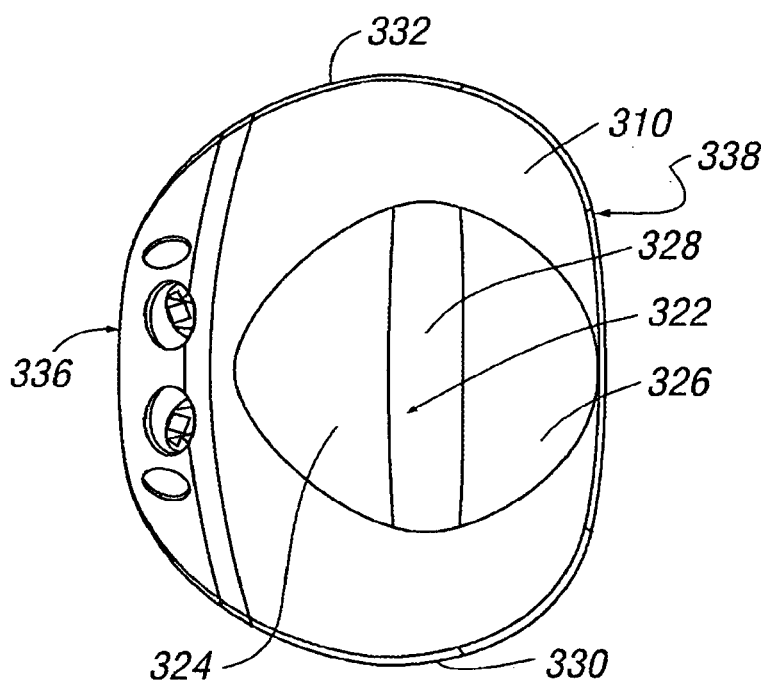
Figure 55F:
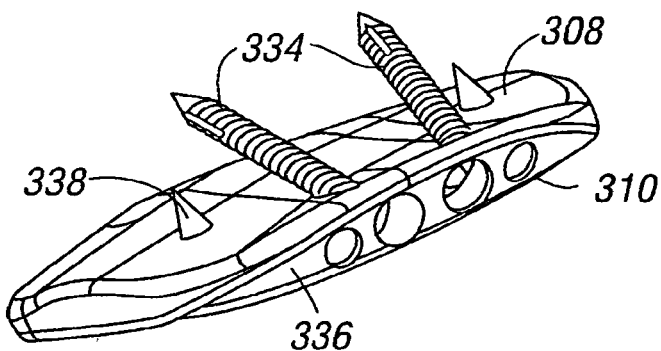
Figure 56D:
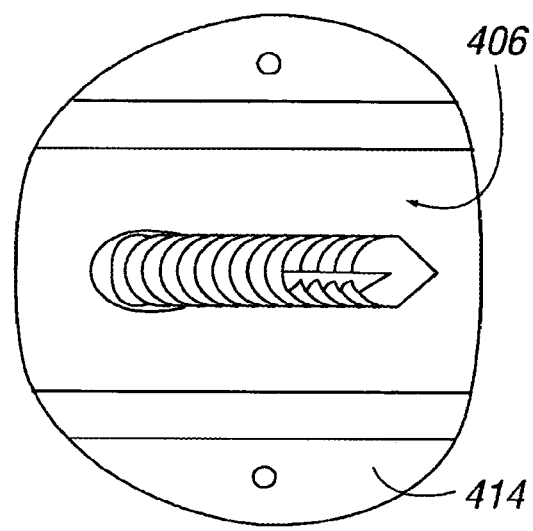
Figure 56E:
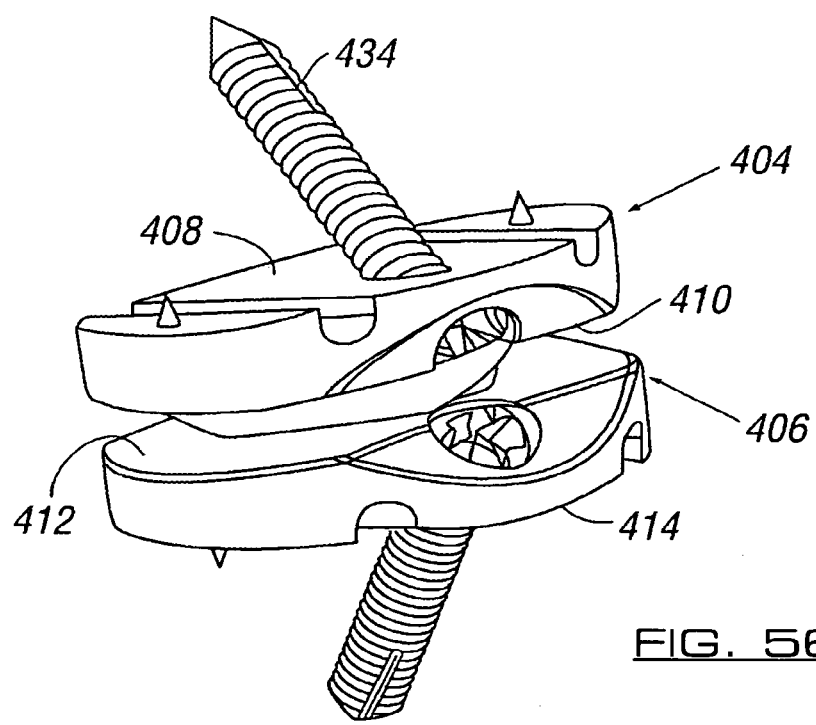
Figure 57A:
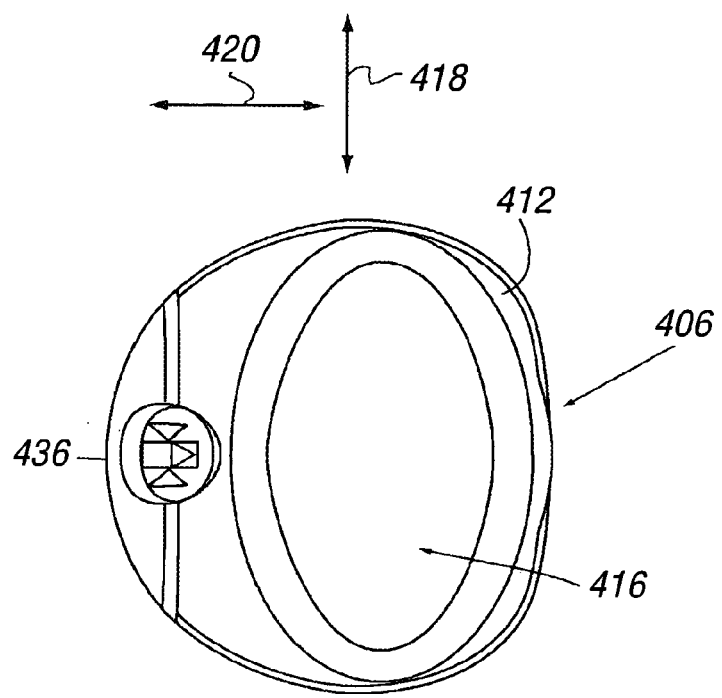
FIGS. 57a-57e show the lower disc member in FIGS. 56a-56e, particularly a top view, anterior view, side view, posterior view, base view and perspective view respectively.
Figure 57B:
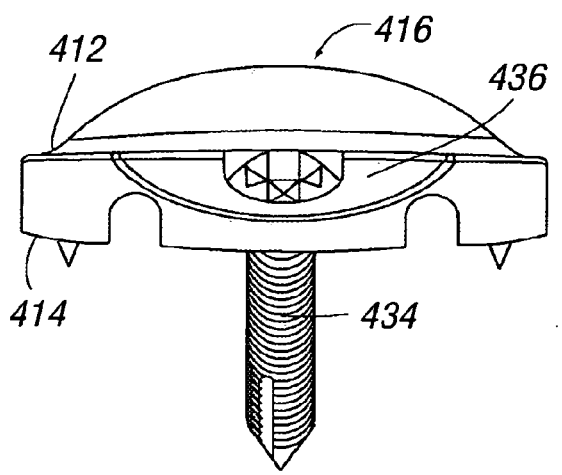
Figure 57C:
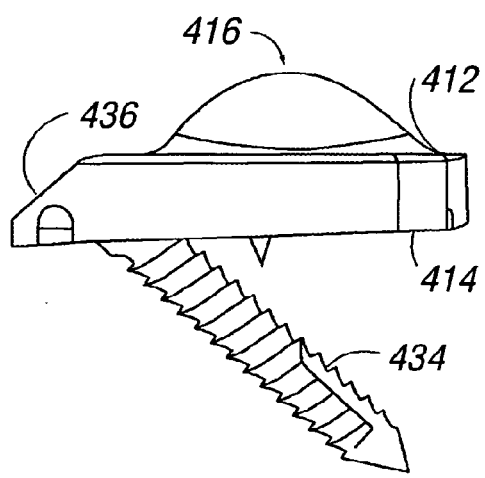
Figure 57D:
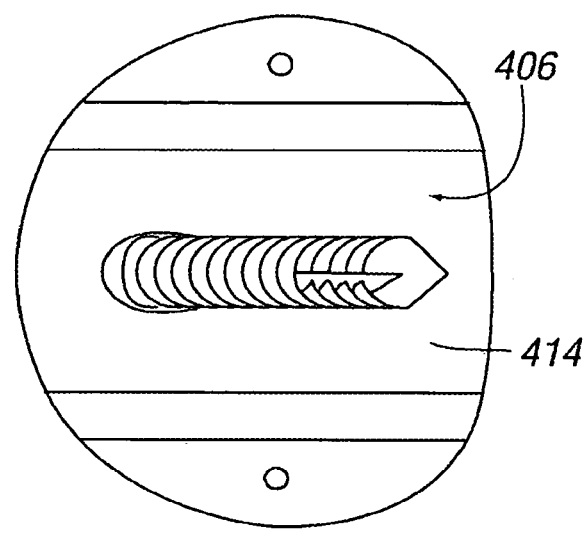
Figure 57E:
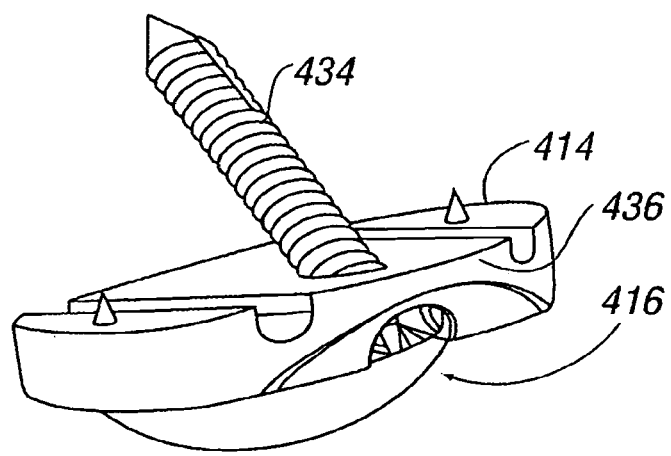
Figure 58A:
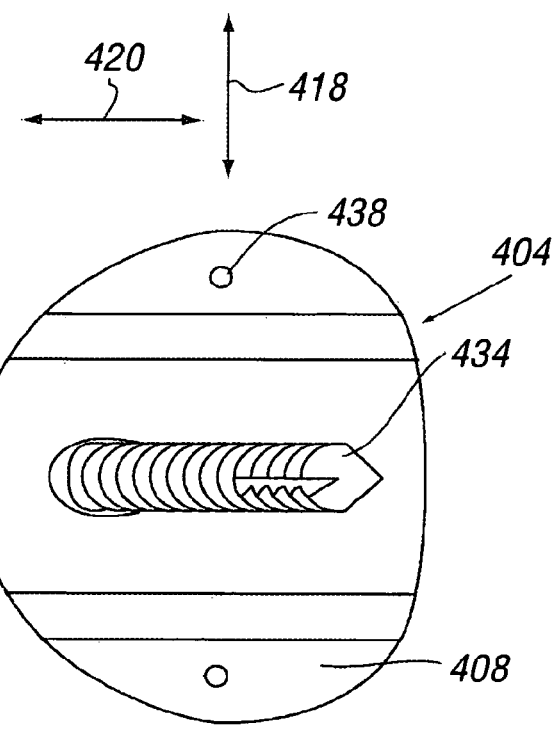
Figures 58B, 58C:
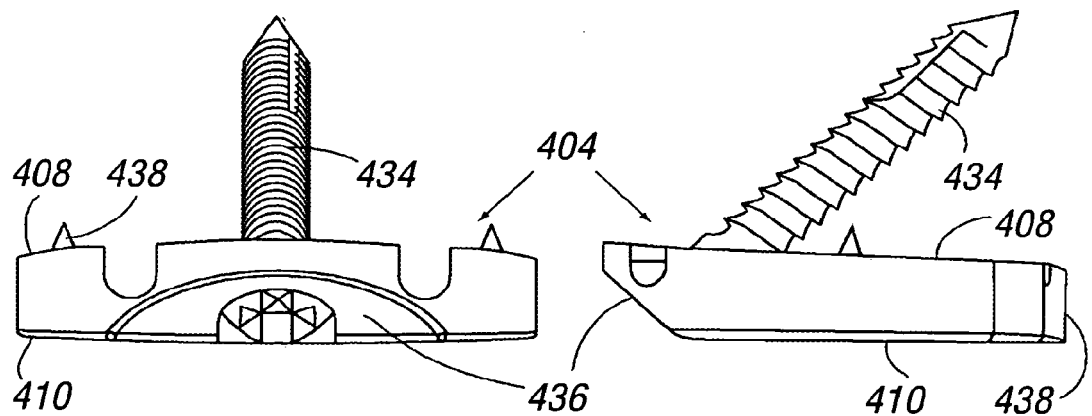
Figure 58D:
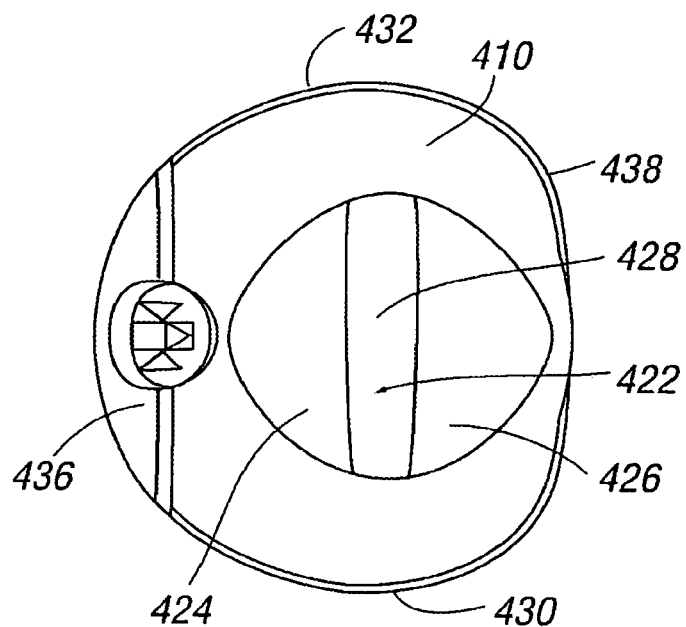
Figure 58E:
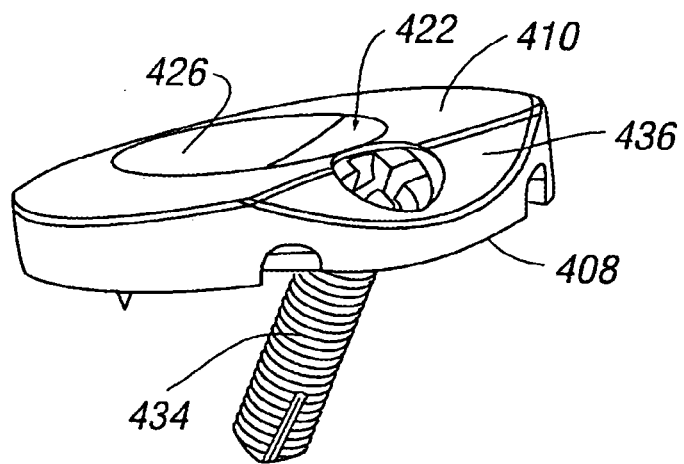
Figure 59A:
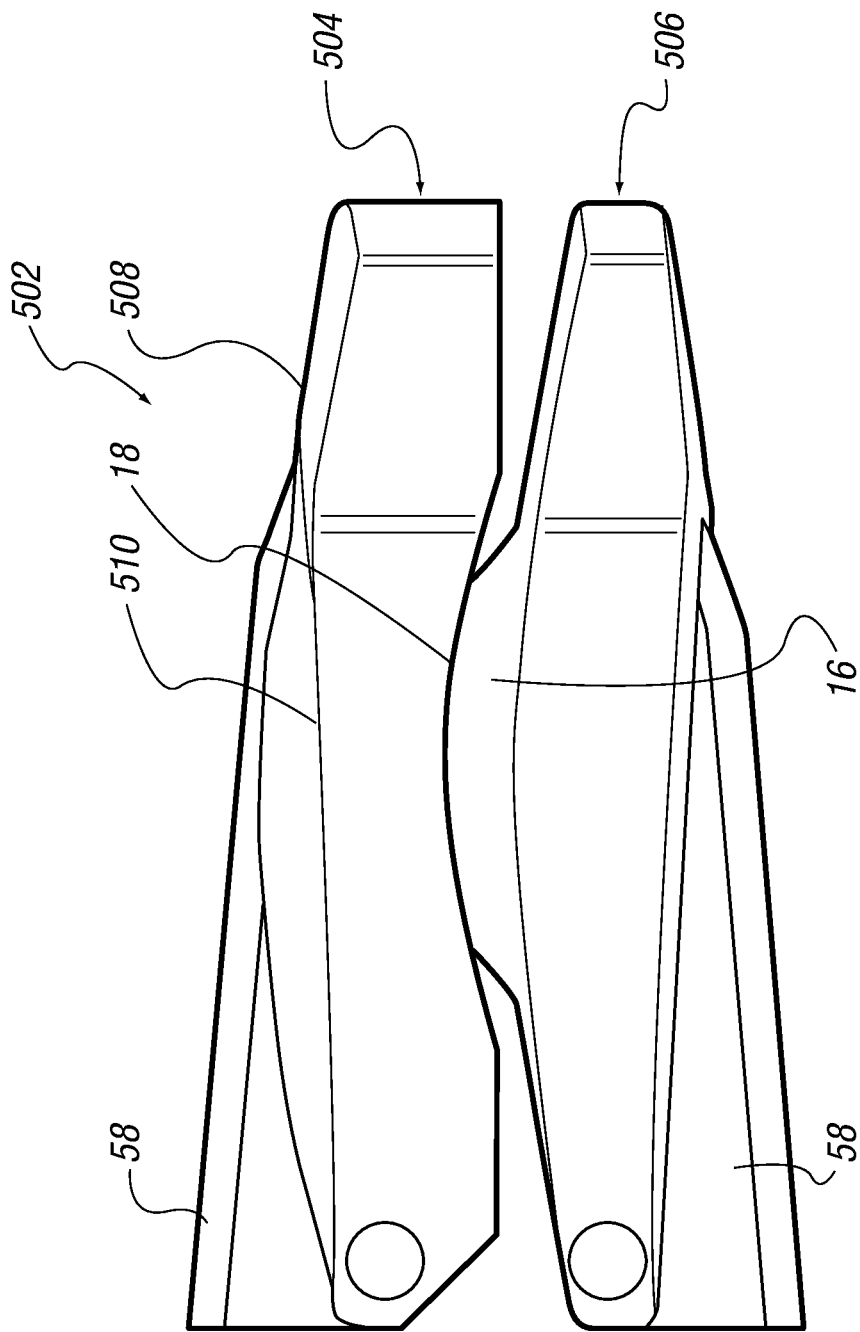
Figure 59C:
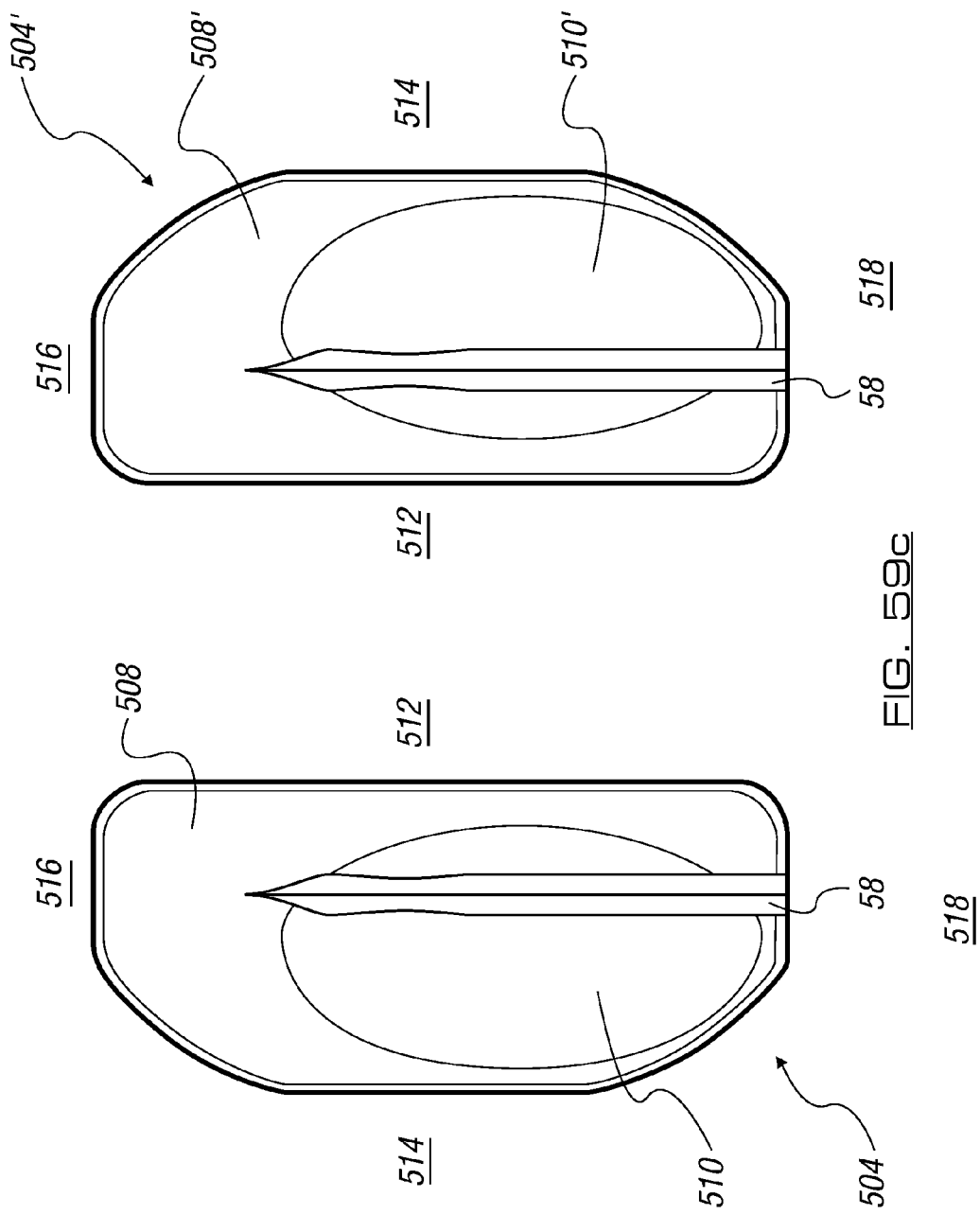

Referring to FIGS. 51-52b, prosthesis 202 is similar in appearance to prosthesis 102 and the same components are referred to in the two prostheses using the same reference numerals. However, in this embodiment, sliding or telescopic movement of male member 104 in channel portion 122 of female member 106 is limited firstly by locking means in the form of a locking screw 204, and secondly by guide means in the form of enclosed slot 206 and pin 207.

The portion 208 adjacent end 112 of male member 104 is of smaller dimensions than the remaining portion 210 of male member 104 adjacent end 108. A shoulder portion 212 is created between portions 208, 210 and, with male member 104 in a fully retracted position as shown in FIG. 52a, end 120 of female member 106 can be located in abutting relationship with shoulder portion 212 or a small spaced distance apart.

Portion 208 of male member 104 is provided with a plurality of recesses 214 at spaced apart locations along an anterior surface thereof. An end of locking screw 204 located through an aperture provided on the posterior surface of female member 106 is typically located in one of these recesses 214 if the position of the male member with respect to the female member is required to be locked.

Telescopic or sliding movement between female member 106 and male member 104 can be limited via enclosed slot 206 provided on an posterior surface of female member 106 adjacent end 120. A pin 207 provided on an anterior surface of male member 104 adjacent end 112 thereof is slidably mounted in slot 206, thereby guiding movement of the male member with respect to the female member and preventing complete dissociation of the two members from each other.

A further difference between prosthesis 202 and prosthesis 102 is that ends 108 and 116 of male member 104 and female member 106 are substantially rounded and continuous in form. These ends can be attached to a clamp and pedicle screw to allow attachment of the same to the required vertebral bodies above and below the disc.

Figure 60A:
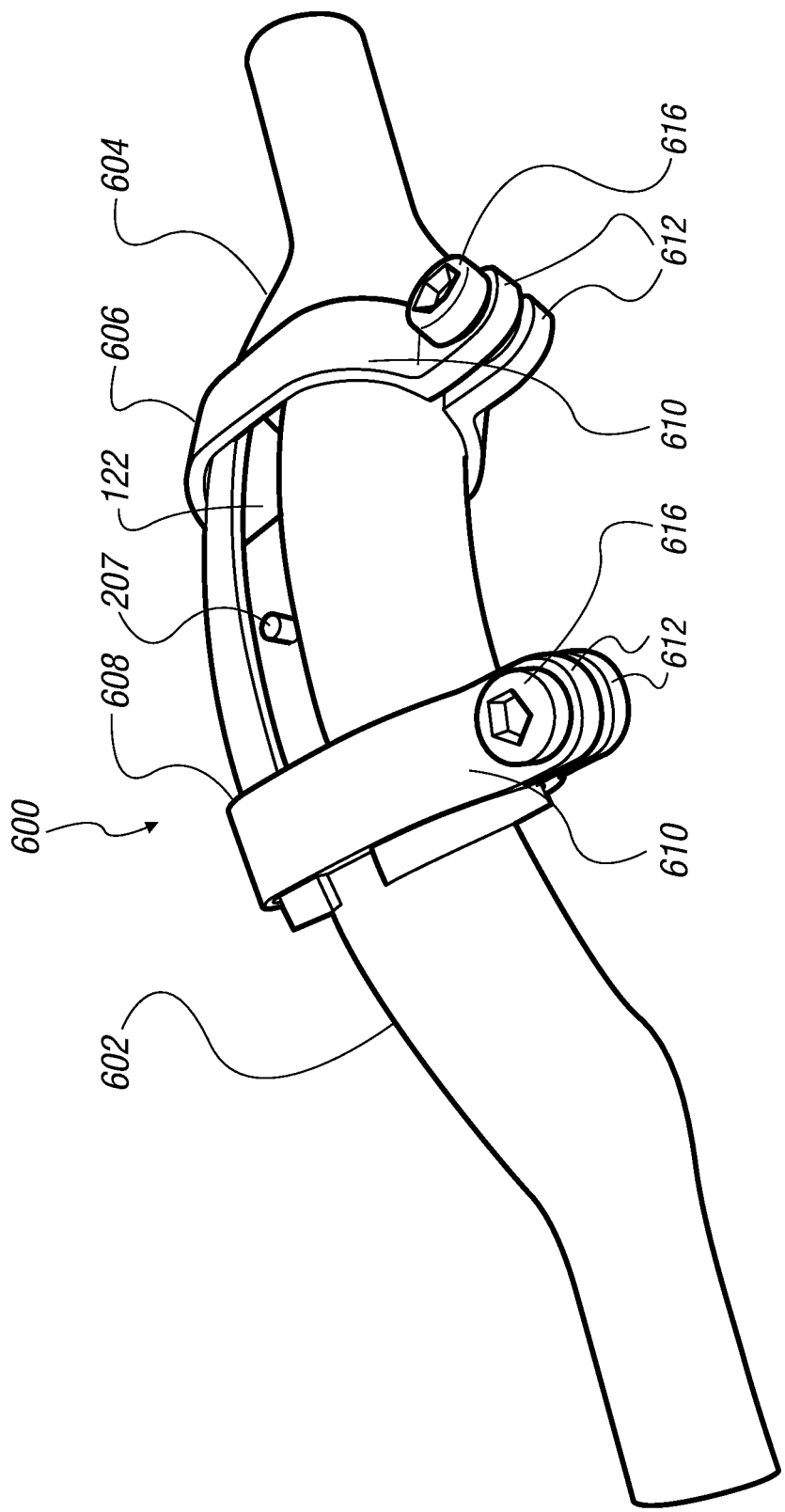
Figure 60C:
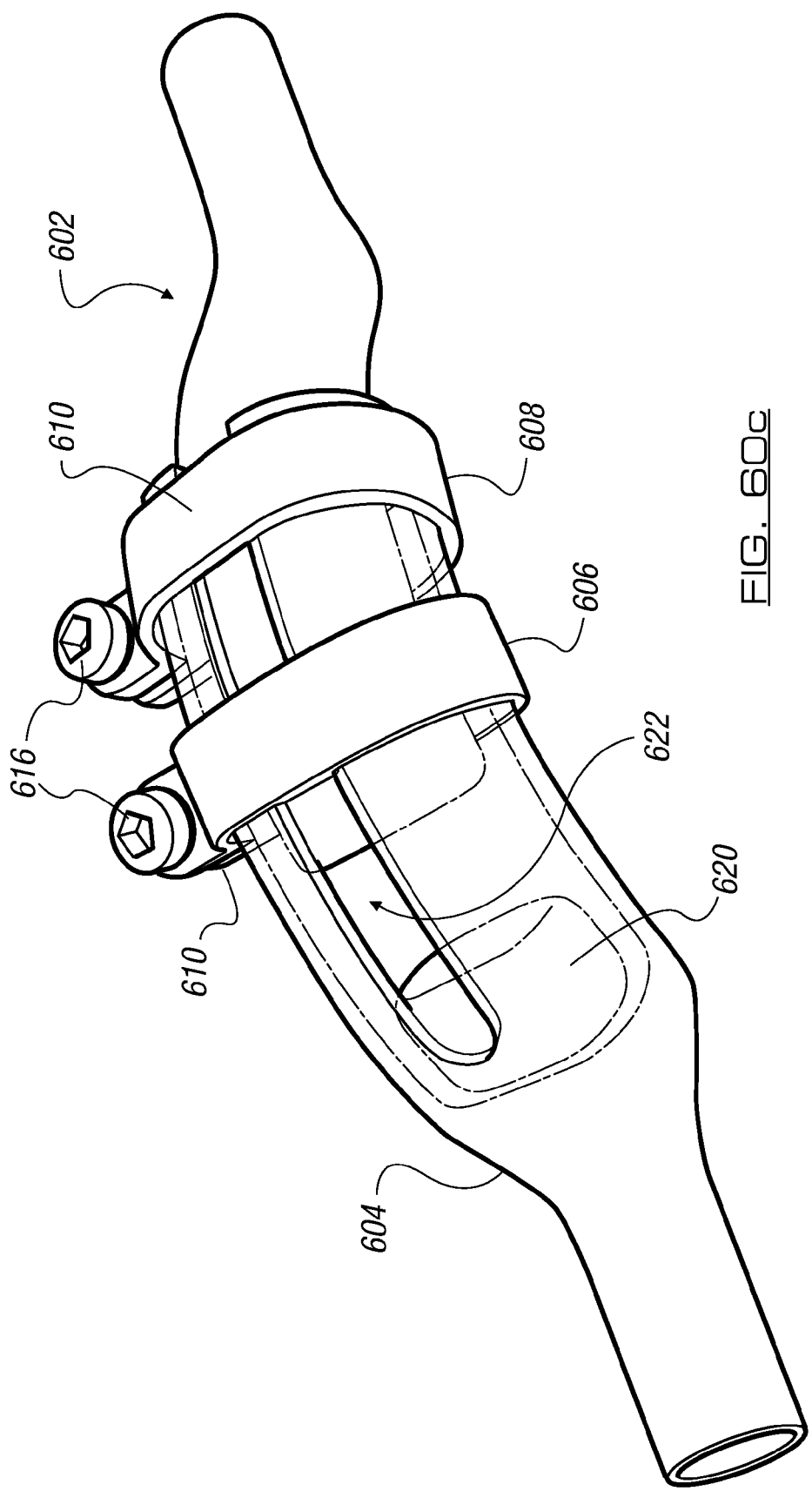
Figure 61:
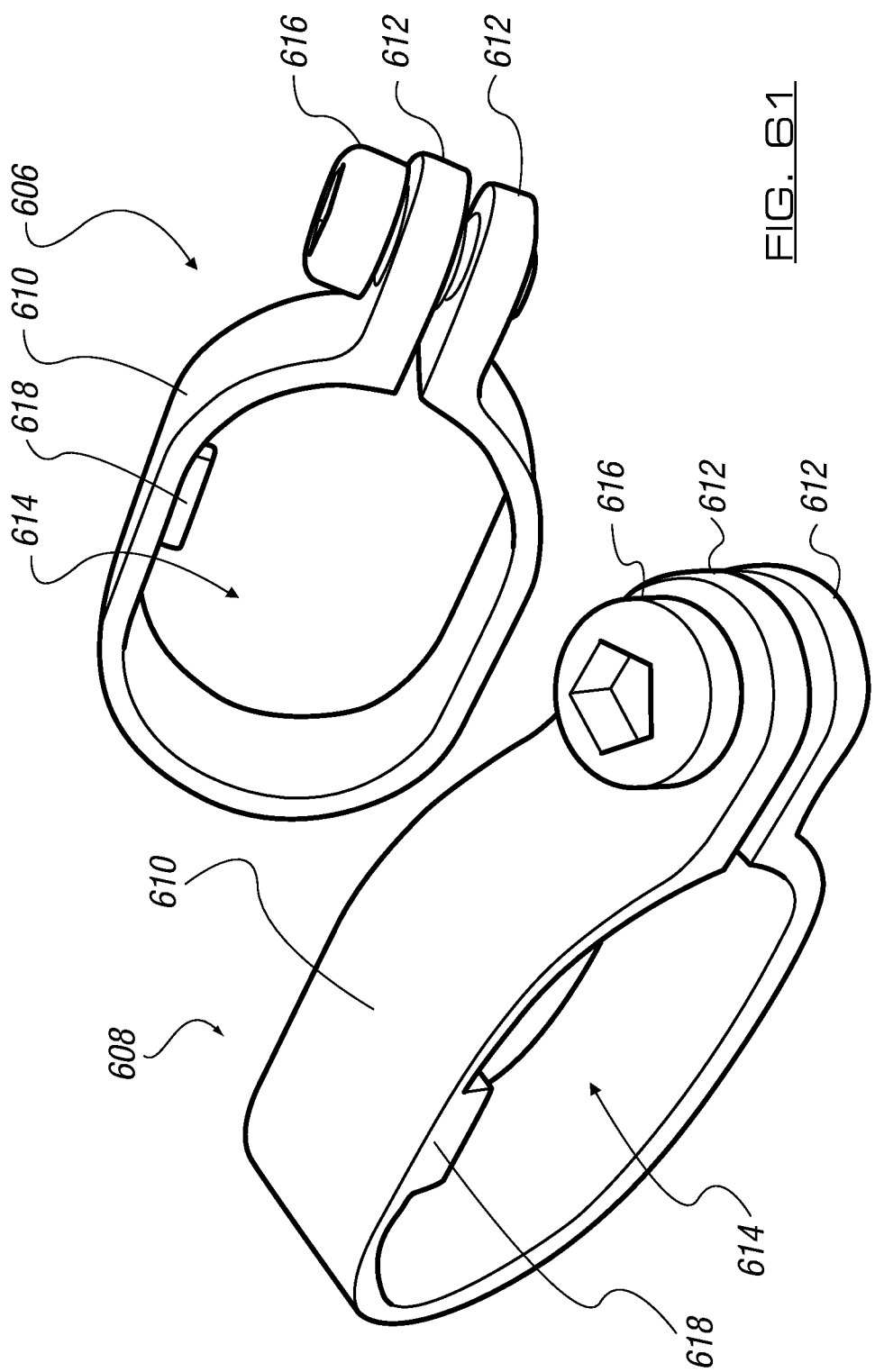
FIG. 61 illustrates clamping rings according to an embodiment of the present invention.

Referring to FIGS. 60a-61, there is illustrated a further embodiment of a facet joint prosthesis 600 according to the present invention. The prosthesis includes a male member 602 and a female member 604 which are similar in form to that described above and similar reference numerals are used to described corresponding parts. The difference of prosthesis 600 compared to the previously described embodiments are that the movement of male member 602 relative to female member 604 is limited by two clamping rings 606, 608. Thus, the clamping rings provide a clamping or compressive force around the two members when joined together to limit movement of the members relative to each other.

Clamping rings 606, 608 each have a sleeve portion 610 which is located around member 604, adjacent open ended slot 122 defined in said member 604. Plate members 612 protrude outwardly from the aperture 614 defined within sleeve portion 610 to define free ends of said clamping ring. The plate members 612 are a spaced distance apart and substantially parallel to each other. An aperture defined in each plate member allows a clamping screw 616 to be located therethrough so that a clamping force can be exerted via the clamping ring by tightening or loosening the screw.

A projection 618 is provided on an interior surface of sleeve portion 610 and said projection 618 is located in slot 122 in use to restrict movement of the clamping ring to sliding movement along slot 122.

The distance between clamping rings 606, 608 when located around female member determine the range of movement of male member 602 relative to female member 604 by limiting movement of pin 207 on male member 602. Thus, the clamping rings allow the facet joint prosthesis to undergo micromotion when the rings are close together or full/greater movement when the clamping rings are a greater distance apart from each other. This flexibility in movement ensures greater versatility of the prosthesis and allows the same to be multi-functional.

A stop member 620 can also be inserted in the channel 622 defined in female member 602 to limit movement of male member 602 in said channel. The free end of male member 602 is substantially rounded.

Thus, it can be seen that in one aspect of the present invention, the two pairs of lumbar disc prosthesis and the two pairs of facet joint prosthesis can be used to form a system designed to allow an arthroplasty to be performed through the posterior route, allowing movement between the vertebral bodies as well as restoring stability between the two vertebral bodies by allowing normal load transmission across the disc, freeing up the neural structures and replacing the facet joints as well.

Lumbar and Cervical Disc Prostheses for Insertion Via an Anterior Route

Referring to FIGS. 53a-58e, there is illustrated lumbar and cervical disc prostheses 302, 402 respectively for insertion via an anterior route as a replacement for a diseased and/or damaged lumbar or cervical disc.

The disc prostheses 302, 402 include a pair of disc member having an upper disc member 304, 404 and a lower disc member 306, 406. The upper disc members include a vertebral endplate contacting surface or superior surface 308, 408 and an inferior surface 310, 410. The lower disc members include a superior surface 312, 412 and a vertebral endplate contacting surface or inferior surface 314, 414.

The disc prostheses for insertion via an anterior route are the same as the lumbar disc prostheses for insertion via a posterior route apart from the following differences.

The protrusion 316, 416 provided on the superior surfaces 312, 412 of the lower disc members 306, 406 is rugby ball shaped rather than domed shaped. Thus, the radius of the curve of the protrusion in the medial lateral plane 318, 418 is larger than the radius of the curve in the anterior posterior plane 320, 420.

In the cervical prosthesis, the protrusion 416 extends for substantially the entire width in the medial-lateral plane and the anterior-posterior plane of the disc prosthesis.

The inferior surface 310, 410 of the upper disc members 304, 404 is divided into three sections a middle section 322, 422 and two end sections 324, 424 and 326, 426. The boundaries of the sections are provided in the medial-lateral plane 318, 418. The superior surface 312 of the lower disc member 306 can also be divided into similar three sections in the lumbar disc prosthesis.

The recess portion 328, 428 is provided in the middle section 322, 422 as with the earlier embodiments. The recess portion 328, 428 is substantially curved and the curvature of the medial part 330, 430 of the recessed portion is substantially symmetrical to the curvature of the lateral part 332, 432 (i.e. symmetrical about the midline). Thus, the lateral part 332, 432 has curvature corresponding to an arc of a circle which has a radius substantially equal to that of an arc of a circle corresponding to the curvature of the medial part 330, 430.

The radius of the curve of the recess portion 328, 428 is substantially equal to the radius of the curve of the protrusion 316, 416 in the medial-lateral plane 318.

Attachment means in the form of screws 334, 434 are provided adjacent an anterior edge 336, 436 of both the upper and lower disc prostheses. One screw is provided in the cervical prosthesis and two screws are provided in the lumbar prosthesis. Further attachment means in the form of spikes 338, 438 can be provided on the vertebral endplate contact surfaces to allow increased engagement with an adjacent vertebral disc member in use.

Lordosis is built into the prosthesis so that the anterior edge 336, 436 is larger in height than the posterior edge 338, 438.

What is claimed is:

1. A lumbar disc prosthesis defining a medial-lateral plane and a anterior-posterior plane, the lumbar disc comprising:
    a first pair of disc members including a first member having a vertebral endplate contact surface and a recessed portion on an opposing surface thereof, and a second member having a vertebral endplate contact surface and a protruding portion on an opposing surface thereof, the protruding portion of the second member engaging the recessed portion of the first member during use, the protruding portion defining a curvature in the medial-lateral plane defining a plurality of different radii values, the protruding portion extending along substantially the entire width of the medial-lateral plane; and
    a second pair of disc members, said second pair of disc members also including first and second members.

2. The prosthesis of claim 1, wherein the protruding portion defines a curvature in an anterior-posterior plane that is different than the curvature in the medial-lateral plane.

3. The prosthesis of claim 1, wherein the protruding portion defines a curvature in an anterior-posterior plane that is symmetrical about a midpoint of the curvature.

4. The prosthesis of claim 1, wherein the curvature in the medial-lateral plane is asymmetrical about a midpoint of the curvature.

5. The prosthesis of claim 4, wherein the curvature in the medial-lateral plane defines a medial radius less than a lateral radius defined by the curvature.

6. The prosthesis of claim 1, wherein the recessed portion defines a curvature in an anterior-posterior plane that is different than a curvature of the recessed portion defined in a medial-lateral plane.

* * * * *